United States Patent
Berg et al.

(10) Patent No.: US 7,683,067 B2
(45) Date of Patent: *Mar. 23, 2010

(54) 3-HETEROCYCLYL-INDOLE DERIVATIVES AS INHIBITORS OF GLYCOGEN SYNTHASE KINASE-3 (GSK-3)

(75) Inventors: Stefan Berg, Sodertalje (SE); Sven Hellberg, Sodertalje (SE)

(73) Assignee: AstraZeneca AB, Sodertalje (SE)

( * ) Notice: Subject to any disclaimer, the term of this patent is extended or adjusted under 35 U.S.C. 154(b) by 1012 days.

This patent is subject to a terminal disclaimer.

(21) Appl. No.: 10/572,778

(22) PCT Filed: Sep. 21, 2004

(86) PCT No.: PCT/SE2004/001363

§ 371 (c)(1),
(2), (4) Date: Mar. 21, 2006

(87) PCT Pub. No.: WO2005/027823

PCT Pub. Date: Mar. 31, 2005

(65) Prior Publication Data

US 2008/0275041 A1     Nov. 6, 2008

(30) Foreign Application Priority Data

Sep. 24, 2003 (SE) .................................. 0302546

(51) Int. Cl.
*A61K 31/496* (2006.01)
*A61K 31/4439* (2006.01)
*C07D 401/14* (2006.01)
*C07D 401/04* (2006.01)

(52) U.S. Cl. .................. 514/253.09; 514/339; 544/364; 546/277.7

(58) Field of Classification Search .............. 514/235.2, 514/397, 254.09, 339, 253.09, 318, 256, 514/235.5, 235.8; 544/373, 124, 364, 333; 546/277.7, 194
See application file for complete search history.

(56) References Cited

U.S. PATENT DOCUMENTS

| 6,987,110 | B2 | 1/2006 | Zhang et al. | |
|---|---|---|---|---|
| 7,205,314 | B2 | 4/2007 | Berg et al. | |
| 7,342,022 | B2 | 3/2008 | Berg et al. | |
| 7,399,780 | B2 * | 7/2008 | Berg et al. | 514/415 |
| 2005/0070559 | A1 | 3/2005 | Berg et al. | |
| 2005/0075351 | A1 | 4/2005 | Berg et al. | |

FOREIGN PATENT DOCUMENTS

| EP | 0667340 A1 | 8/1995 |
|---|---|---|
| WO | 9533750 A1 | 12/1995 |
| WO | WO 97/42187 | 11/1997 |
| WO | 0071129 A1 | 11/2000 |
| WO | 0125220 | 4/2001 |
| WO | WO 01/27081 A1 | 4/2001 |
| WO | 0132653 A1 | 5/2001 |
| WO | 0210158 A2 | 2/2002 |
| WO | WO 02/30868 A1 | 4/2002 |
| WO | 03053444 A1 | 7/2003 |
| WO | WO 03/053330 A2 | 7/2003 |
| WO | WO 03/055492 A1 | 7/2003 |
| WO | WO 03/055877 A1 | 7/2003 |
| WO | WO 03/082853 A1 | 10/2003 |

OTHER PUBLICATIONS

Imahori and Uchida, "Physiology and Pathology of Tau Protein Kinases in Relation to Alzheimer's Disease", J. Biochem, vol. 121, p. 179-188, 1997.
Hoshi, et al., "Regulation of Mitochondrial pyruvate . . . Kinase 3β in Brain", PNAS, vol. 93, pp. 2719-2723, 1996.
Bhat, et. al., "Regulation and Localization of Tyrosine . . . Neuronal Degeneration" , PNAS, vol. 97, p. 11074-11079, 2000.
Stambolic, et. al., "Lithium Inhibits Glycogen Synthase . . . in Intact Cells", Curr. Biol., vol. 6, pp. 1664-1668, 1996.
Klein and Melton, "A Molecular Mechanism for the Effect of Lithium on Development", PNAS, vol. 93, p. 8455-8459, 1996.
Kozlovsky, et. al., "Low GSK-3β Immunoreactivity . . . of Schizophrenic Patients", Am. J. Psychiatry May 2000, vol. 157(5), p. 831-833.

(Continued)

*Primary Examiner*—Kamal A Saeed
*Assistant Examiner*—Kristin Bianchi
(74) *Attorney, Agent, or Firm*—Kenneth F. Mitchell

(57) ABSTRACT

Compounds of formula Ia or Ib

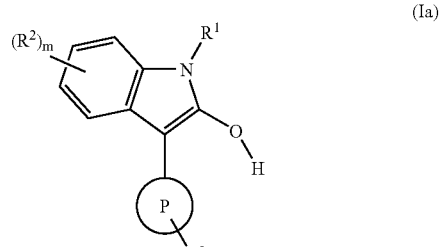

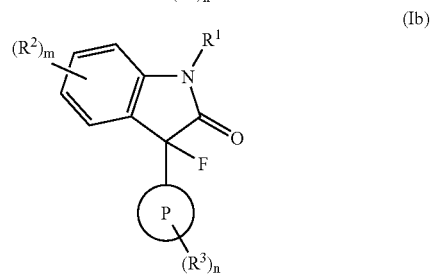

wherein P; $R^1$; $R^2$; m; and n are as defined in the application, salts thereof, processed for their preparation, new intermediates used therein, pharmaceutical formulations containing said compounds and the use of said compounds in therapy.

9 Claims, No Drawings

OTHER PUBLICATIONS

Cotter, et. al., "Abnormalities of Wnt Signalling . . . Neurodevelopmental Abnormality", Neuroreport, vol. 9, p. 1379-1383, 1998.

Nikoulina, et. al., "Potential Role of Glycogen . . . of Type 2 Diabetes", Diabetes Feb. 2000, vol. 49(2), pp. 263-271.

Gat, et. al., "De Novo Hair Follicle . . . a Truncated β-Catenin in Skin", Cell, Nov. 25, 1998, vol. 95(5), p. 605-614.

Vijayaraghavan, et. al., "A Role for Phosphorylation . . . Motility Regulation", Biol. Reprod., Jun. 2000, vol. 62(6), p. 1647-1654.

Naegeli, et. al., "2-Amino-Pyridin-5- . . . Abkommlinge", Helv. Chim. Acta., vol. 21, pp. 1746-1756, 1938.

Sun, et. al., "Identification of Substituted 3- . . . Tyrosine Kinases", J. Med. Chem. Bol. 43(14), pp. 2655-2663 (2000).

Tilley, et. al., "Synthesis of Heterocyclic Analogs of α-Methyldopa", J. Heterocyclic Chem., vol. 16, pp. 333-337, 1979.

Krapcho, et. al., "Antispasmodics. I. Basic Amides of Benzilic Acid", J. Am. Chem. Soc., vol. 77, pp. 3632-3634, 1955.

Li Sun, et. al., "Design, Synthesis, and Evaluations of Substituted . . . Tyrosine Kinases", J. Med Chem., vol. 42, pp. 5120-5130, 1999.

L. Thunus, "Synthese et Proprietes . . . (Substitution 2,5) (*)", Annales Pharmaceutiques Francaises, vol. 35, pp. 197-204, 1977.

Tobias, et. al., "Novel Therapeutic Targets in Osteoporosis", Expert Opinion on Therapeutic Targets, Feb. 2002, pp. 41-46.

* cited by examiner

3-HETEROCYCLYL-INDOLE DERIVATIVES AS INHIBITORS OF GLYCOGEN SYNTHASE KINASE-3 (GSK-3)

CROSS-REFERENCE TO RELATED APPLICATIONS

This application is a US National Stage under 35 U.S.C § 371 of International Application No. PCT/SE2004/001363 (filed Sep. 21, 2004) that claims priority under 35 U.S.C. Section 119(a)-(d) to Application No. 0302546-7 filed on Sep. 24, 2003 in Sweden.

FIELD OF THE INVENTION

The present invention relates to new compounds of formula Ia and Ib, as a free base or a salt thereof, to pharmaceutical formulations containing said compounds and to the use of said compounds in therapy. The present invention further relates to processes for the preparation of compounds of formula Ia and Ib and to new intermediates used in the preparation thereof.

BACKGROUND OF THE INVENTION

Glycogen synthase kinase 3 (GSK3) is a serine/threonine protein kinase composed of two isoforms ($\alpha$ and $\beta$), which are encoded by distinct genes but are highly homologous within the catalytic domain. GSK3 is highly expressed in the central and peripheral nervous system. GSK3 phosphorylates several substrates including tau, $\beta$-catenin, glycogen synthase, pyruvate dehydrogenase and elongation initiation factor 2b (eIF2b). Insulin and growth factors activate protein kinase B, which phosphorylates GSK3 on serine 9 residue and inactivates it.

Alzheimer's Disease (AD) Dementias, and Taupathies

AD is characterized by cognitive decline, cholinergic dysfunction and neuronal death, neurofibrillary tangles and senile plaques consisting of amyloid-$\beta$ deposits. The sequence of these events in AD is unclear, but is believed to be related. Glycogen synthase kinase 3$\beta$ (GSK3$\beta$) or Tau ($\tau$) phosphorylating kinase selectively phosphorylates the microtubule associated protein $\tau$ in neurons at sites that are hyperphosphorylated in AD brains. Hyperphosphorylated protein $\tau$ has lower affinity for microtubules and accumulates as paired helical filaments, which are the main components that constitute neurofibrillary tangles and neuropil threads in AD brains. This results in depolymerization of microtubules, which leads to dying back of axons and neuritic dystrophy. Neurofibrillary tangles are consistently found in diseases such as AD, amyotrophic lateral sclerosis, parkinsonism-dementia of Gaum, corticobasal degeneration, dementia pugilistica and head trauma, Down's syndrome, postencephalatic parkinsonism, progressive supranuclear palsy, Niemann-Pick's Disease and Pick's Disease. Addition of amyloid-$\beta$ to primary hippocampal cultures results in hyperphosphorylation of $\tau$ and a paired helical filaments-like state via induction of GSK3$\beta$ activity, followed by disruption of axonal transport and neuronal death (Imahori and Uchida, J. Biochem 121: 179-188, 1997). GSK3$\beta$ preferentially labels neurofibrillary tangles and has been shown to be active in pre-tangle neurons in AD brains. GSK3 protein levels are also increased by 50% in brain tissue from AD patients. Furthermore, GSK3$\beta$ phosphorylates pyruvate dehydrogenase, a key enzyme in the glycolytic pathway and prevents the conversion of pyruvate to acetyl-Co-A (Hoshi et al., PNAS 93:2719-2723, 1996). Acetyl-Co-A is critical for the synthesis of acetylcholine, a neurotransmitter with cognitive functions. Thus, GSK3$\beta$ inhibition may have beneficial effects in progression as well as the cognitive deficits associated with Alzheimer's disease and other above-referred to diseases.

Chronic and Acute Neurodegenerative Diseases

Growth factor mediated activation of the PI3K/Akt pathway has been shown to play a key role in neuronal survival. The activation of this pathway results in GSK3$\beta$ inhibition. Recent studies (Bhat et. al., PNAS 97:11074-11079 (2000)) indicate that GSK3$\beta$ activity is increased in cellular and animal models of neurodegeneration such as cerebral ischemia or after growth factor deprivation. For example, the active site phosphorylation was increased in neurons vulnerable to apoptosis, a type of cell death commonly thought to occur in chronic and acute degenerative diseases such as Alzheimer's Disease, Parkinson's Disease, amyotrophic lateral sclerosis, Huntington's Disease and HIV dementia, ischemic stroke and head trauma. Lithium was neuroprotective in inhibiting apoptosis in cells and in the brain at doses that resulted in the inhibition of GSK3$\beta$. Thus GSK3$\beta$ inhibitors could be useful in attenuating the course of neurodegenerative diseases.

Bipolar Disorders (BD)

Bipolar Disorders are characterised by manic episodes and depressive episodes. Lithium has been used to treat BD based on its mood stabilising effects. The disadvantage of lithium is the narrow therapeutic window and the danger of overdosing that can lead to lithium intoxication. The recent discovery that lithium inhibits GSK3 at therapeutic concentrations has raised the possibility that this enzyme represents a key target of lithium's action in the brain (Stambolic et al., Curr. Biol. 6:1664-1668, 1996; Klein and Melton; PNAS 93:8455-8459, 1996). Inhibition of GSK3$\beta$ may therefore be of therapeutic relevance in the treatment of BD as well as in AD patients that have affective disorders.

Schizophrenia

GSK3 is involved in signal transduction cascades of multiple cellular processes, particularly during neural development. Kozlovsky et al (Am J Psychiatry 2000 May; 157(5): 831-3) found that GSK3$\beta$ levels were 41% lower in the schizophrenic patients than in comparison subjects. This study indicates that schizophrenia involves neurodevelopmental pathology and that abnormal GSK3 regulation could play a role in schizophrenia. Furthermore, reduced $\beta$-catenin levels have been reported in patients exhibiting schizophrenia (Cotter et al., Neuroreport 9:1379-1383 (1998)).

Diabetes

Insulin stimulates glycogen synthesis in skeletal muscles via the dephosphorylation and thus activation of glycogen synthase. Under resting conditions, GSK3 phosphorylates and inactivates glycogen synthase via dephosphorylation. GSK3 is also over-expressed in muscles from Type II diabetic patients (Nikoulina et al., Diabetes 2000 February; 49(2): 263-71). Inhibition of GSK3 increases the activity of glycogen synthase thereby decreasing glucose levels by its conversion to glycogen. GSK3 inhibition may therefore be of therapeutic relevance in the treatment of Type I and Type II diabetes, diabetic neuropathy and diabetes related disorders.

Hair Loss

GSK3 phosphorylates and degrades $\beta$-catenin. $\beta$-catenin is an effector of the pathway for keratonin synthesis. $\beta$-catenin stabilisation may be lead to increase hair development. Mice expressing a stabilised $\beta$-catenin by mutation of sites phosphorylated by GSK3 undergo a process resembling de novo hair morphogenesis (Gat et al., Cell 1998 Nov. 25; 95 (5): 605-14)). The new follicles formed sebaceous glands and dermal papilla, normally established only in embryogenesis. Thus GSK3 inhibition may offer treatment for baldness.

Oral Contraceptives

Vijajaraghavan et al. (Biol Reprod 2000 June; 62 (6):1647-54) reported that GSK3 is high in motile versus immotile sperm. Immunocytochemistry revealed that GSK3 is present in the flagellum and the anterior portion of the sperm head. These data suggest that GSK3 could be a key element underlying motility initiation in the epididymis and regulation of mature sperm function. Inhibitors of GSK3 could be useful as contraceptives for males.

Bone Disorders

It has been shown that GSK3 inhibitors could be used for treatment of bone-related disorders. This has been discussed in e.g. Tobias et al., *Expert Opinion on Therapeutic Targets*, February 2002, pp 41-56.

DISCLOSURE OF INVENTION

The object of the present invention is to provide compounds having a selective inhibiting effect at GSK3 as well as having a good bioavailability. Accordingly, the present invention provides a compound of formula Ia or Ib:

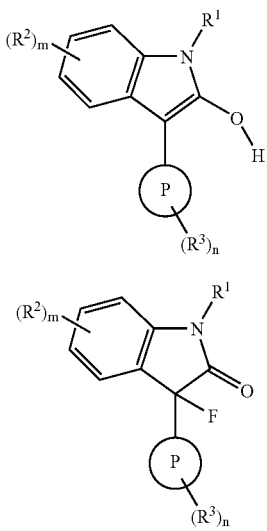

wherein:

P represents a 5- or 6-membered heteroaromatic ring containing one or two heteroatoms selected independently from N, O and S of which at least one heteroatom is nitrogen;

$R^1$ is hydrogen;

$R^2$ is selected from: $C_{1-6}$alkyl, cyano, halogen, (CO)OR$^{10}$, and CONR$^{10}$R$^{11}$;

$R^3$ is selected from: $C_{1-6}$alkyl, cyano, nitro, (CO)OR$^4$, $C_{1-6}$alkylNR$^4$R$^5$, OC$_{2-6}$alkylNR$^4$R$^5$, CONR$^4$R$^5$, SO$_2$R$^4$, OSO$_2$R$^4$ and (SO$_2$)NR$^4$R$^5$;

$R^4$ is selected from: hydrogen, CF$_3$ and $C_{1-6}$alkyl;

$R^5$ is selected from: hydrogen, $C_{1-6}$alkyl, $C_{1-6}$alkylNR$^6$R$^7$ and; wherein $R^4$ and $R^5$ may together form a 4-, 5-, 6- or 7-membered heterocyclic group containing one or more heteroatoms selected independently from N, O and S, wherein said heterocyclic group may optionally be substituted by a group Y;

$R^6$ and $R^7$ are independently selected from hydrogen, $C_{1-6}$alkyl, (CO)$C_{1-6}$alkyl, and wherein $R^6$ and $R^7$ may together form a 5- or 6-membered heterocyclic group containing one or more heteroatoms, selected independently from N, O and S, wherein said heterocyclic group may optionally be substituted by a group Y;

$R^8$ and $R^9$ are independently selected from: hydrogen and $C_{1-6}$alkyl and wherein $R^8$ and $R^9$ may together form a 5- or 6-membered heterocyclic group containing one or more heteroatoms, selected independently from N, O and S;

$R^{10}$ is selected from hydrogen and $C_{1-6}$alkyl;

$R^{11}$ is selected from hydrogen, $C_{1-6}$alkyl, $C_{1-6}$alkylCN, $C_{0-6}$alkylaryl, $C_{2-6}$alkylOR$^8$, $C_{1-6}$alkyl(CO)NR$^6$R$^7$, $C_{1-6}$alkyl(SO$_2$)R$^6$, $C_{1-6}$alkyl(SO$_2$)NR$^6$R$^7$, $C_{0-6}$alkylheteroaryl, $C_{0-6}$alkylC$_{3-6}$heterocyclic group and $C_{1-6}$alkylNR$^6$R$^7$; and wherein any $C_{0-6}$alkylaryl and $C_{0-6}$alkylheteroaryl may be substituted by one or more group Z; and wherein any $C_{0-6}$alkylC$_{3-6}$heterocyclic group may be substituted by one or more group Y;

Z is selected from halo, $C_{1-6}$alkyl, $C_{1-6}$alkoxy, OCF$_3$ and CF$_3$;

Y is selected from: oxo, $C_{2-6}$alkylOR$^8$, $C_{1-6}$alkyl, $C_{0-6}$alkylaryl, $C_{0-6}$alkylheteroaryl, OR$^8$ and $C_{2-6}$alkylNR$^8$R$^9$;

m is 0, 1, 2, 3 or 4;

n is 0, 1, 2, 3 or 4;

as a free base or a salt, or a tautomer thereof.

One aspect of the invention relates to compounds of formula Ia or Ib, wherein:

P represents a 6-membered heteroaromatic ring containing one heteroatom selected independently from N and O;

$R^2$ is selected from: cyano, halogen, (CO)OR$^{10}$, and CONR$^{10}$R$^{11}$;

$R^3$ is selected from: cyano, nitro, $C_{1-6}$alkylNR$^4$R$^5$, OC$_{2-6}$alkylNR$^4$R$^5$, CONR$^4$R$^5$, and (SO$_2$)NR$^4$R$^5$;

$R^4$ is selected from: hydrogen and $C_{1-6}$alkyl;

$R^5$ is selected from: $C_{1-6}$alkyl and $C_{1-6}$alkylNR$^6$R$^7$ and; wherein $R^4$ and $R^5$ may together form a 5- or 6-membered heterocyclic group containing one or more heteroatoms selected independently from N and O, wherein said heterocyclic group may optionally be substituted by a group Y;

$R^6$ and $R^7$ are independently selected from hydrogen, (CO)$C_{1-6}$alkyl, and wherein $R^6$ and $R^7$ may together form a 5- or 6-membered heterocyclic group containing one or more heteroatoms, selected independently from N and O, wherein said heterocyclic group may optionally be substituted by a group Y;

$R^8$ and $R^9$ are independently selected from: hydrogen and $C_{1-6}$alkyl and wherein $R^8$ and $R^9$ may together form a 5- or 6-membered heterocyclic group containing one or more heteroatoms, selected independently from N and O;

$R^{10}$ is selected from hydrogen and $C_{1-6}$alkyl;

$R^{11}$ is selected from hydrogen, $C_{1-6}$alkyl, $C_{1-6}$alkylCN, $C_{0-6}$alkylaryl, $C_{2-6}$alkylOR$^8$, $C_{1-6}$alkyl(CO)NR$^6$R$^7$, $C_{1-6}$alkyl(SO$_2$)R$^6$, $C_{1-6}$alkyl(SO$_2$)NR$^6$R$^7$, $C_{0-6}$alkylheteroaryl, $C_{0-6}$alkylC$_{3-6}$heterocyclic group and $C_{1-6}$alkylNR$^6$R$^7$; and wherein any $C_{0-6}$alkylaryl may be substituted by one or more group Z;

Z is selected from halo, $C_{1-6}$alkoxy, OCF$_3$ and CF$_3$;

Y is selected from: oxo, $C_{2-6}$alkylOR$^8$, $C_{1-6}$alkyl and $C_{2-4}$alkylNR$^8$R$^9$;

m is 1 or 2;

n is 1.

Another aspect of the invention relates to compounds of formula Ia or Ib, wherein P is pyridine.

Another aspect of the invention relates to compounds of formula Ia or Ib, wherein R$^2$ is selected from: cyano, (CO)OR$^{10}$, and CONR$^{10}$R$^{11}$.

Yet another aspect of the invention relates to compounds of formula Ia or Ib, wherein R$^2$ is CONR$^{10}$R$^{11}$; and R$^{11}$ is selected from hydrogen, $C_{1-6}$alkyl, $C_{1-6}$alkylCN, $C_{2-6}$alkylOR$^8$, $C_{0-6}$alkylaryl, $C_{0-6}$alkylheteroaryl; and wherein any $C_{0-6}$alkylaryl and $C_{0-6}$alkylheteroaryl may be substituted by one or more group Z; and wherein Z is selected from $C_{1-6}$alkoxy, OCF$_3$ and CF$_3$.

Yet another aspect of the invention relates to compounds of formula Ia or Ib, wherein R$^3$ is selected from: $C_{1-6}$alkylNR$^4$R$^5$, OC$_{2-6}$alkylNR$^4$R$^5$, CONR$^4$R$^5$, and (SO$_2$)NR$^4$R$^5$; and wherein R$^4$ and R$^5$ may together form a 6-membered heterocyclic group containing one or two heteroatoms selected independently from N and O, wherein said heterocyclic group may optionally be substituted by a group Y, and wherein Y may be $C_{1-6}$alkyl.

Yet another aspect of the invention relates to compounds of formula Ia or Ib, wherein R$^3$ is selected from: $C_{1-6}$alkylNR$^4$R$^5$, OC$_{2-6}$alkylNR$^4$R$^5$, CONR$^4$R$^5$, and (SO$_2$)NR$^4$R$^5$; and R$^5$ is $C_{1-6}$alkylNR$^6$R$^7$ and wherein R$^6$ and R$^7$ may together form a 5- or 6-membered heterocyclic group containing one or two heteroatoms, selected independently from N and O, wherein said heterocyclic group may optionally be substituted by a group Y.

Yet another aspect of the invention relates to compounds of formula Ia or Ib, wherein R$^3$ is $C_{1-6}$alkylNR$^4$R$^5$; and wherein R$^4$ and R$^5$ may together form a 6-membered heterocyclic group containing one or two heteroatoms selected independently from N and O, wherein said heterocyclic group may optionally be substituted by a group Y and wherein Y may be $C_{1-6}$alkyl or oxo.

In a further aspect of the invention the following compounds are provided:

2-Hydroxy-3-{5-[(4-methylpiperazin-1-yl)carbonyl]pyridin-2-yl}-1H-indole-6-carbonitrile hydrochloride;
6-(6-Cyano-2-hydroxy-1H-indol-3-yl)-N-(2-morpholin-4-ylethyl)nicotinamide hydrochloride;
6-(6-Cyano-2-hydroxy-1H-indol-3-yl)-N-methyl-N-(2-pyrrolidin-1-ylethyl)nicotinamide hydrochloride;
6-(6-Cyano-2-hydroxy-1H-indol-3-yl)-N-(2-(dimethylamino)ethyl)-N-methylnicotinamide hydrochloride;
6-(6-Cyano-2-hydroxy-1H-indol-3-yl)-N-(2-pyrrolidin-1-ylethyl)pyridine-3-sulfonamide hydrochloride;
2-Hydroxy-3-[5-(piperazine-1-sulfonyl)pyridin-2-yl]-1H-indole-6-carbonitrile hydrochloride;
3-[5-({4-[2-(Dipropylamino)ethyl]piperazin-1-yl}sulfonyl)pyridin-2-yl]-2-hydroxy-1H-indole-6-carbonitrile hydrochloride;
2-Hydroxy-3-(5-{[4-(2-morpholin-4-ylethyl)piperazin-1-yl]sulfonyl}pyridin-2-yl)-1H-indole-6-carbonitrile hydrochloride;
2-Hydroxy-3-(5-{[4-(2-pyrrolidin-1-ylethyl)piperazin-1-yl]sulfonyl}pyridin-2-yl)-1H-indole-6-carbonitrile hydrochloride;
2-Hydroxy-3-(5-{[4-(2-methoxyethyl)piperazin-1-yl]sulfonyl}pyridin-2-yl)-1H-indole-6-carbonitrile hydrochloride;
2-Hydroxy-N-(3-methoxypropyl)-3-{5-[(4-methylpiperazin-1-yl)sulfonyl]pyridin-2-yl}-1H-indole-5-carboxamide hydrochloride;
2-Hydroxy-N-(2-methoxyethyl)-3-[5-(morpholin-4-ylmethyl)pyridin-2-yl]-1H-indole-5-carboxamide hydrochloride;
2-Hydroxy-3-[5-(morpholin-4-ylmethyl)pyridin-2-yl]-N-(pyridin-2-ylmethyl)-1H-indole-5-carboxamide hydrochloride;
2-Hydroxy-3-[5-(morpholin-4-ylmethyl)pyridin-2-yl]-N-(2-thienylmethyl)-1H-indole-5-carboxamide hydrochloride;
2-Hydroxy-3-[5-(morpholin-4-ylmethyl)pyridin-2-yl]-N-[2-(2-oxoimidazolidin-1-yl)ethyl]-1H-indole-5-carboxamide hydrochloride;
N-[2-(Acetylamino)ethyl]-2-hydroxy-3-[5-(morpholin-4-ylmethyl)pyridin-2-yl]-1H-indole-5-carboxamide hydrochloride;
2-Hydroxy-N-(2-methoxybenzyl)-3-[5-(morpholin-4-ylmethyl)pyridin-2-yl]-1H-indole-5-carboxamide hydrochloride;
2-Hydroxy-3-[5-(morpholin-4-ylmethyl)pyridin-2-yl]-N-[4-(trifluoromethyl)benzyl]-1H-indole-5-carboxamide hydrochloride;
2-Hydroxy-3-[5-(morpholin-4-ylmethyl)pyridin-2-yl]-N-[2-(trifluoromethyl)benzyl]-1H-indole-5-carboxamide hydrochloride;
2-Hydroxy-3-[5-(morpholin-4-ylmethyl)pyridin-2-yl]-N-[2-(trifluoromethoxy)benzyl]-1H-indole-5-carboxamide hydrochloride;
2-Hydroxy-3-[5-(morpholin-4-ylmethyl)pyridin-2-yl]-N-[4-(trifluoromethoxy)benzyl]-1H-indole-5-carboxamide hydrochloride;
3-{5-[(Diethylamino)methyl]pyridin-2-yl}-2-hydroxy-N-(2-thienylmethyl)-1H-indole-5-carboxamide hydrochloride;
3-{5-[(Diethylamino)methyl]pyridin-2-yl}-2-hydroxy-N-(pyridin-2-ylmethyl)-1H-indole-5-carboxamide hydrochloride;
3-{5-[(Diethylamino)methyl]pyridin-2-yl}-2-hydroxy-N-(2-methoxyethyl)-1H-indole-5-carboxamide hydrochloride;
2-Hydroxy-3-[5-(morpholin-4-ylmethyl)pyridin-2-yl]-N-(tetrahydrofuran-2-ylmethyl)-1H-indole-5-carboxamide hydrochloride;
N-Benzyl-2-hydroxy-3-[5-(morpholin-4-ylmethyl)pyridin-2-yl]-1H-indole-5-carboxamide hydrochloride;
2-Hydroxy-3-[5-(morpholin-4-ylmethyl)pyridin-2-yl]-N-propyl-1H-indole-5-carboxamide hydrochloride:
2-Hydroxy-N-(2-methoxyphenyl)-3-{5-[(4-methylpiperazin-1-yl)sulfonyl]pyridin-2-yl}-1H-indole-5-carboxamide hydrochloride;
2-Hydroxy-N-(4-methoxyphenyl)-3-{5-[(4-methylpiperazin-1-yl)sulfonyl]pyridin-2-yl}-1H-indole-5-carboxamide hydrochloride;
2-Hydroxy-3-{5-[(4-methylpiperazin-1-yl)sulfonyl]pyridin-2-yl}-N-(pyridin-3-ylmethyl)-1H-indole-5-carboxamide hydrochloride;
2-Hydroxy-3-{5-[(4-methylpiperazin-1-yl)sulfonyl]pyridin-2-yl}-N-(pyridin-4-ylmethyl)-1H-indole-5-carboxamide hydrochloride;
2-Hydroxy-3-{5-[(4-methylpiperazin-1-yl)sulfonyl]pyridin-2-yl}-N-(pyridin-2-ylmethyl)-1H-indole-5-carboxamide hydrochloride;

N-[2-(Aminosulfonyl)ethyl]-2-hydroxy-3-[5-(morpholin-4-ylmethyl)pyridin-2-yl]-1H-indole-5-carboxamide hydrochloride;

2-Hydroxy-N-[2-(methylsulfonyl)ethyl]-3-[5-(morpholin-4-ylmethyl)pyridin-2-yl]-1H-indole-5-carboxamide hydrochloride;

3-(5-Cyanopyridin-2-yl)-2-hydroxy-N-{2-[(4-methylpiperazin-1-yl)sulfonyl]ethyl}-1H-indole-5-carboxamide hydrochloride;

2-Hydroxy-3-[5-(morpholin-4-ylmethyl)pyridin-2-yl]-1H-indole-5-carboxamide hydrochloride;

2-Hydroxy-3-{5-[(4-methylpiperazin-1-yl)sulfonyl]pyridin-2-yl}-1H-indole-5-sulfonamide hydrochloride;

2-Hydroxy-3-{5-[(4-methylpiperazin-1-yl)sulfonyl]pyridin-2-yl}-1H-indole-5-carboxamide hydrochloride;

2-Hydroxy-3-{5-[(4-methylpiperazin-1-yl)sulfonyl]pyridin-2-yl}-1H-indole-6-carboxamide hydrochloride;

3-[5-({4-[2-(Dimethylamino)ethyl]piperazin-1-yl}sulfonyl)pyridin-2-yl]-2-hydroxy-1H-indole-6-carbonitrile hydrochloride;

2-Hydroxy-N-(2-methoxyethyl)-3-(5-nitropyridin-2-yl)-1H-indole-5-carboxamide hydrochloride;

N-(2-Cyanoethyl)-2-hydroxy-3-[5-(morpholin-4-ylmethyl)pyridin-2-yl]-1H-indole-5-carboxamide hydrochloride;

2-Hydroxy-N-[2-(1H-imidazol-4-yl)ethyl]-3-{5-[(4-methylpiperazin-1-yl)sulfonyl]pyridin-2-yl}-1H-indole-5-carboxamide hydrochloride;

N-Benzyl-2-hydroxy-3-{5-[(4-methylpiperazin-1-yl)sulfonyl]pyridin-2-yl}-1H-indole-5-carboxamide hydrochloride;

2-Hydroxy-3-{5-[(4-methylpiperazin-1-yl)sulfonyl]pyridin-2-yl}-N-propyl-1H-indole-5-carboxamide hydrochloride;

2-Hydroxy-N-(2-methoxyethyl)-3-{5-[(4-methylpiperazin-1-yl)sulfonyl]pyridin-2-yl}-H-indole-5-carboxamide hydrochloride;

N-[2-(Dimethylamino)ethyl]-2-hydroxy-3-{5-[(4-methylpiperazin-1-yl)sulfonyl]pyridin-2-yl}-1H-indole-5-carboxamide hydrochloride;

3-(5-Cyanopyridin-2-yl)-2-hydroxy-N-(2-methoxyethyl)-1H-indole-5-carboxamide hydrochloride;

2-Hydroxy-3-[5-(piperidin-1-ylmethyl)pyridin-2-yl]-1H-indole-5-carboxamide hydrochloride;

2-Hydroxy-N-methyl-3-[5-(morpholin-4-ylmethyl)pyridin-2-yl]-1H-indole-5-carboxamide hydrochloride;

6-Bromo-2-hydroxy-N-methyl-3-{5-[(4-methylpiperazin-1-yl)sulfonyl]pyridin-2-yl}-1H-indole-5-carboxamide hydrochloride;

6-Bromo-2-hydroxy-N-isopropyl-3-{5-[(4-methylpiperazin-1-yl)sulfonyl]pyridin-2-yl}-1H-indole-5-carboxamide hydrochloride;

6-Bromo-2-hydroxy-N-(2-methoxyethyl)-3-{5-[(4-methylpiperazin-1-yl)sulfonyl]pyridin-2-yl}-1H-indole-5-carboxamide hydrochloride;

6-Bromo-2-hydroxy-3-{5-[(4-methylpiperazin-1-yl)sulfonyl]pyridin-2-yl}-N-(tetrahydrofuran-2-ylmethyl)-1H-indole-5-carboxamide hydrochloride;

6-Bromo-2-hydroxy-3-{5-[(4-methylpiperazin-1-yl)sulfonyl]pyridin-2-yl}-N-(2-pyrrolidin-1-ylethyl)-1H-indole-5-carboxamide hydrochloride;

N-[3-(Dimethylamino)propyl]-2-hydroxy-3-{5-[(4-methylpiperazin-1-yl)sulfonyl]pyridin-2-yl}-1H-indole-5-carboxamide hydrochloride;

2-Hydroxy-N-(2-methoxyethyl)-3-[5-(morpholin-4-ylsulfonyl)pyridin-2-yl]-1H-indole-5-carboxamide hydrochloride;

2-Hydroxy-3-{5-[(4-methylpiperazin-1-yl)sulfonyl]pyridin-2-yl}-N-pyridin-3-yl-1H-indole-5-carboxamide hydrochloride;

2-Hydroxy-N-(2-methoxybenzylamine)-3-{5-[(4-methylpiperazin-1-yl)sulfon]pyridin-2-yl}-1H-indole-5-carboxamide hydrochloride;

2-Hydroxy-N-(3-methoxybenzylamine)-3-{5-[(4-methylpiperazin-1-yl)sulfon]pyridin-2-yl}-1H-indole-5-carboxamide hydrochloride;

2-Hydroxy-3-{5-[(4-methylpiperazin-1-yl)sulfon]pyridin-2-yl}-N-(tetrahydro-2H-pyran-4-yl)-1H-indole-5-carboxamide hydrochloride;

2-Hydroxy-N-(4-methoxybenzylamine)-3-{5-[(4-methylpiperazin-1-yl)sulfon]pyridin-2-yl}-1H-indole-5-carboxamide hydrochloride;

N-(Cyanomethyl)-2-hydroxy-3-[5-(morpholin-4-ylmethyl)pyridin-2-yl]-1H-indole-5-carboxamide hydrochloride;

N-(2-Furylmethyl)-2-hydroxy-3-[5-(morpholin-4-ylmethyl)pyridin-2-yl]-1H-indole-5-carboxamide hydrochloride;

2-Hydroxy-3-{5-[(4-methylpiperazin-1-yl)methyl]pyridin-2-yl}-1H-indole-6-carbonitrile hydrochloride;

2-Hydroxy-3-[5-(piperidin-1-ylmethyl)pyridin-2-yl]-1H-indole-6-carbonitrile hydrochloride;

2-Hydroxy-3-{5-[(3-oxopiperazin-1-yl)methyl]pyridin-2-yl}-1H-indole-6-carbonitrile hydrochloride;

2-Hydroxy-3-[6-(2-morpholin-4-ylethoxy)pyrimidin-4-yl]-1H-indole-6-carbonitrile hydrochloride;

3-{6-[2-(Diisopropylamino)ethoxy]pyrimidin-4-yl}-2-hydroxy-1H-indole-6-carbonitrile hydrochloride;

2-Hydroxy-3-{5-[(4-methylpiperazin-1-yl)sulfonyl]pyridin-2-yl}-1H-indole-5-carboxylic acid hydrochloride;

2-Hydroxy-3-{5-[(4-methylpiperazin-1-yl)sulfonyl]pyridin-2-yl}-N-[3-(2-oxopyrrolidin-1-yl)propyl]-1H-indole-5-carboxamide hydrochloride;

2-Hydroxy-3-{5-[(4-methylpiperazin-1-yl)sulfonyl]pyridin-2-yl}-N-(2-thienylmethyl)-1H-indole-5-carboxamide hydrochloride;

2-Hydroxy-3-{5-[(4-methylpiperazin-1-yl)sulfonyl]pyridin-2-yl}-N-[2-(2-oxoimidazolidin-1-yl)ethyl]-H-indole-5-carboxamide hydrochloride;

2-Hydroxy-3-{5-[(4-methylpiperazin-1-yl)sulfonyl]pyridin-2-yl}-N-[2-(2-thienyl)ethyl]-1H-indole-5-carboxamide hydrochloride;

N-[2-(Acetylamino)ethyl]-2-hydroxy-3-{5-[(4-methylpiperazin-1-yl)sulfonyl]pyridin-2-yl}-1H-indole-5-carboxamide hydrochloride;

N-(2-Cyanoethyl)-2-hydroxy-3-{5-[(4-methylpiperazin-1-yl)sulfonyl]pyridin-2-yl}-1H-indole-5-carboxamide hydrochloride;

N-[2-(Aminosulfonyl)ethyl]-2-hydroxy-3-{5-[(4-methylpiperazin-1-yl)sulfonyl]pyridin-2-yl}-1H-indole-5-carboxamide hydrochloride;

N-(Cyanomethyl)-2-hydroxy-3-{5-[(4-methylpiperazin-1-yl)sulfonyl]pyridin-2-yl}-1H-indole-5-carboxamide hydrochloride;

2-Hydroxy-3-[5-(4-methylpiperazine-1-sulfonyl)pyridin-2-yl]-1H-indole-5-carboxylic acid carbamoylmethylamide hydrochloride;

2-Hydroxy-3-{5-[(4-methylpiperazin-1-yl)sulfonyl]pyridin-2-yl}-N-[2-(methylsulfonyl)ethyl]-1H-indole-5-carboxamide hydrochloride;

Methyl 3-fluoro-3-[5-(morpholin-4-ylmethyl)pyridin-2-yl]-2-oxoindoline-5-carboxylate hydrochloride;

3-(5-Diethylaminomethyl-pyridin-2-yl)-2-hydroxy-1H-indole-5-carboxylic acid (2-methanesulfonyl-ethyl)-amide hydrochloride;

as a free base or another salt than hydrochloride, or a tautomer thereof;

2-Hydroxy-3-{5-[(4-methylpiperazin-1-yl)sulfonyl]pyridin-2-yl}-1H-indole-5-carbonitrile;
3-(4-Cyanopyridin-2-yl)-2-hydroxy-N-(2-methoxyethyl)-1H-indole-5-carboxamide;
2-Hydroxy-3-[5-(4-methylpiperazine-1-sulfonyl)pyridin-2-yl]-1H-indole-5-carboxylic acid (2-carbamoylethyl) amide;
2-Hydroxy-3-[5-(4-methyl-piperazin-1-ylmethyl)-pyridin-2-yl]-1H-indole-5-carboxylic acid methyl ester;
2-Hydroxy-3-[5-(4-methyl-piperazin-1-ylmethyl)-pyridin-2-yl]-1H-indole-5-carboxylic acid (thiophen-2-ylmethyl)-amide dihydrochloride;
2-Hydroxy-3-[5-(4-methyl-piperazin-1-ylmethyl)-pyridin-2-yl]-1H-indole-5-carboxylic acid benzylamide dihydrochloride;

as a free base or a salt, or a tautomer thereof.

In yet another aspect of the invention the above listed compounds are in the form of a pharmaceutically acceptable salt.

In yet another aspect of the invention the following compounds, which are useful as intermediates in the preparation of compounds of formula I, are provided:
6-Chloronicotinic acid 1-oxide;
Ethyl 6-chloronicotinate 1-oxide;
1-[(6-Chloro-1-oxidopyridin-3-yl)carbonyl]-4-methylpiperazine;
tert-Butyl 4-[(6-chloropyridin-3-yl)sulfonyl]piperazine-1-carboxylate;
(2-{4-[(6-Chloropyridin-3-yl)sulfonyl]piperazin-1-yl}ethyl) dipropylamine;
4-(2-{4-[(6-Chloropyridin-3-yl)sulfonyl]piperazin-1-yl}ethyl)morpholine;
1-[(6-Chloropyridin-3-yl)sulfonyl]-4-(2-pyrrolidin-1-ylethyl)piperazine;
1-[(6-Chloropyridin-3-yl)sulfonyl]-4-(2-methoxyethyl)piperazine;
6-Chloro-N-(2-pyrrolidin-1-ylethyl)pyridine-3-sulfonamide;
(2-{4-[(6-Chloropyridin-3-yl)sulfonyl]piperazin-1-yl}ethyl) dimethyl amine;
2-Oxo-N-(pyridin-2-ylmethyl)indoline-5-carboxamide;
2-Oxo-N-(2-thienylmethyl)indoline-5-carboxamide;
2-Oxo-N-[2-(2-oxoimidazolidin-1-yl)ethyl]indoline-5-carboxamide;
N-[2-(Acetylamino)ethyl]-2-oxoindoline-5-carboxamide;
N-(3-Methoxypropyl)-2-oxoindoline-5-carboxamide;
6-Bromo-N-isopropyl-2-oxoindoline-5-carboxamide;
6-Bromo-N-(2-methoxyethyl)-2-oxoindoline-5-carboxamide;
6-Bromo-2-oxo-N-(tetrahydrofuran-2-ylmethyl)indoline-5-carboxamide;
6-Bromo-2-oxo-N-(2-pyrrolidin-1-ylethyl)indoline-5-carboxamide;
N-[3-(Dimethylamino)propyl]-2-oxoindoline-5-carboxamide;
N-(2-Methoxybenzyl)-2-oxoindoline-5-carboxamide;
N-(3-Methoxybenzyl)-2-oxoindoline-5-carboxamide;
N-(4-Methoxybenzyl)-2-oxoindoline-5-carboxamide;
2-Oxo-N-(tetrahydro-2H-pyran-4-yl)indoline-5-carboxamide;
N-Benzyl-2-oxoindoline-5-carboxamide;
N-(2-Methoxyethyl)-2-oxoindoline-5-carboxamide;
2-Oxo-N-propylindoline-5-carboxamide;
N-[2-(Dimethylamino)ethyl]-2-oxoindoline-5-carboxamide;
N-(2-Cyanoethyl)-2-oxoindoline-5-carboxamide;
4-[(6-Chloro-1-oxidopyridin-3-yl)methyl]morpholine;
4-[(6-Chloropyridin-3-yl)sulfonyl]morpholine;
N-[(6-Chloro-1-oxidopyridin-3-yl)methyl]-N-ethylethanamine;
1-[(6-Chloro-1-oxidopyridin-3-yl)methyl]-4-methylpiperazine;
1-[(6-chloro-1-oxidopyridine-3-yl)methyl]piperidine;
4-[(6-Chloro-1-oxidopyridin-3-yl)methyl]piperazin-2-one;
N-{2-[(4-Methylpiperazin-1-yl)sulfonyl]ethyl}-2-oxoindoline-5-carboxamide;
4-{2-[(6-Chloropyrimidin-4-yl)oxy]ethyl}morpholine;
N-{2-[(6-Chloropyrimidin-4-yl)oxy]ethyl}-N-isopropylpropan-2-amine;
Ethyl 6-(6-cyano-2-hydroxy-1H-indol-3-yl)nicotinate;
Methyl 2-hydroxy-3-[5-(morpholin-4-ylmethyl)pyridin-2-yl]-1H-indole-5-carboxylate;
Methyl 3-{5-[(diethylamino)methyl]pyridin-2-yl}-2-hydroxy-1H-indole-5-carboxylate;
Methyl 2-hydroxy-3-{5-[(4-methylpiperazin-1-yl)sulfonyl]pyridin-2-yl}-1H-indole-5-carboxylate;
2-Hydroxy-3-{5-[(4-methylpiperazin-1-yl)sulfonyl]pyridin-2-yl}-1H-indole-5-carboxylic acid;
Methyl 3-(4-cyanopyridin-2-yl)-2-hydroxy-1H-indole-5-carboxylate;

as a free base or a salt, or a tautomer thereof.

Listed below are definitions of various terms used in the specification and claims to describe the present invention.

For the avoidance of doubt it is to be understood that where in this specification a group is qualified by 'hereinbefore defined', 'defined hereinbefore' or 'defined above' the said group encompasses the first occurring and broadest definition as well as each and all of the other definitions for that group.

For the avoidance of doubt it is to be understood that in this specification '$C_{0-6}$' means a carbon group having 0, 1, 2, 3, 4, 5 or 6 carbon atoms.

For the avoidance of doubt it is to be understood that in this specification '$C_{1-6}$' means a carbon group having 1, 2, 3, 4, 5 or 6 carbon atoms.

In this specification, unless stated otherwise, the term "alkyl" includes both straight and branched chain alkyl groups and may be, but is not limited to, methyl, ethyl, n-propyl, i-propyl, n-butyl, i-butyl, s-butyl, t-butyl, n-pentyl, i-pentyl, t-pentyl, neo-pentyl, n-hexyl or i-hexyl, t-hexyl.

In this specification, unless stated otherwise, the term "cycloalkyl" refers to an optionally substituted, saturated cyclic hydrocarbon ring system. The term "$C_{3-6}$cycloalkyl" may be, but is not limited to, cyclopropyl, cyclobutyl, cyclopentyl or cyclohexyl.

In this specification, unless stated otherwise, the term "alkylaryl", includes both substituted and unsubstituted alkylaryl groups, which may be substituted on the alkyl and/or the aryl and may be, but are not limited to, $C_{1-6}$alkylaryl, benzyl or ethylphenyl.

In this specification, unless stated otherwise, the term "heteroaryl" may be a monocyclic heteroaromatic, or a bicyclic fused-ring heteroaromatic group. Examples of said heteroaryl include, but are not limited to, pyridyl, pyrrolyl, furyl, thienyl, imidazolyl, oxazolyl, isoxazolyl, thiazolyl, pyrazolyl, benzofuryl, indolyl, isoindolyl, benzimidazolyl, pyridazinyl, pyrimidinyl, pyrazinyl, tetrazolyl and triazolyl.

In this specification, unless stated otherwise, the term "5- or 6-membered heteroaromatic ring containing one or two heteroatoms selected independently from N, O and S of which at least one atom is selected from nitrogen" includes, but is not limited to, isoxazolyl, isothiazolyl, oxazolyl, pyrazinyl, pyrazolyl, pyridazinyl, pyridyl, pyrimidyl, pyrrolyl, thiazolyl, imidazolyl.

In this specification, unless stated otherwise, the terms "$C_{3-6}$heterocyclic group", "5- or 6-membered heterocyclic group containing one or more heteroatoms, selected independently from N, O and S" or "4-, 5-, 6- or 7-membered heterocyclic group containing one or more heteroatoms selected independently from N, O and S" may be, but are not limited to, azepanyl, azitidinyl, imidazolidinyl, imidazolinyl, morpholinyl, piperazinyl, piperidyl, piperidonyl, pyrazolidinyl, pyrazolinyl, pyrrolidinyl, pyrrolinyl, tetrahydrofuranyl, tetrahydropyranyl, thiomorpholinyl.

In the case where a subscript is the integer 0 (zero) the group to which the subscript refers to, indicates that the group is absent, i.e. there is a direct bond between the groups.

In this specification, unless stated otherwise, the term halogen may be fluorine, chlorine, bromine or iodine.

The present invention relates to the use of a compound of formula Ia or Ib as hereinbefore defined as well as to the salts thereof. Salts for use in pharmaceutical compositions will be pharmaceutically acceptable salts, but other salts may be useful in the production of the compound of formula Ia or Ib.

Both organic and inorganic acids can be employed to form non-toxic pharmaceutically acceptable salts of the compounds of this invention. Pharmaceutically acceptable salts include, but are not limited to hydrochloride, and fumarate. These salts are readily prepared by methods known in the art.

Some compounds of formula Ia or Ib may have chiral centres and/or geometric isomeric centres (E- and Z-isomers), and it is to be understood that the invention encompasses all such optical, diastereoisomeric and geometric isomers.

Within the present invention it is to be understood that a compound of formula Ia or Ib or a salt thereof may exhibit the phenomenon of tautomerism as shown in FIG. 1 below. It is to be understood that the invention encompasses any tautomeric form of a compound of formula I and is not to be limited merely to any one tautomeric form utilized within the formula drawings:

Figure 1

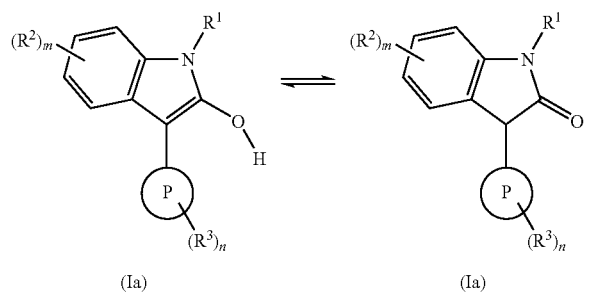

(Ia) (Ia)

wherein P, $R^1$, $R^2$, $R^3$, m and n are as defined above.

An object of the invention is to provide a compound of formula Ia or Ib for therapeutic use, especially compounds that are useful for the prevention and/or treatment of conditions associated with glycogen synthase kinase-3 (GSK3) in mammals including man. Particularly, a compound of formula Ia or Ib exhibiting a selective affinity for GSK-3.

Methods of Preparation

Another aspect of the present invention provides a process for preparing a compound of formula Ia or Ib as a free base or a salt thereof. Throughout the following description of such processes it is understood that, where appropriate, suitable protecting groups will be added to, and subsequently removed from the various reactants and intermediates in a manner that will be readily understood by one skilled in the art of organic synthesis. Conventional procedures for using such protecting groups as well as examples of suitable protecting groups are for example described in "Protective Groups in Organic Synthesis", T. W. Greene, P. G. M Wutz, Wiley-Interscience, New York, 1999.

Preparation of Intermediates

The process, wherein halo is halogen, $R^1$, $R^2$, $R^3$, $R^4$, $R^5$, $R^6$, $R^7$, $R^{10}$, $R^{11}$, n and m, unless otherwise specified, are as defined hereinbefore, comprises, (i) oxidation of a compound of formula II, wherein halo is halogen e.g. fluorine, chlorine or bromine and $R^4$ is $C_{1-6}$alkyl or hydrogen, to a compound of formula III may be carried out by

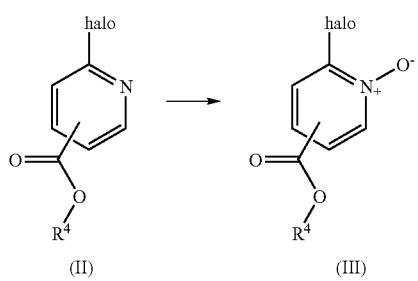

(II) (III)

the reaction with the appropriate reagent such as urea hydroperoxide complex and trifluoroacetic acid in a suitable solvent such as acetonitrile, dichloromethane or chloroform, or 3-chloroperbenzoic acid in a suitable solvent such as toluene, dichloromethane, chloroform or acetonitrile and the reaction may occur at a temperature between −20° C. and +80° C.

(ii) conversion of a compound of formula III, wherein halo is halogen e.g. fluorine, chlorine or bromine and $R^4$ is hydrogen, to a compound of formula IV may be carried out by

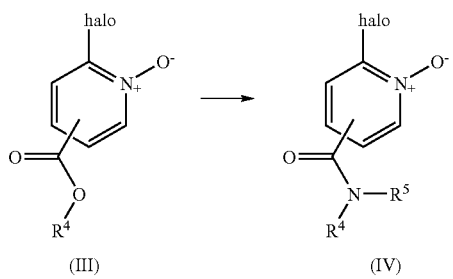

(III) (IV)

activation of the acid function in a compound of formula III, with a) a halogenation reagent such as thionyl chloride or oxalyl chlorid in a suitable solvent such as dichloromethane, chloroform or toluene or using the reagent neat and the reaction may occur at a temperature between 0° C. and +80° C., followed by the reaction with the appropriate amine $R^4R^5NH$ in a suitable solvent such as dichloromethane, chloroform, toluene or acetonitrile with or without a suitable base such as an alkali metal, an alkaline earth metal carbonate or hydroxide such as sodium carbonate, potassium carbonate, calcium carbonate, sodium hydroxide or potassium hydroxide or an alkylamine base such as triethylamine and the reaction may occur at a temperature between −20° C. and +80° C., or b) a suitable coupling reagent such as 1,3-diisopropylcarbodiimide, 1-[3-(dimethylamino)propyl]-3-ethylcarbodiimide hydrochloride, 1,3-dicyclohexylcarbodiimide, 2-ethoxy-1-ethoxycarbonyl-1,2-dihydroquinoline, O-(benzotriazol-1-yl)-N,N,N',N'-tetramethyluronium tetrafluoroborate, O-(benzotriazol-1-yl)-N,N,N',N'-tetramethyluronium hexafluorophosphate, 1,1'-carbonyldiimidazole or O-(7-azabenzotriazol-1-yl)-N,N,N',N'-tetramethyluronium hexafluorophosphate where the reaction may be aided by the addition of 1-hydroxybenzotriazole hydrate and optionally a suitable base such as N,N,-diisopropylethylamine and in a suitable solvent such as dichloromethane, N,N-dimethylformamide or tetrahydrofuran and the reaction may occur at a temperature between +20° C. and +130° C., followed by addition of the appropriate amine $R^4R^5NH$ and at a reaction temperature between +20° C. and +130° C.

(iii) conversion of a compound of formula V, wherein halo is halogen e.g. fluorine, chlorine or bromine, to a compound of formula VI may be carried out by

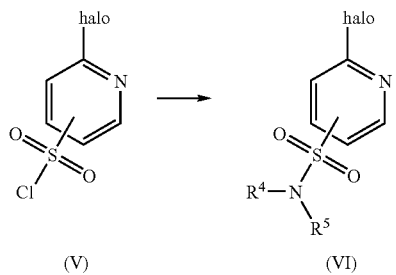

(V)    (VI)

the reaction with the appropriate amine $R^4R^5NH$ in a suitable solvent such as dichloromethane, chloroform, toluene or acetonitrile with or without a suitable base such as sodium carbonate, potassium carbonate, calcium carbonate, sodium hydroxide or potassium hydroxide or an alkylamine base such as triethylamine and the reaction may occur at a temperature between −20° C. and +80° C.

(iv) reaction of a compound of formula VII, wherein halo is halogen e.g. fluorine chlorine, bromine, to a compound of formula VIII may be carried out by

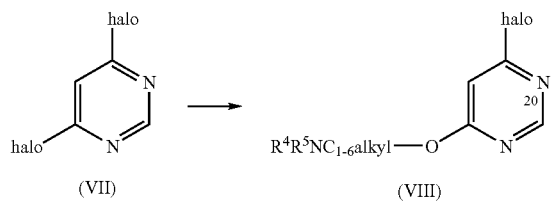

(VII)    (VIII)

the reaction with an appropriate reagent $R^4R^5NC_{2-6}alkylOH$ in a suitable solvent such as acetonitrile, dichloromethane, chloroform, toluene or N,N-dimethylformamide in the presence of a suitable base such as sodium carbonate, potassium carbonate, calcium carbonate, cesium carbonate, sodium hydroxide, potassium hydroxide or sodium hydride or an alkylamine base such as triethylamine and the reaction may occur at a temperature between 0° C. and +80° C.

(v) Conversion of a compound of formula IX, wherein halo is halogen e.g. fluorine, chlorine, bromine, to a compound of formula X may be carried out by

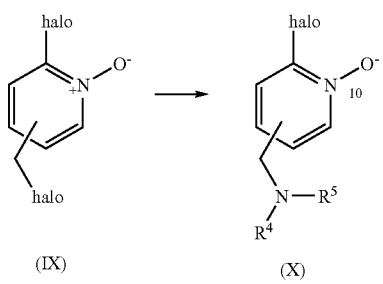

(IX)    (X)

reacting a compound of formula IX with an appropriate amine $R^4R^5NH$ in a suitable solvent such as dichloromethane, chloroform, acetonitrile or N,N-dimethylformamide with or without a suitable base such as sodium carbonate, potassium carbonate, calcium carbonate, sodium hydroxide or potassium hydroxide or, an alkylamine base such as triethylamine and the reaction may occur at a temperature between 0° C. and +120° C.

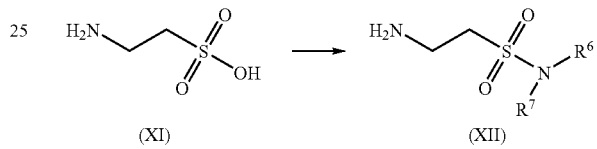

(XI)    (XII)

(vi) conversion of a compound of formula XI to a compound of formula XII may be carried out by the protection of the amino function in compound of formula XI with a suitable protecting group such as a benzyloxycarbonyl group followed by activation of the sulfonic acid function with a suitable halogenating reagent e.g. thionyl chloride or phosphorus oxychloride in a suitable solvent such as dichloromethane, chloroform, benzene or toluene, or using the reagent neat. The reaction may occur at a temperature between 0° C. and reflux.

The formed sulfonyl chloride may be reacted with the appropriate amine $HNR^6R^7$ in a suitable solvent such as dichloromethane, chloroform, toluene or benzene with or without a suitable base such as sodium carbonate, potassium carbonate, calcium carbonate, sodium hydroxide or an alkylamine base e.g. triethylamine and the reaction may occur at a temperature between −20° C. and +80° C. The protecting group is removed in a manner that will be readily understood by one skilled in the art of organic synthesis.

(vii) hydrolysis of a compound of formula XIII to obtain a compound of formula XIV,

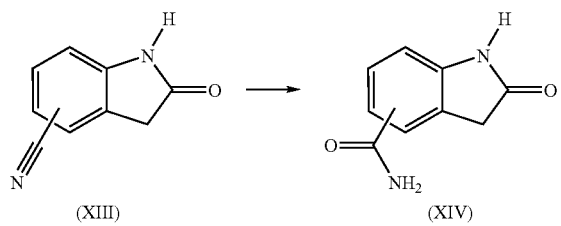

(XIII)    (XIV)

may be carried with a suitable hydrolyzing reagent such as an acid e.g. sulphuric acid at a reaction temperature between 0° C. and +100° C.

(viii) conversion of a compound of formula XV, wherein halo is as defined above, to obtain a compound of formula XVI,

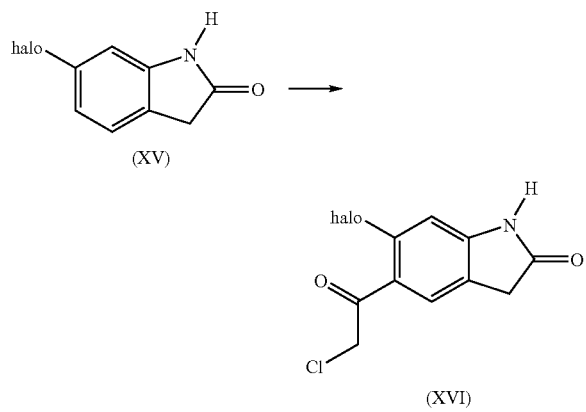

(XV)

(XVI)

may be carried out in a suitable solvent such as carbon disulfide, dichloromethane, 1,2-dichlorethane in the presence of suitable reagents such as aluminum trichloride and chloroacetyl chloride and at a reaction temperature between 0° C. and reflux.

(ix) conversion of a compound of formula XVI, wherein halo is as defined above, to obtain a compound of formula XVII,

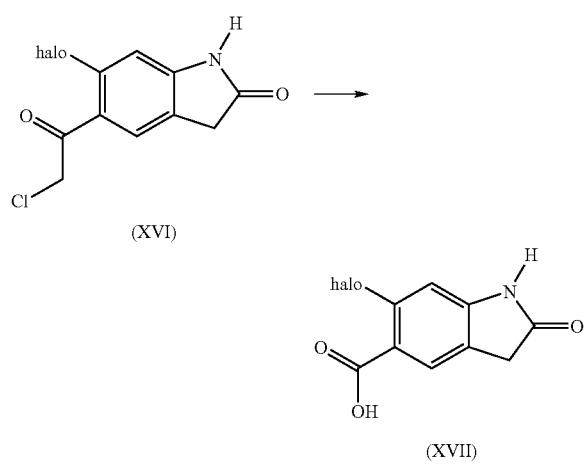

(XVI)

(XVII)

may be carried out in a suitable solvent such as pyridine in the presence of a suitable base such as sodium hydroxide or potassium hydroxide and at a reaction temperature between 25° C. and 90° C.

(x) amidation of a compound of formula XVII, wherein $R^2$ is halo or hydrogen, to obtain a compound of formula XVIII,

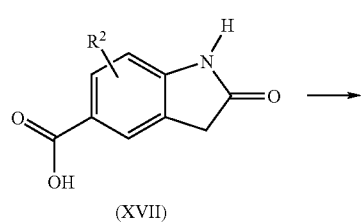

(XVII)

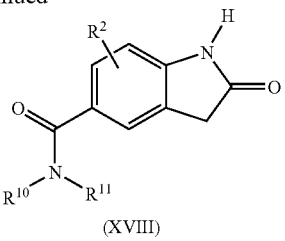

(XVIII)

may be carried by activation of the acid function in a compound of formula XVII, with a) a halogenation reagent such as thionyl chloride or oxalyl chloride in a suitable solvent such as dichloromethane, chloroform or toluene or using the reagent neat and the reaction may occur at a temperature between 0° C. and +80° C., followed by the reaction with the appropriate amine $R^{10}R^{11}NH$, e.g. compound of formula XII, in a suitable solvent such as dichloromethane, chloroform, toluene or acetonitrile with or without a suitable base such as an alkali metal, an alkaline earth metal carbonate or hydroxide such as sodium carbonate, potassium carbonate, calcium carbonate, sodium hydroxide or potassium hydroxide or an alkylamine base such as triethylamine and the reaction may occur at a temperature between −20° C. and +80° C., or b) a suitable coupling reagent such as 1,3-diisopropylcarbodiimide, 1-[3-(dimethylamino)propyl]-3-ethylcarbodiimide hydrochloride, 1,3-dicyclohexylcarbodiimide, 2-ethoxy-1-ethoxycarbonyl-1,2-dihydroquinoline, O-(benzotriazol-1-yl)-N,N,N',N'-tetramethyluronium tetrafluoroborate, O-(benzotriazol-1-yl)-N,N,N',N'-tetramethyluronium hexafluorophosphate, 1,1'-carbonyldiimidazole or O-(7-azabenzotriazol-1-yl)-N,N,N',N'-tetramethyluronium hexafluorophosphate where the reaction may be aided by the addition of 1-hydroxybenzotriazole hydrate and optionally a suitable base such as N,N,-diisopropylethylamine and in a suitable solvent such as acetonitril, dichloromethane, N,N-dimethylformamide or tetrahydrofuran or mixtures thereof and the reaction may occur at a temperature between +20° C. and +130° C., followed by addition of the appropriate amine $R^{10}R^{11}NH$, e.g. compound of formula XII, and at a reaction temperature between +20° C. and +130° C.

(xi) reacting a compound of formula II or III, wherein $R^4$ is $C_{1-6}$alkyl and halo is a halogen, e.g. fluorine, chlorine or bromine, with a compound of formula D (e.g. compounds of formula XIV and XVIII) to form a compound of formula XIX,

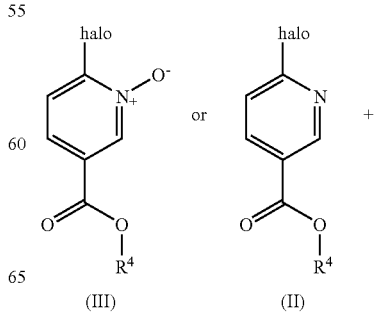

(III) or (II) +

-continued

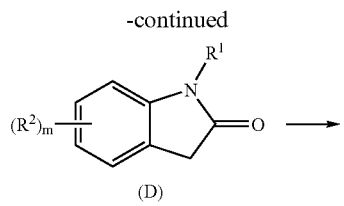

(D)

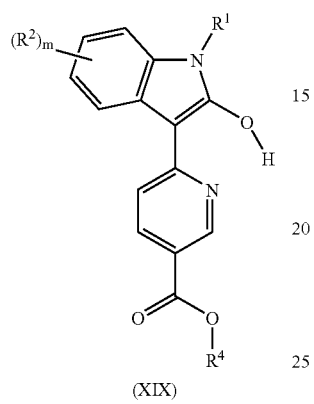

(XIX)

may be carried out in an appropriate solvent such as an ether e.g. tetrahydrofuran or 1,4-dioxan, an aromatic hydrocarbon solvent such as toluene or a dipolar aprotic solvent such as N,N-dimethylformamide, N,N-dimethylacetamide, N-methylpyrrolidin-2-one or dimethylsulphoxide and the reaction may occur at a temperature between +10° C. and +150° C.

The reaction is advantageously effected in the presence of a base. A suitable base may be an organic amine base such as pyridine, 2,6-lutidine, collidine, 4-dimethylaminopyridine, triethylamine, morpholine, N-methylmorpholine, diazabicyclo[5.4.0]undec-7-ene, tetramethylguanidine or an alkali metal or an alkaline earth metal carbonate or hydroxide such as sodium carbonate, potassium carbonate, calcium carbonate, sodium hydroxide or potassium hydroxide. Alternatively, such a base may be an alkali metal hydride such as sodium hydride, or an alkali metal or alkaline earth metal amide such as sodium amide, sodium bis(trimethylsilyl)amide, potassium amide or potassium bis(trimethylsilyl)amide. The N-oxide may be reduced by using a suitable reagent such as phosphorus trichloride in a suitable solvent such as dichloromethane, chloroform, toluene or ethyl acetate or mixtures thereof and the reaction may occur at a temperature between 0° C. and +100° C.

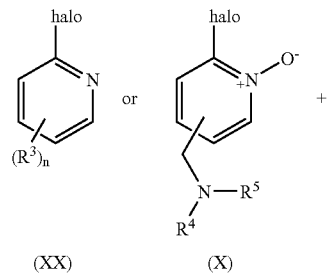

(XX)           (X)

-continued

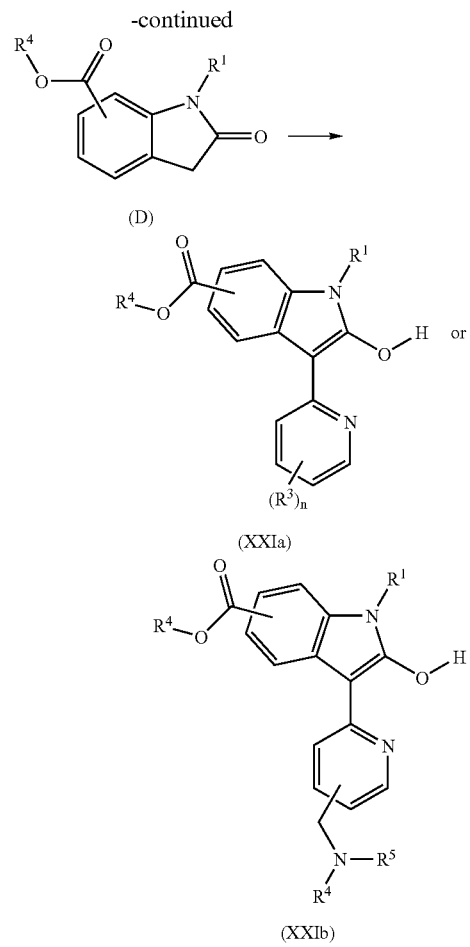

(XXIa)

(XXIb)

(xii) reacting a compound of formula XX or X, wherein halo is a halogen, e.g. fluorine, chlorine or bromine, with a compound of formula D, wherein $R^4$ is $C_{1-6}$alkyl, to form a compound of formula XXIa or, XXIb may be carried out in an appropriate solvent such as an ether e.g. tetrahydrofuran or 1,4-dioxan, an aromatic hydrocarbon solvent such as toluene or a dipolar aprotic solvent such as N,N-dimethylformamide, N,N-dimethylacetamide, N-methylpyrrolidin-2-one or dimethylsulphoxide and the reaction may occur at a temperature between +10° C. and +150° C.

The reaction is advantageously effected in the presence of a base. A suitable base may be an organic amine base such as pyridine, 2,6-lutidine, collidine, 4-dimethylaminopyridine, triethyl amine, morpholine, N-methylmorpholine, diazabicyclo[5.4.0]undec-7-ene, tetramethylguanidine or an alkali metal or an alkaline earth metal carbonate or hydroxide such as sodium carbonate, potassium carbonate, calcium carbonate, sodium hydroxide or potassium hydroxide. Alternatively, such a base may be an alkali metal hydride such as sodium hydride, or an alkali metal or alkaline earth metal amide such as sodium amide, sodium bis(trimethylsilyl)amide, potassium amide or potassium bis(trimethylsilyl)amide. The N-oxide may be reduced by using a suitable reagent such as phosphorus trichloride in a suitable solvent such as dichloromethane, chloroform, toluene or ethyl acetate or mixtures thereof and the reaction may occur at a temperature between 0° C. and +100° C.

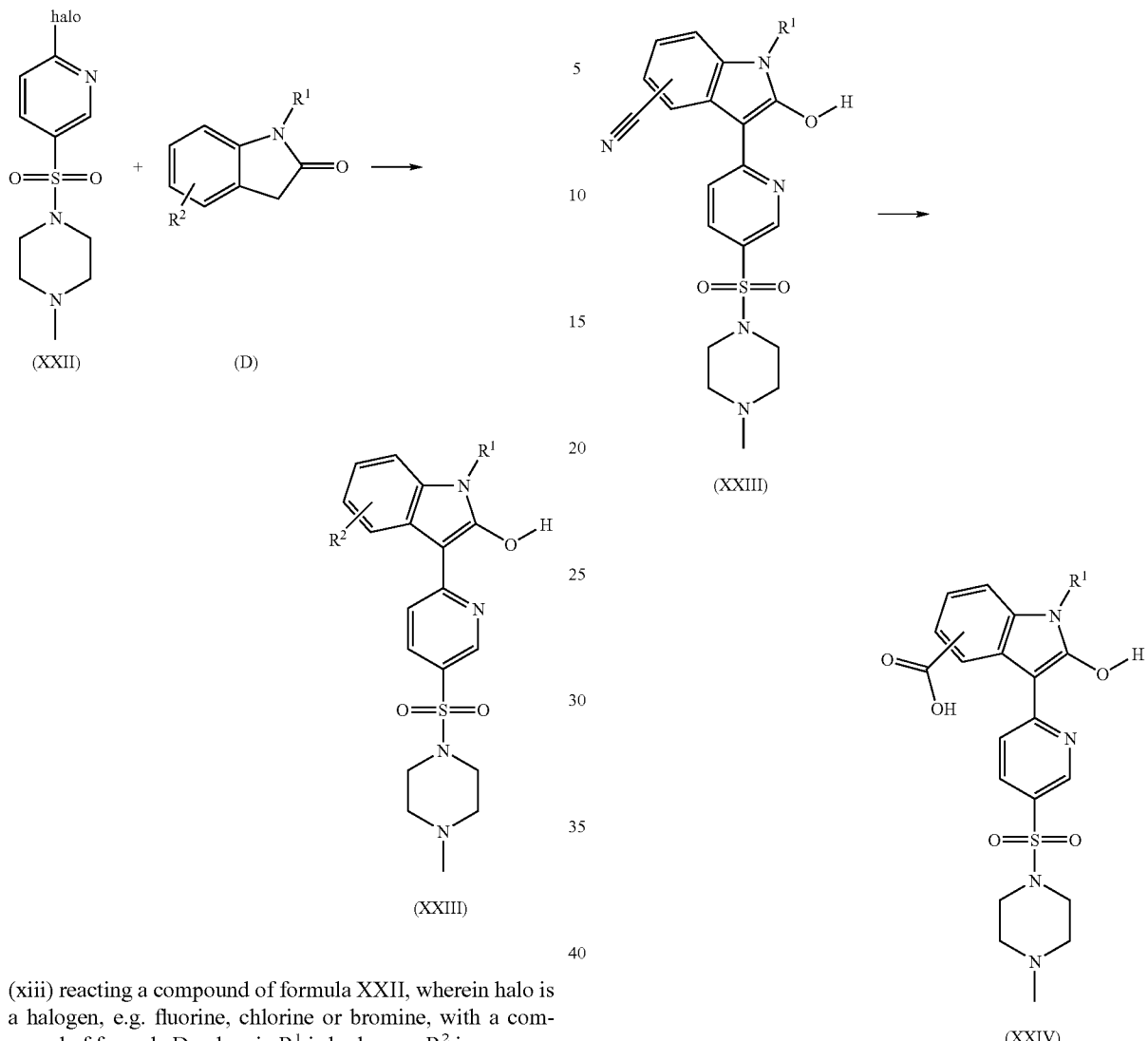

(xiii) reacting a compound of formula XXII, wherein halo is a halogen, e.g. fluorine, chlorine or bromine, with a compound of formula D, wherein $R^1$ is hydrogen, $R^2$ is cyano or $(CO)OR^4$ and $R^4$ is $C_{1-6}$alkyl, to form a compound of formula XXIII, may be carried out in an appropriate solvent such as an ether e.g. tetrahydrofuran or 1,4-dioxan, an aromatic hydrocarbon solvent such as toluene or a dipolar aprotic solvent such as N,N-dimethylformamide, N,N-dimethylacetamide, N-methylpyrrolidin-2-one or dimethylsulphoxide and the reaction may occur at a temperature between +10° C. and +150° C.

The reaction is advantageously effected in the presence of a base. A suitable base may be an organic amine base such as pyridine, 2,6-lutidine, collidine, 4-dimethylaminopyridine, triethylamine, morpholine, N-methylmorpholine, diazabicyclo[5.4.0]undec-7-ene, tetramethylguanidine or an alkali metal or an alkaline earth metal carbonate or hydroxide such as sodium carbonate, potassium carbonate, calcium carbonate, sodium hydroxide or potassium hydroxide. Alternatively, such a base may be an alkali metal hydride such as sodium hydride, or an alkali metal or alkaline earth metal amide such as sodium amide, sodium bis(trimethylsilyl)amide, potassium amide or potassium bis(trimethylsilyl)amide.

(xiv) converting a compound of formula XXIII, wherein $R^1$ is hydrogen, to a compound of formula XXIV, may be carried out in an appropriate solvent such as water and a suitable base such as sodium hydroxide or potassium hydroxide and the reaction may occur at a temperature between +10° C. and +150° C., e.g. under micro wave irradiation.

Methods of Preparation of End Products

Another object of the invention are processes a, b, c, d, e and f for the preparation of a compound of general formula Ia or Ib, wherein halo is halogen, P, $R^1$, $R^2$, $R^3$, $R^4$, $R^5$, $R^{10}$, $R^{11}$ m and n, unless otherwise specified, are defined as hereinbefore, and salts thereof.

These processes comprise:

a) reacting a compound of formula A (e.g. compound of formula VI, VIII), wherein $L^1$ is a leaving group such as halogen, e.g. fluorine, chlorine or bromine, with a compound of formula D (e.g. compounds of formula XIV, XVIII) to form a compound of formula Ia;

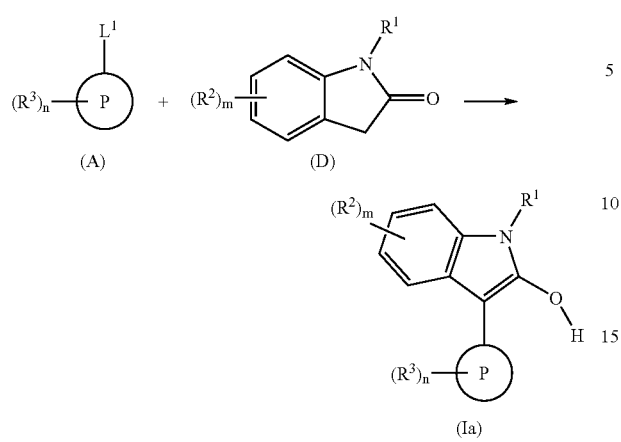

The reaction of process a may be carried out in an appropriate solvent such as an ether e.g. tetrahydrofuran or 1,4-dioxan, an aromatic hydrocarbon solvent such as toluene or a dipolar aprotic solvent such as N,N-dimethylformamide, N,N-dimethylacetamide, N-methylpyrrolidin-2-one or dimethylsulphoxide and the reaction may occur at a temperature between +10° C. and +150° C.

The reaction is advantageously effected in the presence of a base. A suitable base may be an organic amine base such as pyridine, 2,6-lutidine, collidine, 4-dimethylaminopyridine, triethylamine, morpholine, N-methylmorpholine, diazabicyclo[5.4.0]undec-7-ene, tetramethylguanidine or an alkali metal or an alkaline earth metal carbonate or hydroxide such as sodium carbonate, potassium carbonate, calcium carbonate, sodium hydroxide or potassium hydroxide. Alternatively, such a base may be an alkali metal hydride such as sodium hydride, or an alkali metal or alkaline earth metal amide such as sodium amide, sodium bis(trimethylsilyl)amide, potassium amide or potassium bis(trimethylsilyl)amide.

When it is desired to obtain the acid salt, the free base may be treated with an acid such as a hydrogen halide such as hydrogen chloride or, a carboxylic acid such as fumaric acid in a suitable solvent such as tetrahydrofuran, diethyl ether, methanol, ethanol, chloroform or dichloromethane or mixtures thereof, the reaction may occur between −30° C. to +50° C.

Consequently, there is provided a process for the preparation of a compound of formula Ia as defined above, wherein P, $R^1$, $R^2$ and $R^3$, m and n, unless otherwise specified, are defined above, comprising reacting a compound of formula A, wherein $L^1$ is a leaving group, with a compound of formula D to form a compound of formula Ia;

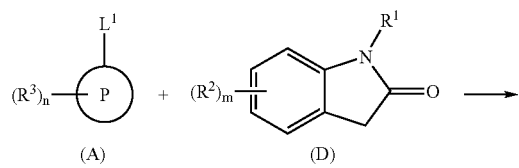

-continued

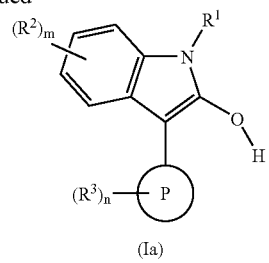

said reaction being carried out in an appropriate solvent at a temperature between +10° C. and +150° C.

b) reacting a compound of formula B (e.g. compounds of formula IV, X), wherein halo is halogen, e.g. fluorine, chlorine or bromine with a compound of formula D (e.g. compounds of formula XIV, XVIII) to form a compound of formula Ia;

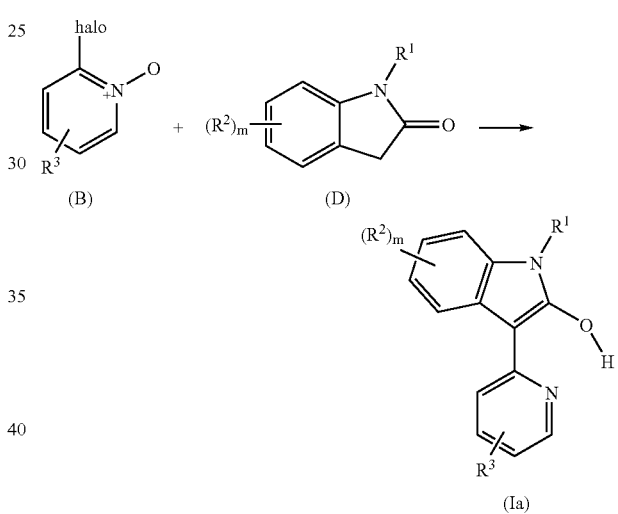

The reaction of process b may be carried out in an appropriate solvent such as an ether e.g. tetrahydrofuran or 1,4-dioxan, an aromatic hydrocarbon solvent such as toluene, or a dipolar aprotic solvent such as N,N-dimethylformamide, N,N-dimethylacetamide, N-methylpyrrolidin-2-one or dimethylsulphoxide, the reaction may occur at a temperature between +10° C. and +150° C.

The reaction is advantageously effected in the presence of a base. Such a base may be an organic amine base such as pyridine, 2,6-lutidine, collidine, 4-dimethylaminopyridine, triethylamine, morpholine, N-methylmorpholine, diazabicyclo[5.4.0]undec-7-ene, tetramethylguanidine or an alkali metal or an alkaline earth metal carbonate or hydroxide such as sodium carbonate, potassium carbonate, calcium carbonate, sodium hydroxide or potassium hydroxide. Alternatively, such a base may be an alkali metal hydride such as sodium hydride, an alkali metal or an alkaline earth metal amide such as sodium amide, sodium bis(trimethylsilyl)amide, potassium amide or potassium bis(trimethylsilyl)amide. The N-oxide may be reduced by using a suitable reagent such as phosphorus trichloride in a suitable solvent such as dichloromethane, chloroform, toluene or ethyl acetate or mixtures thereof and the reaction may occur at a temperature between 0° C. and +100° C.

When it is desired to obtain the acid salt, the free base may be treated with an acid such as a hydrogen halide such as hydrogen chloride, or a carboxylic acid such as fumaric acid in a suitable solvent such as tetrahydrofuran, diethyl ether, methanol, ethanol, chloroform or dichloromethane or mixtures thereof, the reaction may occur between –30° C. to +50° C.

Consequently, there is provided a process for the preparation of a compound of formula Ia as defined above, wherein $R^1$, $R^2$ and $R^3$ and m, is as defined above, and halo is halogen, unless otherwise specified, comprising reacting a compound of formula B with a compound of formula D to form a compound of formula Ia;

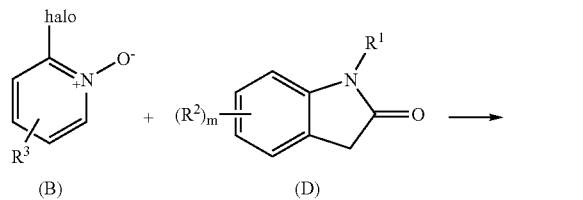

said reaction being carried out in an appropriate solvent at a temperature between +10° C. and +150° C.

c) reacting a compound of formula XIX, wherein $R^4$ is $C_{1-6}$alkyl, with the appropriate amine $HNR^4R^5$, to form a compound of formula Ia;

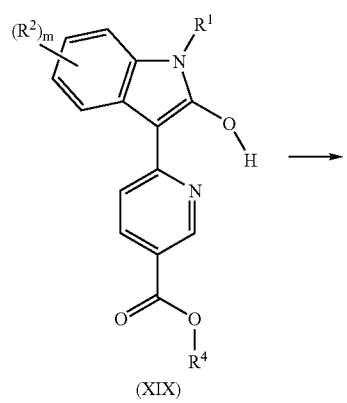

-continued

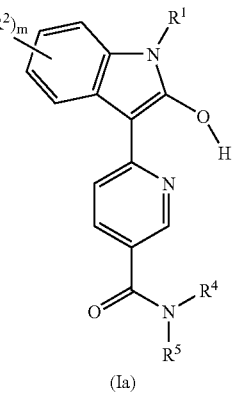

The reaction of process c may be carried out by:

i) the reaction of the compound of formula XIX with the appropriate amine $R^4R^5NH$ in a suitable solvent such as benzene, dichloromethane, chloroform, toluene or acetonitrile in the presence of a suitable reagent such as trimethylaluminum and at a reaction temperature between 0° C. and reflux or, ii) the reaction of the compound of formula XIX with the appropriate amine $R^4R^5NH$ neat or in a suitable solvent such as dichloromethane, chloroform, toluene or acetonitrile with or without a suitable base such as an alkali metal, an alkaline earth metal carbonate or hydroxide such as sodium carbonate, potassium carbonate, calcium carbonate, sodium hydroxide or potassium hydroxide or an alkyl aminebase such as triethylamine, and the reaction may occur at a temperature between –20° C. and +150° C.

When it is desired to obtain the acid salt, the free base may be treated with an acid such as a hydrogen halide such as hydrogen chloride, or a carboxylic acid such as fumaric acid in a suitable solvent such as tetrahydrofuran, diethyl ether, methanol, ethanol, chloroform or dichloromethane or mixtures thereof, the reaction may occur between –30° C. to +50° C.

Consequently, there is provided a process for the preparation of a compound of formula Ia as defined above, wherein $R^3$ is $CONR^4R^5$, comprising reacting a compound of formula XIX, wherein $R^4$ is $C_{1-6}$alkyl, with the appropriate amine $HNR^4R^5$, to form a compound of formula Ia;

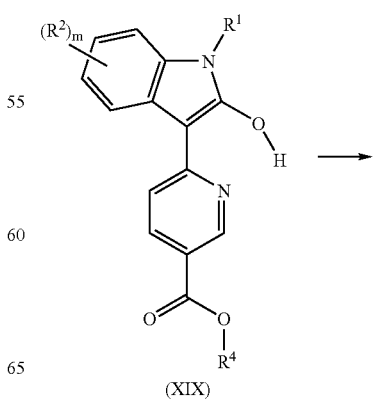

-continued

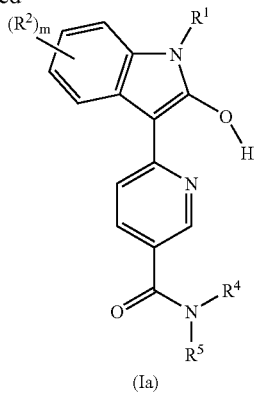

(Ia)

said reaction being carried out by;

i) reacting the compound of formula XIX with the appropriate amine $R^4R^5NH$ in a suitable solvent in the presence of a suitable reagent at a reaction temperature between 0° C. and reflux or;

ii) reacting the compound of formula XIX with the appropriate amine $R^4R^5NH$ neat or in a suitable solvent with or without a suitable base or an alkylamine base at a temperature between −20° C. and +150° C.

d) amidation of a compound of formula C (e.g compounds of formula XXIa, XXIb and XXIII), wherein $R^4$ is $C_{1-6}$alkyl, to form a compound of the formula Ia with the appropriate amine $HNR^{10}R^{11}$, may be carried out by

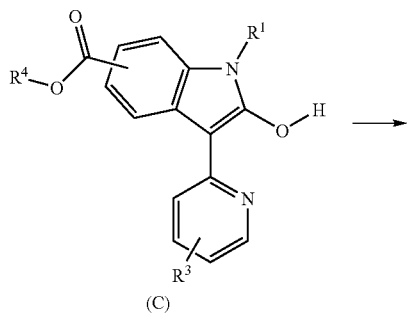

(C)

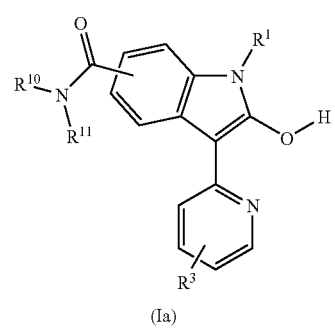

(Ia)

reaction with the appropriate amine $HNR^{10}R^{11}$ in a suitable solvent such as benzene, toluene, hexane, heptane, dichloromethane or chloroform in the presence of trimethyl aluminum and at a reaction temperature between −10° C. and reflux.

When it is desired to obtain the acid salt, the free base may be treated with an acid such as a hydrogen halide such as hydrogen chloride, or a carboxylic acid such as fumaric acid in a suitable solvent such as tetrahydrofuran, diethyl ether, methanol, ethanol, chloroform or dichloromethane or mixtures thereof, the reaction may occur between −30° C. to +50° C.

Consequently, there is provided a process for the preparation of a compound of formula Ia as defined above, wherein $R^2$ is $CONR^{10}R^{11}$, comprising amidation of a compound of formula C, wherein $R^4$ is $C_{1-6}$alkyl, to form a compound of the formula Ia;

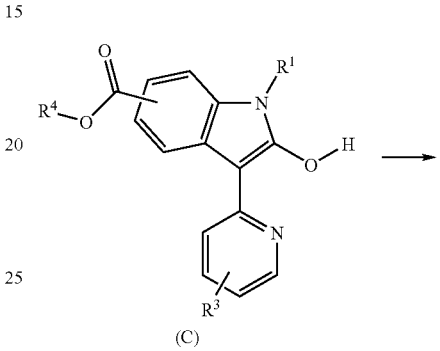

(C)

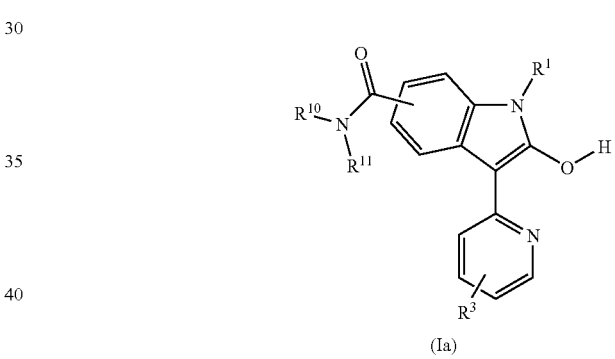

(Ia)

said reaction being carried out with the appropriate amine $HNR^{10}R^{11}$ in a suitable solvent in the presence of trimethyl aluminum and at a reaction temperature between −10° C. and reflux.

e) amidation of a compound of formula E (e.g. compound of formula XXIV), to form a compound of the formula Ia, with the appropriate amine $HNR^{10}R^{11}$, may be carried out by

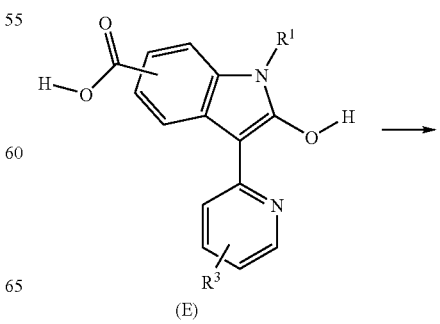

(E)

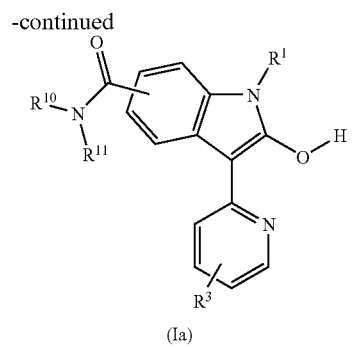

(Ia)

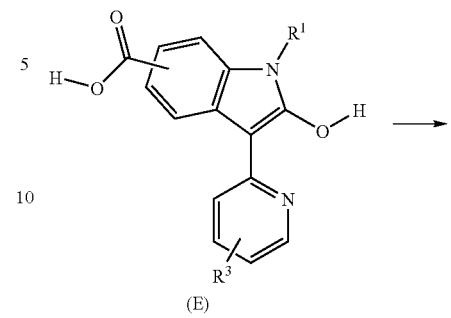

(E)

activation of the acid function in a compound of formula E (e.g compound of formula XXIV), with a) a halogenation reagent such as thionyl chloride or oxalyl chlorid in a suitable solvent such as methylene chloride, chloroform or toluene or using the reagent neat and the reaction may occur at a temperature between 0° C. and +80° C., followed by the reaction with the appropriate amine $HNR^{10}R^{11}$ in a suitable solvent such as methylene chloride, chloroform, toluene or acetonitrile with or without a suitable base such as an alkali metal, an alkaline earth metal carbonate or hydroxide such as sodium carbonate, potassium carbonate, calcium carbonate, sodium hydroxide or potassium hydroxide or an alkylamine base such as triethylamine and the reaction may occur at a temperature between −20° C. and +80° C., or b) a suitable coupling reagent such as 1,3-diisopropylcarbodiimide, 1-[3-(dimethylamino)propyl]-3-ethylcarbodiimide hydrochloride, 1,3-dicyclohexylcarbodiimide, 2-ethoxy-1-ethoxycarbonyl-1,2-dihydroquinoline, O-(benzotriazol-1-yl)-N,N,N',N'-tetramethyluronium tetrafluoroborate, O-(benzotriazol-1-yl)-N,N,N',N'-tetramethyluronium hexafluorophosphate, 1,1'-carbonyldiimidazole or O-(7-azabenzotriazol-1-yl)-N,N,N',N'-tetramethyluronium hexafluorophosphate where the reaction may be aided by the addition of 1-hydroxybenzotriazole hydrate and optionally a suitable base such as N,N,-diisopropylethylamine and in a suitable solvent such as methylene chloride, N,N-dimethylformamide or tetrahydrofuran and the reaction may occur at a temperature between +20° C. and +130° C., followed by addition of the appropriate amine $HNR^{10}R^{11}$ and at a reaction temperature between +20° C. and +130° C.

When it is desired to obtain the acid salt, the free base may be treated with an acid such as a hydrogen halide such as hydrogen chloride, or a carboxylic acid such as fumaric acid in a suitable solvent such as tetrahydrofuran, diethyl ether, methanol, ethanol, chloroform or dichloromethane or mixtures thereof, the reaction may occur between −30° C. to +50° C.

Consequently, there is provided a process for the preparation of a compound of formula Ia as defined above, wherein $R^2$ is $CONR^{10}R^{11}$, comprising amidation of a compound of formula E, to form a compound of the formula Ia, with the appropriate amine $HNR^{10}R^{11}$;

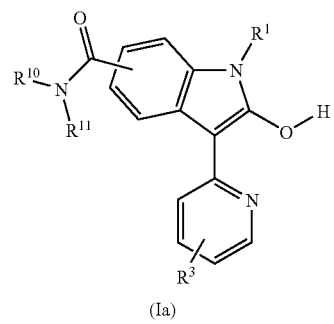

(Ia)

carried out by activation of the acid function in a compound of formula E with;

a) a halogenation reagent in a suitable solvent at a temperature between 0° C. and +80° C., followed by the reaction with the appropriate amine $HNR^{10}R^{11}$ in a suitable solvent with or without a suitable base at a temperature between −20° C. and +80° C., or;

b) a coupling reagent where the reaction is carried out in a suitable solvent at a temperature between +20° C. and +130° C., followed by addition of the appropriate amine $HNR^{10}R^{11}$.

f) fluorinating a compound of formula XXIa to form a compound of formula Ib.

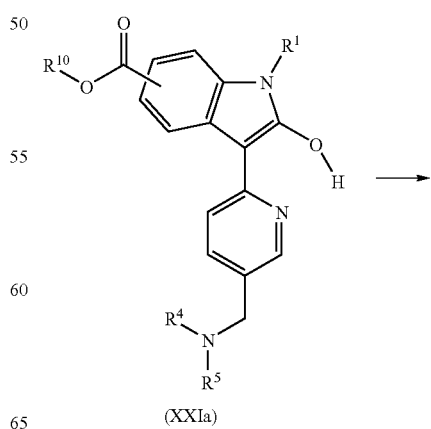

(XXIa)

-continued

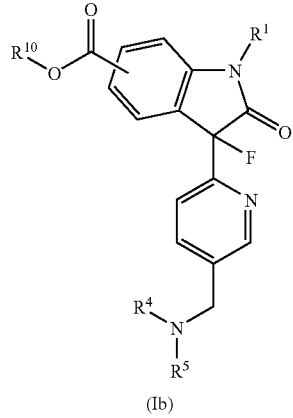

(Ib)

The reaction of process f may be carried out in an appropriate solvent such as an ether e.g. tetrahydrofuran or 1,4-dioxan or mixtures thereof in the presence of a suitable fluorinating reagent such as 1-fluoro-2,4,6-trimethylpyridinium triflate and a suitable base such as n-butyllithium or sodium bis(trimethylsilyl)amide and at a reaction temperature between −40° C. and +80° C.

When it is desired to obtain the acid salt, the free base may be treated with an acid such as a hydrogen halide such as hydrogen chloride, sulphuric acid, a sulphonic acid such as methane sulphonic acid or a carboxylic acid such as acetic or citric acid in a suitable solvent such as tetrahydrofuran, diethyl ether, methanol, ethanol, chloroform or methylene chloride or mixtures thereof, the reaction may occur between −30° C. to +50° C.

Consequently, there is provided a process for the preparation of a compound of formula Ia as defined above, wherein $R^3$ is $C_{1-6}$alkylNR$^4$R$^5$, comprising fluorinating a compound of formula XXIa to form a compound of formula Ib.

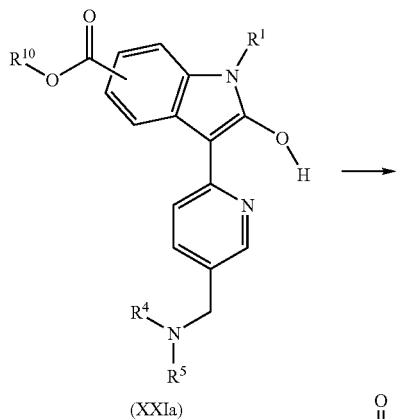

(XXIa)

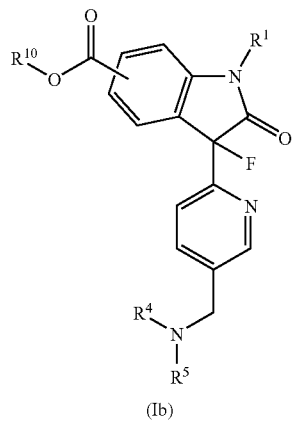

(Ib)

said reaction being carried out in an appropriate solvent in the presence of a suitable fluorinating reagent and a suitable base at a reaction temperature between −40° C. and +80° C.

Throughout the following description of such processes it is understood that, where appropriate, suitable protecting groups will be added to, and subsequently removed from, the various reactants and intermediates in a manner that will be readily understood by one skilled in the art of organic synthesis. Conventional procedures for using such protecting groups as well as examples of suitable protecting groups are described, for example, in "Protective Groups in Organic Synthesis" T. W. Green, P. G. M. Wuts, Wiley-Interscience, New York, 1999.

WORKING EXAMPLES

Example 1

6-Chloronicotinic acid 1-oxide m-Chloroperbenzoic acid (7.46 g, 26.0 mmol) was added to a suspension of 6-chloronicotinic acid (3.14 g, 20.0 mmol) in chloroform (30 mL) at room temperature. The mixture was stirred for 24 h at 45° C. followed by cooling to 0° C. The resulting white precipitate was filtered off, washed with chloroform (10 mL), and air-dried to give 3.22 g, (93% yield) of the title compound: $^1$H NMR (DMSO-d$_6$, 400 MHz) δ 8.72 (s, 1H), 7.97 (d, J=8.0 Hz, 1H), 7.78 (d, J=8.0 Hz, 1H); MS (EI) m/z 174 and 176 (M$^+$+1).

Example 2

Ethyl 6-chloronicotinate 1-oxide

Urea hydroperoxid complex (1.19 g, 12.6 mmol) was added to a stirred solution of ethyl 6-chloronicotinate (1.10 g, 6.0 mmol) in acetonitrile (15 mL) at room temperature. This mixture was stirred for 10 min at 0° C. followed by slow addition of an acetonitrile solution (5 mL) of trifluoroacetic anhydride (2.52 g, 12.0 mmol). After the addition the mixture was stirred for 2 h at room temperature. Thereafter, the reaction mixture was diluted with a saturated aqueous NaHCO$_3$ solution and extracted with dichloromethane. The organic phase was dried (Na$_2$SO$_4$) and concentrated to afford 0.98 g (81% yield) of the title compound as a white solid: $^1$H NMR (DMSO-d$_6$, 400 MHz) δ 8.94 (s, 1H), 7.81 (dd, J=8.4, 1.6 Hz, 1H), 7.60 (d, J=8.4 Hz, 1H), 4.43 (q, J=7.2 Hz, 2H), 1.40 (t, J=7.2 Hz, 3H); MS (EI) m/z 202 and 204 (M$^+$+1).

Example 3

1-[(6-Chloro-1-oxidopyridin-3-yl)carbonyl]-4-methylpiperazine

6-Chloronicotinic acid 1-oxide (0.347 g, 2.0 mmol) and 2-ethoxy-1-ethoxycarbonyl-1,2-dihydroquinoline (0.544 g, 2.2 mmol) were mixed in chloroform (8 mL) at 0° C. 1-Methylpiperazine (0.30 g, 3.0 mmol) was added after 5 min and the reaction mixture was stirred for 16 h at room temperature. The solvent was removed in vacuo and the residual oil was purified on a silica gel column using chloroform/methanol/triethylamine, (100:20:1), as the eluent to give 0.18 g, (35% yield) of the title compound as a brownish solid: $^1$H NMR (DMSO-d$_6$, 400 MHz) δ 8.56 (s, 1H), 7.90 (d, J=8.0 Hz, 1H), 7.39 (d, J=8.0 Hz, 1H), 3.63 (br s, 2H), 3.39 (br s, 2H), 2.43 (br s, 2H), 2.34 (br s, 2H), 2.25 (s, 3H); MS (EI) m/z 256 and 258 (M$^+$+1).

Example 4 tert-Butyl 4-[(6-chloropyridin-3-yl)sulfonyl]piperazine-1-carboxylate

6-Chloropyridine-3-sulfonyl chloride (0.318 g, 1.5 mmol; described in: Naegeli, C. et al. *Helv. Chim. Acta.* 1938, 21, 1746-1750) was added to a suspension of potassium carbonate (0.276 g, 2.0 mmol) in dichloromethane (3 mL) at room temperature. The mixture was stirred for 5 min at 0° C. followed by the addition of tert-butyl 1-piperazinecarboxylate (0.363 g, 2.0 mmol). The resulting reaction mixture was allowed to stir for 16 h at room temperature and the reaction mixture was filtered and the organic solution was concentrated in vacuo. The residue was purified an a silica gel column using heptane/ethyl acetate, (2:1), as the eluent to afford 0.188 g (35% yield) of the title compound as a white solid: $^1$H NMR (CDCl$_3$, 400 MHz) δ 8.74 (d, J=2.0 Hz, 1H), 7.96 (dd, J=8.4, 2.8 Hz, 1H), 7.51 (d, J=8.4 Hz, 1H), 3.53 (t, J=5.2 Hz, 4H), 3.03 (t, J=5.2 Hz, 4H), 1.42 (s, 9H); MS (EI) m/z 362 (M$^+$+1).

The following Examples, 5-9, were prepared as described for Example 4.

Example 5

(2-{4-[(6-Chloropyridin-3-yl)sulfonyl]piperazin-1-yl}ethyl)dipropylamine

Starting material: 1-(2-dipropylaminoethyl)piperazine (0.32 g, 1.5 mmol). Purification on a silica gel column using chloroform/methanol/triethylamine, (100:20:1), as the eluent gave 0.24 g (41% yield) of the title compound as a white solid: $^1$H NMR (CDCl$_3$, 400 MHz) δ 8.574 (d, J=2.4 Hz, 1H), 7.97 (dd, J=8.0, 2.4 Hz, 1H), 7.50 (d, J=8.0 Hz, 1H), 3.07 (br s, 4H), 2.58 (t, J=4.8 Hz, 4H), 2.48 (m, 4H), 2.34 (t, J=7.6 Hz, 4H), 1.41 (m, 4H), 0.84 (t, J=7.2 Hz, 6H); MS (EI) m/z 389 and 391 (M$^+$+1).

Example 6

4-(2-{4-[(6-Chloropyridin-3-yl)sulfonyl]piperazin-1-yl}ethyl)morpholine

Starting material: 4-(2-piperazin-1-ylethyl)morpholine (0.299 g, 1.5 mmol) in a dichloromethane/acetonitrile, (4:1), solvent mixture (3 mL). When the reaction was finished the white solid was filtered off, dissolved in methanol and filtered again. The organic solution was concentrated in vacuo to afford 0.541 g (96% yield) of the title compound: $^1$H NMR (DMSO-d$_6$, 400 MHz) δ 8.80 (s, 1H), 8.24 (d, J=8.0 Hz, 1H), 7.87 (d, J=8.0 Hz, 1H), 3.55 (br s, 4H), 3.36 (br s, 8H), 3.01 (br s, 4H), 2.37 (br s, 4H); MS (EI) m/z 375 and 377 (M$^+$+1).

Example 7

1-[(6-Chloropyridin-3-yl)sulfonyl]-4-(2-pyrrolidin-1-ylethyl)piperazine

Starting material: 1-(2-pyrrolidin-1-ylethyl)piperazine (0.275 g, 1.5 mmol). Yield: 78% of the title compound was obtained without chromatography: $^1$H NMR (CDCl$_3$, 400 MHz) δ 8.71 (d, J=2.4 Hz, 1H), 7.96 (dd, J=8.0, 2.4 Hz, 1H), 7.50 (d, J=8.0 Hz, 1H), 3.15 (br s, 6H), 3.00 (br s, 2H), 2.80 (m, 4H), 2.61 (t, J=4.8 Hz, 4H), 2.02 (m, 4H); MS (EI) m/z 359 and 361 (M$^+$+1).

Example 8

1-[(6-Chloropyridin-3-yl)sulfonyl]-4-(2-methoxyethyl)piperazine

Starting material: 1-(2-methoxyethyl)piperazine (0.216 g, 1.5 mmol). The white solid was filtered off. Yield 92%: $^1$H NMR (DMSO-d$_6$, 400 MHz) δ 8.80 (s, 1H), 8.25 (d, J=8.0 Hz, 1H), 7.88 (d, J=8.0 Hz, 1H), 3.47 (br s, 2H), 3.27 (s, 2H), 3.23 (s, 3H), 3.08 (br s, 2H), 3.01 (br s, 4H), 2.38 (br s, 2H); MS (EI) m/z 320 and 322 (M$^+$+1).

Example 9

6-Chloro-N-(2-pyrrolidin-1-ylethyl)pyridine-3-sulfonamide

Starting material: 2-pyrrolidin-1-ylethylamine. Purification on a silica gel column using ethyl acetate/triethylamine, (9:1), as the eluent gave the title compound in 58% yield: $^1$H NMR (CDCl$_3$, 400 MHz) δ 8.79 (d, J=2 Hz, 1H), 8.05 (dd, J=8, 3 Hz, 1H), 7.42 (d, J=9 Hz, 1H), 3.00 (app. t, J=6 Hz, 2H), 2.50 (app. t, J=6 Hz, 2H), 2.33 (m, 4H), 1.67 (m, 4H); $^{13}$C NMR (CDCl$_3$, 100 MHz) δ 155.7, 148.8, 137.8, 136.1, 125.0, 54.1, 53.9, 41.6, 23.9; MS (TSP) m/z 290 (M$^+$+1).

Example 10

(2-{4-[(6-Chloropyridin-3-yl)sulfonyl]piperazin-1-yl}ethyl)dimethylamine

To a solution of N,N-dimethyl-N-(2-piperazin-1-ylethyl)amine (0.80 g, 5.0 mmol) and triethylamine (1.0 g, 10 mmol) in dichloromethane (7 mL) was added 6-chloropyridine-3-sulfonyl chloride (1.0 g, 5.0 mmol; described in: Naegeli et al. *Helv. Chim. Acta,* 1938, 21, 1746, 1750) in dichloromethane (3 mL) at room temperature. After stirring over night at room temperature the solvent was removed in vacuo, the residue was partitioned between aqueous sodium hydroxide (2 M), diethyl ether (3×15 mL), and dichloromethane (3×15 mL). The combined extracts were dried (MgSO$_4$), and the solvents were removed in vacuo to afford 1.3 g of the crude product. The residue was purified on a silica gel column using acetonitrile/triethylamine, (90:10), as the eluent to afford 1.0 g (60% yield) of title compound: $^1$H NMR (CDCl$_3$, 400 MHz) δ 8.73 (d, J=2 Hz, 1H), 7.95 (dd, J=8, 2 Hz, 1H), 7.48 (d, J=8 Hz, 1H), 3.08 (t, J=5 Hz, 4H), 2.56 (t, J=5 Hz, 4H), 2.47 (t, J=7 Hz, 2H), 2.35 (t, J=7 Hz, 2H), 2.19 (s, 3H); $^{13}$C NMR (CDCl$_3$, 100 MHz) δ 155.8, 148.8, 137.8, 131.3, 124.6, 56.7, 56.0, 52.4, 45.8, 45.8.

Example 11

2-Oxo-N-(pyridin-2-ylmethyl)indoline-5-carboxamide

To a N,N-dimethylformamide/acetonitrile, (2 mL: 10 mL), mixture containing ethyldiisopropylamine (0.52 mL, 3 mmol) was added 2-oxoindoline-5-carboxylic acid (0.354 g, 2.0 mmol; described in: Sun L. et al. *J. Med. Chem.* 2000, 43(14), 2655:), O-(benzotriazol-1-yl)-N,N,N',N'-tetramethyluronium tetrafluoroborate (0.77 g, 2.4 mmol) and 1-hydroxybenzotriazole hydrate (0.324 g, 2.4 mmol) and stirred for 5 min at room temperature. Thereafter, 2-(aminomethyl)pyridine (0.562 g, 5.2 mmol) was added and the resulting reaction mixture was stirred for 90 min followed by addition of a saturated aqueous NaHCO$_3$ solution (10 mL). The solvents were removed in vacuo and 0.364 g (68% yield) of the title product was obtained as a white solid after purification on a silica gel column using chloroform/methanol, (9:1), as the eluent: $^1$H NMR (DMSO-d$_6$, 400 MHz) δ 10.66 (s, 1H), 8.96 (t, J=5.6 Hz, 1H), 8.55 (d, J=4.4 Hz, 1H), 7.85 (d, J=8.0 Hz, 1H), 7.83 (s, 1H), 7.78 (t, J=7.6 Hz, 1H), 7.34 (d, J=8.0 Hz, 1H), 7.29 (t, J=6.4 Hz, 1H), 6.92 (d, J=8.0 Hz, 1H), 4.59 (d, J=6.0 Hz, 2H), 3.58 (s, 2H); MS (EI) m/z 268 (M$^+$+1).

The following Examples, 12-15, were prepared as described for Example 11.

Example 12

2-Oxo-N-(2-thienylmethyl)indoline-5-carboxamide

Starting material: 2-(aminomethyl)thiophene. Purification on a silica gel column using chloroform/methanol, (9:1), as the eluent gave 0.208 g (76% yield) of the title compound: $^1$H NMR (DMSO-d$_6$, 400 MHz) δ 10.65 (s, 1H), 8.96 (t, J=5.6 Hz, 1H), 7.80 (d, J=7.6 Hz, 1H), 7.78 (s, 1H), 7.40 (t, J=4.0 Hz, 1H), 7.03 (br s, 1H), 6.99 (dd, J=4.8, 3.6 Hz, 1H), 6.90 (d, J=8.0 Hz, 1H), 4.64 (d, J=5.6 Hz, 2H), 3.57 (s, 2H); MS (EI m/z 273 (M$^+$+1).

Example 13

2-Oxo-N-[2-(2-oxoimidazolidin-1-yl)ethyl]indoline-5-carboxamide

Starting material: 1-(2-aminoethyl)imidazolidin-2-one (50% solution in isopropyl alcohol). Yield: 37%: $^1$H NMR (DMSO-d$_6$, 400 MHz) δ 10.63 (s, 1H), 8.38 (m, 1H), 7.75 (d, J=8.0 Hz, 1H), 7.73 (s, 1H), 6.89 (d, J=8.0 Hz, 1H), 6.31 (s, 1H), 3.56 (s, 2H), 3.43 (m, 4H), 3.24 (m, 4H); MS (EI) m/z 289 (M$^+$+1).

Example 14

N-[2-(Acetylamino)ethyl]-2-oxoindoline-5-carboxamide

Starting material: N-(2-aminoethyl)acetamide. The crude product was purified on a silica gel column using chloroform/methanol/triethylamine, (60:10:1), as the eluent, and was further purified by stirring in acetonitrile (3 mL) for 10 min followed by filtration and drying. Yield: 29% of a pink solid: $^1$H NMR (DMSO-d$_6$, 400 MHz) δ 10.63 (s, 1H), 8.36 (t, J=5.2 Hz, 1H), 7.98 (br s, 1H), 7.76 (d, J=7.6 Hz, 1H), 7.74 (s, 1H), 6.89 (d, J=8.0 Hz, 1H), 3.56 (s, 2H), 3.31 (m, 2H), 3.22 (m, 2H), 1.84 (s, 3H); MS (EI) m/z 262 (M$^+$+1).

Example 15

N-(3-Methoxypropyl)-2-oxoindoline-5-carboxamide

Starting material: 3-methoxypropylamine. Yield: 78% of a white solid: $^1$H NMR (CDCl$_3$, 400 MHz) δ 7.68 (s, 1H), 7.65 (d, J=8.0 Hz, 2H), 6.89 (d, J=8.0 Hz, 1H), 6.82 (br s, 1H), 3.58 (m, 6H), 3.39 (s, 3H), 1.89 (m, 2H); MS (EI) m/z 249 (M$^+$+1).

Example 16

2-Oxoindoline-5-carboxamide

A solution of 2-oxoindoline-5-carbonitrile (2.4 g, 15 mmol) in sulphuric acid (85%, 16 mL) was heated at 80° C. for 6 h and then allowed to reach room temperature over night. The mixture was poured into an ice/water mixture and the pH was adjusted to 5 with an aqueous sodium hydroxide solution (50%). The solid product was collected by filtration, washed with water, and dried in vacuo at 60° C. over night to afford 2.2 g (83% yield): $^1$H NMR (DMSO-d$_6$, 400 MHz) δ 10.63 (s, 1H), 7.88-7.72 (m, 3H), 7.23-7.11 (br s, 1H), 6.88 (d, J=8 Hz, 1H), 3.56 (s, 2H).

Example 17

2-Oxoindoline-6-carboxamide

The title compound was prepared as described for Example 16 using 2-oxoindoline-6-carbonitrile (1.2 g, 7.6 mmol) to afford 1.0 g (75% yield) of title compound: $^1$H NMR (DMSO-d$_6$, 400 MHz) δ 10.51 (s, 1H), 7.91 (br s, 1H), 7.46 (d, J=8 Hz, 1H), 7.31-7.22 (m, 3H), 3.51 (s, 2H).

Example 18

6-Bromo-5-(chloroacetyl)-1,3-dihydro-2H-indol-2-one

Chloroacetyl chloride (0.65 mL, 8.2 mmol) was added to a cooled (0° C.) suspension of 6-bromooxindol (0.825 g, 3.9 mmol) and aluminium chloride (1.82 g, 13.6 mmol) in 1,2-dichloroethane (8 mL). The resulting mixture was stirred at 0° C. for 20 min and at 50° C. for 17 h. The mixture was cooled to room temperature and was then poured on ice. The formed solid was filtered off, washed with water, and dried in vacuo to give 1.10 g (99% yield) of the title compound: $^1$H NMR (DMSO-d$_6$, 400 MHz) δ 7.69 (s, 1H), 7.09 (s, 1H), 4.97 (s, 2H), 3.52 (s, 2H).

Example 19

6-Bromo-2-oxoindoline-5-carboxylic acid

A mixture of 6-bromo-5-(chloroacetyl)-1,3-dihydro-2H-indol-2-one (1.11 g, 3.85 mmol) and pyridine (8.0 mL) was heated at 90° C. for 2.5 h. The formed precipitate was filtered is off and washed with ethanol. Aqueous sodium hydroxide (10.0 mL, 2.5 M) was added and the resulting mixture was heated at 80° C. for 2 h to give a dark red solution. The reaction mixture was acidified using aqueous hydrochloric acid (5.0 M). The dark red precipitate was filtered off, washed with hydrochloric acid (0.1 M), and dried in vacuo to give 0.742 g (75% yield) of the title compound: $^1$H NMR (DMSO-d$_6$, 400 MHz) δ 12.94 (br s, 1H), 10.69 (s, 1H), 7.66 (s, 1H), 7.04 (s, 1H), 3.49 (s, 2H); MS (ES) m/z 254 and 256 (M$^-$−1).

Example 20

6-Bromo-N-methyl-2-oxoindoline-5-carboxamide

Methylamine (0.75 mL, 2.0 M in tetrahydrofuran) was added to a stirred solution of 6-bromo-2-oxoindoline-5-carboxylic acid (0.246 g, 0.96 mmol), O-(benzotriazol-1-yl)-N,N,N',N'-tetramethyluronium tetrafluoroborate (0.369 g, 1.15 mmol), 1-hydroxybenzotriazole hydrate (0.176 g, 1.15 mmol), and diisopropylethylamine (0.55 mL, 3.16 mmol) in dry N,N-dimethylformamide (4 mL) under an atmosphere of nitrogen. The resulting mixture was stirred at room temperature for 1.5 h. An aqueous solution of sodium bicarbonate was added and the solvent was evaporated. The resulting residue was purified on a silica gel column using dichloromethane/methanol, (9:1), as the eluent to give 0.125 g (48% yield) of the title compound: $^1$H NMR (CD$_3$OD, 400 MHz) δ 7.27 (s, 1H), 7.11 (s, 1H), 3.20 (m, 2H), 3.09 (s, 3H); MS (ES) m/z 269 and 271 (M$^+$+1).

The following Examples, 21-26, were prepared as described for Example 20.

Example 21

6-Bromo-N-isopropyl-2-oxoindoline-5-carboxamide

Starting material: isopropylamine. Yield: 63%: MS (ES) m/z 297 and 299 (M$^+$+1).

Example 22

6-Bromo-N-(2-methoxyethyl)-2-oxoindoline-5-carboxamide

Starting material: 2-methoxyethylamine. Yield: 91%: $^1$H NMR (DMSO-d$_6$, 400 MHz) δ 7.19 (s, 1H), 6.97 (s, 1H), 3.46 (s, 2H), 3.42 (m, 2H), 3.34 (m, 2H), 3.26 (s, 3H); MS (ES) m/z 311 and 313 (M$^-$−1).

Example 23

6-Bromo-2-oxo-N-(tetrahydrofuran-2-ylmethyl)indoline-5-carboxamide

Starting material: tetrahydrofurfurylamine. Yield: 33%.

Example 24

6-Bromo-2-oxo-N-(2-pyrrolidin-1-ylethyl)indoline-5-carboxamide

Starting material: 1-(2-aminoethyl)pyrrolidine. Yield: 69%: MS (ES) m/z 352 and 354 (M$^+$+1).

Example 25

N-Methyl-2-oxoindoline-5-carboxamide

Starting material: methylamine. Yield: 45%: $^1$H NMR (DMSO-d$_6$, 400 MHz) δ 10.62 (s, 1H), 8.28 (m, 1H), 7.71 (m, 1H), 7.70 (s, 1H), 6.85 (d, J=8 Hz, 1H), 3.53 (s, 2H), 2.75 (d, J=4 Hz, 3H); $^{13}$C NMR (DMSO-d$_6$, 100 MHz) δ 176.7, 166.4, 146.3, 127.5, 127.2, 125.7, 123.3, 108.4, 35.6, 26.3; MS (ES) m/z 191 (M$^+$+1).

Example 26

N-[3-Dimethylamino)propyl]-2-oxoindoline-5-carboxamide

Starting material: N,N-dimethylpropanediamine. Yield: 63%: $^1$H NMR (DMSO-d$_6$, 400 MHz) δ 7.69 (m, 2H), 6.83 (d, J=9 Hz, 1H), 3.51 (s, 2H), 3.24 (m, 2H), 2.31 (m, 2H), 2.18 (s, 6H), 1.64 (m, 2H); MS (ES) m/z 262 (M$^+$+1).

Example 27

N-(2-Methoxybenzyl)-2-oxoindoline-5-carboxamide

To a solution of 2-oxoindoline-5-carboxylic acid (0.200 g, 1.12 mmol), 1-[3-(dimethylamino)propyl]-3-ethylcarbodiimide hydrochloride (0.477 g, 2.47 mmol), diisopropylethylamine (0.586 mL, 3.37 mmol) and catalytic amount of N,N-dimethylaminopyridine in N,N-dimethylformamide/acetonitrile (1:1, 4 mL) was added 2-methoxybenzylamine (0.295 mL, 2.26 mmol) and the reaction mixture stirred at room temperature for 1 h. The solvent was evaporated and the crude material was purified on a short silica gel column using dichloromethane containing 5% methanol as the eluent. This was followed by triturating from ethyl acetate to give 0.10 g (33% yield) of the yellow title compound: $^1$H NMR (DMSO-d$_6$, 400 MHz) δ 10.60 (br s, 1H), 8.65 (t, J=6 Hz, 1H), 7.79-7.77 (m, 2H), 7.21 (t, J=8 Hz, 1H), 7.15 (d, J=8 Hz, 1H), 6.98 (d, J=8 Hz, 1H), 6.90-6.84 (m, 2H), 4.42 (d, J=6 Hz, 2H), 3.81 (s, 3H), 3.53 (s, 2H); MS (ES) m/z 297 (M$^+$+1), m/z 295 (M$^-$−1).

The following Examples, 28-30, were prepared as described for Example 27.

Example 28

N-(3-Methoxybenzyl)-2-oxoindoline-5-carboxamide

Starting material: 3-methoxybenzylamine. Yield: 28% of the yellow title compound: $^1$H NMR (DMSO-d$_6$, 400 MHz) δ 10.60 (s, 1H), 8.83 (t, J=6 Hz, 1H), 7.77-7.75 (m, 2H), 7.24 (t, J=8 Hz, 1H), 6.85 (t, J=2 Hz), 6.80 (m, 1H), 4.40 (d, J=6 Hz, 2H), 3.71 (s, 3H), 3.52 (s, 2H).

Example 29

N-(4-Methoxybenzyl)-2-oxoindoline-5-carboxamide

Starting material: 4-methoxybenzylamine. Yield: 40%: $^1$H NMR (DMSO-d$_6$, 400 MHz) δ 10.59 (s, 1H), 8.77 (t, J=6 Hz, 1H), 7.75 (m, 2H), 7.22 (d, J=10 Hz, 2H), 6.87-6.83 (m, 3H), 4.37 (d, J=5 Hz, 2H), 3.71 (s, 3H), 3.51 (br s, 2H); MS (ES) m/z 297 (M$^+$+1), m/z 295 (M$^-$−1).

Example 30

2-Oxo-N-(tetrahydro-2H-pyran-4-yl)indoline-5-carboxamide

Starting material: tetrahydropyran-4-ylamine. Yield: 18%: $^1$H NMR (DMSO-d$_6$, 400 MHz) δ 10.58 (s, 1H), 8.11 (d, J=11 Hz, 1H), 7.73 (m, 2H), 6.84 (d, J=11 Hz, 1H), 3.95 (m, 1H), 3.86 (d, J=11 Hz, 2H), 3.51 (s, 2H), 3.36 (t, J=11 Hz, 2H), 1.72 (d, J=11 Hz, 2H), 1.60-1.51 (m, 2H).

Example 31

N-Benzyl-2-oxoindoline-5-carboxamide

2-Oxoindoline-5-carboxylic acid (0.214 g, 1.21 mmol), O-(benzotriazol-1-yl)-N,N,N',N'-tetramethyluronium tetrafluoroborate (0.462 g, 1.44 mmol), 1-hydroxybenzotriazole hydrate (0.194 g, 1.44 mmol) and N,N-diisopropylethylamine (0.3 mL, 1.71 mmol) were suspended in a mixture of acetonitrile (4 mL) and N,N-dimethylformamide (1 mL) and stirred at room temperature for 30 min. Benzylamine (0.155 g, 1.45 mmol) was added and stirring was continued for 12 h. The solvent was removed in vacuo and the residue was separated between chloroform and a saturated aqueous sodium hydrogen carbonate solution. The aqueous layer was extracted with chloroform (3×30 mL). The combined organic layers were dried over sodium sulfate. Filtration and removal of the solvent in vacuo yielded the crude product which was purified on a silica gel column using a gradient chloroform/methanol, (100:1 to 1:1), as the eluent to give 0.104 g (30% yield) of the title compound as a solid: $^1$H NMR (DMSO-d$_6$, 400 MHz) δ 10.60 (s, 1H), 8.85 (m, 1H), 7.77 (m, 2H), 7.29 (m, 4H), 7.21 (m, 1H), 6.85 (d, J=11 Hz, 1H), 4.45 (d, J=6 Hz, 2H), 3.52 (s, 2H); MS (ES) m/z 267 (M$^+$+1).

Example 32

N-(2-Methoxyethyl)-2-oxoindoline-5-carboxamide

2-Oxoindoline-5-carboxylic acid (0.470 g, 2.66 mmol), O-(benzotriazol-1-yl)-N,N,N',N'-tetramethyluronium tetrafluoroborate (1.010 g, 3.15 mmol), 1-hydroxybenzotriazole hydrate (0.417 g, 3.09 mmol) and N,N-diisopropylethylamine (0.7 mL, 4.0 mmol) were suspended in acetonitrile/N,N-dimethylformamide, (10 mL:2 mL), and stirred at room temperature for 30 min. 2-Methoxyethanamine (0.516 g, 6.88 mmol) was added and stirring was continued for 2 h. Saturated aqueous sodium hydrogencarbonate was added (10 mL) and the solvents were removed in vacuo. The residue was purified on a silica gel column using a gradient chloroform/methanol, (100:1 to 1:1), as the eluent to give 0.355 g (57% yield) of the title compound as a solid: $^1$H NMR (DMSO-d$_6$, 400 MHz) δ 10.59 (s, 1H), 8.31 (m, 1H), 7.72 (d, J=7 Hz, 1H), 7.71 (s, 1H), 6.83 (d, J=8 Hz, 1H), 3.51 (s, 2H), 3.42 (m, 2H), 3.39 (m, 2H), 3.24 (s, 3H); MS (ES) m/z 235 (M$^+$+1).

The following Examples, 33-35, were prepared as described for Example 32.

Example 33

2-Oxo-N-propylindoline-5-carboxamide

Starting material: propylamine. Yield: 11% as a solid: $^1$H NMR (CD$_3$OD, 400 MHz) δ 7.72 (d, J=8 Hz, 1H), 7.71 (s, 1H), 6.92 (d, J=8 Hz, 1H), 3.57 (s, 1H), 3.31 (m, 2H), 1.62 (sext, J=7 Hz, 2H), 0.96 (t, J=4 Hz, 3H); MS (ES) m/z 219 (M$^+$+1).

Example 34

N-[2-(Dimethylamino)ethyl]-2-oxoindoline-5-carboxamide

Starting material: N,N-dimethylethane-1,2-diamine. The residue was purified on a silica gel column using a gradient chloroform/methanol mixtures, (100:1 to 1:1 and 3% triethylamine), as the eluent. The residue was purified by preparative HPLC, (Xterra column (19×300 mm) with 0.05 M NH$_4$OAc buffer/acetonitrile, (90:10-30:70), as the eluent) to give the title compound in 18% yield: $^1$H NMR (CD$_3$OD, 400 MHz) δ 7.75 (m, 2H), 6.93 (d, J=8 Hz, 1H), 3.70 (t, J=6 Hz, 2H), 3.17 (t, J=6 Hz, 2H), 2.77 (m, 6H); MS (ES) m/z 248 (M$^+$+1).

Example 35

N-(2-Cyanoethyl)-2-oxoindoline-5-carboxamide

Starting material: 3-aminopropanenitrile. Work up: to the reaction mixture, methanol (3 mL) was added and the solvents were removed in vacuo. The residue was purified by re-crystallization from acetonitrile, and dried at 45° C. in vacuo to afford the title compound in 65% yield: $^1$H NMR (DMSO-d$_6$, 400 MHz) δ 10.63 (s, 1H), 8.65 (t, J=6 Hz, 1H), 7.77-7.70 (m, 2H), 6.87 (d, J=8 Hz, 1H), 3.54 (s, 2H), 3.47 (q, J=12, 6 Hz, 2H), 2.75 (t, J=6 Hz, 2H); MS (ES) m/z 230 (M$^+$+1).

Example 36

4-[(6-Chloro-1-oxidopyridin-3-yl)methyl]morpholine

A mixture of 2-chloro-5-(chloromethyl)pyridine 1-oxide (1.16 g, 6.52 mmol; described in: Tilley, J. W. et al, *J. Heterocyclic Chem.* 1979, 16, 333), morpholine (1.14 g, 13.0 mmol), and potassium carbonate (0.90 g, 6.52 mmol) in acetonitrile (30 mL) was stirred at room temperature for 72 h. The solvent was removed in vacuo and the residue was purified on a silica gel column using chloroform/ethanol, (9:1), as the eluent affording 1.2 g (81% yield) of the title compound as a colorless solid: mp 72-74° C.; $^1$H NMR (CDCl$_3$, 400 MHz) δ 8.34 (s, 1H), 7.39 (d, J=8 Hz, 1H), 7.16 (dd, J=8, 2 Hz, 1H), 3.65 (t, J=5 Hz, 4H), 3.40 (s, 2H), 2.40 (t, J=4 Hz, 4H); $^{13}$C NMR (CDCl$_3$, 100 MHz) δ 140.4, 135.9, 126.6, 126.6, 66.8, 59.2, 53.4; MS (ESP) m/z 229 (M$^+$+1).

Example 37

4-[(6-Chloropyridin-3-yl)sulfonyl]morpholine

A solution of triethylamine (0.27 mL, 1.94 mmol) and morpholine (0.085 mL, 0.97 mmol) in dry dichloromethane (2 mL) was added to a stirred suspension of 6-chloropyridine-3-sulfonyl chloride (0.204 g, 0.96 mmol; described in: Naegeli, C. et al. *Helv. Chim. Acta.* 1938, 21, 1746-1750) in dry dichloromethane (1 mL). The resulting clear solution was stirred at room temperature for 20 min. The solvent was evaporated and the residue was purified on a silica gel column using dichloromethane/methanol, (97:3), as the eluent to give 0.176 g (70% yield) of the title compound: $^1$H NMR (DMSO-d$_6$, 400 MHz) δ 8.75 (dd, J=3, 1 Hz, 1H), 8.18 (dd, J=8, 3 Hz, 1H), 7.82 (dd, J=8, 1 Hz, 1H), 3.63 (m, 4H), 2.96 (m, 4H).

Example 38

N-[(6-Chloro-1-oxidopyridin-3-yl)methyl]-N-ethylethanamine

2-Chloro-5-chloromethylpyridine 1-oxide (1.78 g, 10.0 mmol; described in: Tilley, J. W. et al, *J. Heterocyclic Chem.* 1979, 16, 333), diethyl amine (1.46 g, 20.0 mmol), and potassium carbonate (1.38 g, 10.0 mmol) were mixed in acetonitrile (50 mL) at room temperature. The mixture was stirred for 16 h, the solvent was removed in vacuo, and the residue was purified on a silica gel column using chloroform/methanol, (9:1), as the eluent to give 1.90 g (88% yield) of the title compound as a pale orange oil: MS (EI) m/z 215 and 217 (M$^+$+1).

Example 39

1-[(6-Chloro-1-oxidopyridin-3-yl)methyl]-4-methylpiperazine

A mixture of 2-chloro-5-(chloromethyl)pyridine 1-oxide (0.5 g, 2.8 mmol; described in: Tilley, J. W. et al, *J. Heterocyclic Chem.* 1979, 16, 333), 1-methylpiperazine (0.34 g, 3.37 mmol), and potassium carbonate (0.78 g, 5.62 mmol) in acetonitrile (5 mL) was stirred at room temperature for 13 h. The solvent was removed in vacuo and the residue was purified on a silica gel column using a gradient dichloromethane/methanol, (100:1 to 2:1), as the eluent affording 0.57 g (84% yield) of the title compound as a colorless solid: $^1$H NMR (CDCl$_3$, 400 MHz) δ 8.34 (s, 1H), 7.38 (d, J=8 Hz, 1H), 7.12 (d, J=8 Hz, 1H), 3.42 (s, 2H), 2.52 (s, 8H), 2.34 (m, 3H); $^{13}$C NMR (CDCl$_3$, 100 MHz) δ 140.6, 140.6, 136.3, 126.7, 58.9, 55.0, 52.6, 45.8; MS (ESP) m/z 242 (M$^+$+1).

The following Examples, 40-41, were prepared as described for Example 39.

Example 40

1-[(6-Chloro-1-oxidopyridin-3-yl)methyl]piperidine

Starting material: piperidine (0.29 g, 3.37 mmol). Yield: 0.47 g, 74%: $^1$H NMR (CDCl$_3$, 400 MHz) δ 8.30 (s, 1H), 7.35 (d, J=8 Hz, 1H), 7.13 (d, J=8 Hz, 1H), 3.32 (s, 2H), 2.29 (d, J=4 Hz, 4H), 1.49 (m, 4H), 1.36 (m, 2H); MS (ESP) m/z 227 (M$^+$+1).

Example 41

4-[(6-Chloro-1-oxidopyridin-3-yl)methyl]piperazin-2-one

Starting material: piperazinone (0.75 g, 7.5 mmol). Yield: 1.24 g, 73%: $^1$H NMR (CD$_3$OD, 400 Hz) δ 8.46 (d, J=1 Hz, 1H), 7.70 (d, J=8 Hz, 1H), 7.51 (dd, J=8, 2 Hz, 1H), 3.62 (s, 2H), 3.29 (m, 2H), 3.12 (m, 2H), 2.67 (m, 2H); MS (ESP) m/z 242 (M$^+$+1).

Example 42

N-{2-[(4-Methylpiperazin-1-yl)sulfonyl]ethyl}-2-oxoindoline-5-carboxamide

A solution of taurine (2.6 g, 21 mmol) in aqueous sodium hydroxide (1 M, 21 mL) was cooled to 0° C. Then, under vigorous stirring, a solution of benzyl chloroformate (4.2 g, 25 mmol) in dioxane (10 mL) was poured into the reaction mixture followed by the rapid addition of aqueous sodium hydroxide (1 M, 25 mL). After stirring for 1 h at 0° C., the reaction mixture was extracted with ethyl acetate (2×100 mL). Evaporation of the aqueous phase in vacuo followed by co-evaporation with toluene (2×200 mL) afforded the crude sodium sulfonate salt, which was dried in vacuo. The resulting solid material was is suspended in benzene (100 mL), and an excess of thionyl chloride (6.0 mL, 83 mmol) was added dropwise. The reaction mixture was stirred for 1 h at 50° C. and then under reflux for 2 h. After cooling, the mixture was concentrated in vacuo, dried, suspended in dichloromethane (50 mL), cooled to 0° C., and treated with a solution of N-methylpiperazine (2.3 mL, 21 mmol) in dichloromethane (20 mL). The solution was stirred for 16 h at room temperature, silica (10 g) was added, and the mixture was concentrated to dryness. The resulting solid residue was purified on a silica gel column using heptane/ethyl acetate, (1:1), as the eluent to afford 1 g (14% yield) of the benzyloxycarbonyl-protected sulfonamide as a colorless oil: MS (ES) m/z 342 (M$^+$+1). The above material was dissolved in methanol (50 mL) and formic acid (5 mL) and hydrogenated over Pd/C (0.40 g) at elevated hydrogen pressure (50 psi) for 16 h. The reaction mixture was filtered through a plug of celite (10 g), the celite was washed with methanol (2×20 mL), the combined filtrates were evaporated to dryness, dissolved in H$_2$O (20 mL), and re-evaporated. The resulting residue was dissolved in N,N-dimethylformamide (5 mL), and added in one portion to the previously prepared suspension of 2-oxoindoline-5-carboxylic acid (0.53 g, 3 mmol), O-(benzotriazol-1-yl)-N,N,N',N'-tetramethyluronium tetrafluoroborate (1.1 g, 3.6 mmol), 1-hydroxybenzotriazole (0.486 g, 3.6 mmol) and N,N-diisopropylethylamine (1.7 g, 12 mmol) in acetonitrile (10 mL) and N,N-dimethylformamide (10 mL). The mixture was stirred overnight, the solvents were removed in vacuo, and the residue was purified on a silica gel column using chloroform/methanol, (10:1), then chloroform/methanol/aqueous ammonia, (100:10:1), as the eluent. The semi-solid crude material was again subjected to silica gel chromatography using chloroform/methanol/aqueous ammonia, (150:10:1), as the eluent to afford 0.20 g (19% yield) the title compound as yellow foam: MS (ES) m/z 367 (M$^+$+1).

Example 43

4-{2-[(6-Chloropyrimidin-4-yl)oxy]ethyl}morpholine

A mixture of 4,6-dichloropyrimidine (1.0 g, 6.7 mmol), N-(2-hydroxyethyl)morpholine (0.79 g, 0.60 mmol), and potassium carbonate (2.8 g, 20 mmol) in acetonitrile (5 mL) was stirred at room temperature for 15 h. The solvent was removed in vacuo and the residue was purified on a silica gel column using a gradient dichloromethane/methanol, (100:1 to 2:1), as the eluent to give 0.47 g (32% yield) of the yellow title compound: $^1$H NMR (CDCl$_3$, 400 MHz) δ 8.48 (s, 1H), 6.72 (s, 1H), 4.45 (t, J=6 Hz, 2H), 3.62 (m, 4H), 2.46 (m, 4H) 2.69 (t, J=6 Hz, 2H), $^{13}$C NMR (CDCl$_3$, 100 MHz) δ 169.9, 160.5, 157.9, 107.8, 66.7, 64.4; MS (ESP) m/z 244 (M$^+$+1).

Example 44

N-{2-[(6-Chloropyrimidin-4-yl)oxy]ethyl}-N-isopropylpropan-2-amine

A mixture of 4,6-dichloropyrimidine (0.5 g, 3.4 mmol), 2-(diisopropylamino)ethanol (0.44 g, 3.0 mmol), and cesium carbonate (2.18 g, 6.7 mmol) in butyronitrile (4 mL) was heated in a microwave oven at 180° C. for 20 min. Filtration followed by purification using preparative HPLC (XTerra®PrepMS C8 column 10 μm, 30×150 mm; 0.1 M NH$_4$OAc buffer/acetonitrile, (80:20-20:80), as the eluent) gave 0.156 g (20% yield) of the title compound: MS (ESP) m/z 258 (M$^+$+1).

Example 45

Ethyl 6-(6-cyano-2-hydroxy-1H-indol-3-yl)nicotinate

To a N,N-dimethylformamide (6 mL) suspension of sodium hydride (97%, 0.144 g, 6.0 mmol) was added 2-oxoindoline-6-carbonitrile (0.712 g, 4.5 mmol). The formed mixture was stirred for 10 min at room temperature followed by the addition of ethyl 6-chloronicotinate 1-oxide (0.605 g, 3.0 mmol). The resulting reaction mixture was set under N$_2$ atmosphere and stirred for 2 h at room temperature. The N,N-dimethylformamide reaction solution was diluted with a saturated aqueous sodium hydrogen carbonate solution and extracted with chloroform and ethyl acetate. The combined organic layers were dried (Na$_2$SO$_4$) and concentrated in vacuo. The remaining N,N-dimethylformamide was removed by co-evaporation with toluene. The residue was dissolved in chloroform (10 mL) and phosphorus trichloride (1.65 g, 12.0 mmol) was added. The reaction mixture was stirred for 30 min at 60° C. and then cooled to room temperature. The mixture was poured into a saturated aqueous sodium hydrogen carbonate solution. The resulting brown precipitate was filtered off and the mother liquor was extracted with chloroform (4×). The organic layers were concentrated in vacuo and the residue was combined with the filtrate and was washed with ethyl acetate and diethyl ether to afford 0.55 g (60% yield) of the title compound as a yellow-brown solid: $^1$H NMR (DMSO-$d_6$, 400 MHz) δ 8.85 (s, 1H), 8.06 (s, 1H), 8.00 (d, J=8.8 Hz, 1H), 7.75 (d, J=8.0 Hz, 1H), 7.69 (d, J=8.0 Hz, 1H), 7.45 (s, 1H), 7.29 (d, J=8.8 Hz, 1H), 4.33 (m, 2H), 1.35 (t, J=7.2 Hz, 3H); MS (EI) m/z 308 (M$^+$+1).

Example 46

Methyl 2-hydroxy-3-[5-(morpholin-4-ylmethyl)pyridin-2-yl]-1H-indole-5-carboxylate To a N,N-dimethylformamide (10 mL) suspension of sodium hydride (97%, 0.784 g, 32.7 mmol) was added methyl 2-oxoindoline-5-carboxylate (2.34 g, 12.3 mmol). The formed mixture was stirred for 10 min at room temperature followed by the addition of 4-[(6-chloro-1-oxidopyridin-3-yl)methyl]morpholine (1.87 g, 8.2 mmol). The resulting reaction mixture was set under $N_2$ atmosphere and stirred for 1 h at 135° C. The N,N-dimethylformamide solution was diluted with saturated aqueous sodium hydrogen carbonate (30 mL) and extracted with chloroform, and ethyl acetate (containing 5% methanol). The combined organic phases were concentrated in vacuo. The remaining N,N-dimethylformamide was removed by co-evaporation with toluene. The residue was dissolved in ethyl acetate/chloroform, (150 mL, 2:1), and phosphorus trichloride (4.5 g, 33 mmol) was added. The reaction mixture was stirred for 1 h at 60° C., and then cooled to room temperature. The mixture was poured into a saturated aqueous sodium hydrogen carbonate solution followed by extraction of the aqueous phase with chloroform (4×). The combined organic extracts were concentrated in vacuo, and the residue was purified on a silica gel column using chloroform/methanol, (10:1), as the eluent to afford 1.05 g (35% yield) of the title compound as a yellow-brown solid: $^1$H NMR (DMSO-$d_6$, 400 MHz) δ 10.83 (br s, 1H), 8.11 (s, 1H), 8.04 (s, 1H), 7.91 (d, J=8.0 Hz, 1H), 7.63 (t, J=8.0 Hz, 2H), 7.00 (d, J=8.0 Hz, 1H), 3.87 (s, 3H), 3.62 (br s, 4H), 3.41 (s, 2H), 2.42 (br s, 4H); MS (EI) m/z 368 (M$^+$+1).

Example 47

Methyl 3-{5-[(diethylamino)methyl]pyridin-2-yl}-2-hydroxy-1H-indole-5-carboxylate The title compound was prepared according to Example 46 using N-[(6-chloro-1-oxidopyridin-3-yl)methyl]-N-ethylethanamine (0.950 g, 4.4 mmol). The product was obtained as an orange yellow solid (0.492 g, 32% yield): $^1$H NMR (CD$_3$OD, 400 MHz) δ 8.19 (s, 1H), 8.05 (s, 1H), 7.93 (dd, J=8.0, 2.0 Hz, 1H), 7.92 (d, J=9.6 Hz, 1H), 7.74 (dd, J=8.0, 1.6 Hz, 1H), 7.10 (d, J=8.4 Hz, 1H), 3.94 (s, 3H), 3.81 (br s, 2H), 2.85 (br s, 4H), 1.34 (t, J=7.2 Hz, 6H); MS (EI) m/z 354 (M$^+$+1).

Example 48

Methyl 2-hydroxy-3-{5-[(4-methylpiperazin-1-yl) sulfonyl]pyridin-2-yl}-1H-indole-5-carboxylate The title compound was prepared as described for Example 103 using 1-[(6-chloropyridine-3-yl)sulfonyl]-4-methylpiperazine (described in: Thunus. L. *Annales Pharmaceutiques Francaises* 1977, 35, 197-204) and methyl 2-oxoindoline-5-carboxylate to give the title compound in 59% yield, but without the treatment of the base with hydrochloric acid to from the salt: $^1$H NMR (D$_2$O, 400 MHz) δ 8.03 (d, J=2 Hz, 1H), 7.44 (m, 1H), 7.30 (d, J=8 Hz, 1H), 7.23 (s, 1H), 6.82 (d, J=9 Hz, 1H), 6.70 (d, J=8 Hz, 1H), 3.93 (m, 2H), 3.82 (s, 3H), 3.65 (m, 2H), 3.28 (m, 2H), 3.03 (m, 2H), 2.94 (s, 3H); MS (TSP) m/z 431 (M$^+$+1).

Example 49

2-Hydroxy-3-{5-[(4-methylpiperazin-1-yl)sulfonyl] pyridin-2-yl}-1H-indole-5-carboxylic acid To a mixture of 2-hydroxy-3-{5-[(4-methylpiperazin-1-yl) sulfonyl]pyridin-2-yl}-1H-indole-5-carbonitrile (0.10 g, 0.25 mmol) in water (2 mL) was added 1 M aqueous sodium hydroxide solution (1.3 mL, 1.3 mmol) followed by water (1 mL) in a microwave vial. The mixture was subjected to microwave irradiation for 15 min at 140° C. The pH was adjusted to 5 with 2 M HCl. The solid product was collected by filtration, washed with diethyl ether, and dried to afford 0.11 g (89% yield) of the title compound: MS (ESP) m/z 417 (M$^+$+1).

Example 50

Methyl 3-(4-cyanopyridin-2-yl)-2-hydroxy-1H-indole-5-carboxylate

The title compound was prepared as described for Example 86 using methyl 2-oxoindoline-5-carboxylate and 2-chloro-5-cyanopyridine, but the reaction mixture was heated to 135° C. for 1 h. The product was purified on a silica gel column using chloroform/methanol, (first 20:1, then 15:1), as the eluent to afford the title compound as a dark-red powder in 20% yield: MS (ES) m/z 294 (M$^+$+1).

End Products

Example 51

2-Hydroxy-3-{5-[(4-methylpiperazin-1-yl)carbonyl] pyridin-2-yl}-1H-indole-6-carbonitrile hydrochloride To a suspension of sodium hydride (97%, 0.024 g, 1.0 mmol) in N,N-dimethylformamide (1.5 mL) was added 2-oxoindoline-6-carbonitrile (0.119 g, 0.75 mmol). The resulting mixture was stirred for 5 min at room temperature and 1-[(6-chloro-1-oxidopyridin-3-yl)carbonyl]-4-methylpiperazine (0.128 g, 0.5 mmol) was added. The resulting reaction mixture was set under an $N_2$ atmosphere and stirred for 20 h at room temperature. The N,N-dimethylformamide reaction solution was diluted with saturated aqueous sodium hydrogen carbonate and sodium chloride (2.0 g) was added followed by extractions with chloroform, ethyl acetate, and tetrahydrofuran. The combined organic extracts were dried (Na$_2$SO$_4$) and concentrated in vacuo. The remaining N,N-dimethylformamide was removed by co-evaporation with toluene (1×). The residual oil was dissolved in a chloroform/ethyl acetate, (5:1, 6 mL), and phosphorus trichloride (0.275 g, 2.0 mmol) was added. The reaction mixture was stirred for 60 min at 60° C., and was then cooled to room temperature. The mixture was poured into a saturated aqueous sodium hydrogen carbonate solution and sodium chloride (2.0 g) was added followed by extractions with chloroform (4×) and ethyl acetate (2×). The combined organic extracts were dried (Na$_2$SO$_4$) and concentrated in vacuo. Purification using preparative HPLC (XTerra®PrepMS C8 column 10 µm, 30×150 mm; 0.1 M NH$_4$OAc buffer/acetonitrile, (80:20-20:80), as the eluent) gave 0.028 g (15% yield) of the title compound as the base.

The base (0.025 g, 0.069 mmol) was dissolved in chloroform/methanol, (1:1), and treated with HCl in diethyl ether (1 M) at 0° C. The resulting yellow crystals were collected by filtration and washed with diethyl ether to obtain 0.020 g (70% yield) of the title compound: $^1$H NMR (DMSO-$d_6$, 400 MHz) δ 10.61 (br s, 1H), 8.41 (s, 1H), 7.93 (br s, 1H), 7.80 (br s, 2H), 7.30 (br s, 1H), 7.15 (br s, 1H), 3.58 (br s, 4H), 2.40 (br s, 4H), 2.25 (s, 3H); MS (EI) m/z 362 (M$^+$+1).

Example 52

6-(6-Cyano-2-hydroxy-1H-indol-3-yl)-N-(2-morpholin-4-ylethyl)nicotinamide hydrochloride A suspension of ethyl 6-(6-cyano-2-hydroxy-1H-indol-3-yl)nicotinate (0.092 g, 0.3 mmol) and 4-(2-aminoethyl)morpholine (0.098 g, 0.75 mmol) in benzene (4.0 mL) was prepared at room temperature and was set under an N$_2$ atmosphere. To the suspension, trimethylaluminum (2 M solution in hexane, 0.6 mL, 1.2 mmol) was added via syringe at 0° C. After 5 min, the reaction mixture was heated to 70° C. and was stirred for another 16 h. The mixture was cooled to room temperature, poured into a saturated aqueous sodium hydrogen carbonate solution (10 mL), and extracted with chloroform. The combined organic phases were dried (Na$_2$SO$_4$) and concentrated in vacuo. The residue was purified on a silica gel column using chloroform/methanol/triethylamine, (100:20:1), as the eluent to afford 0.020 g (17% yield) of the title compound as the base. The base (0.020 g, 0.005 mmol) was dissolved in chloroform/methanol, (1:1), and treated with HCl in diethyl ether (1 M) at 0° C. followed by addition of diethyl ether. The resulting yellow crystals were collected by filtration and washed with diethyl ether to obtain 0.020 g (87% yield) of the title compound: $^1$H NMR (DMSO-$d_6$, 400 M) δ 10.92 (s, 2H), 9.13 (t, J=4.8 Hz, 1H), 8.81 (s, 1H), 8.36 (d, J=9.2 Hz, 1H), 7.86 (d, J=9.2 Hz, 1H), 7.80 (d, J=8.0 Hz, 1H), 7.38 (d, J=8.0 Hz, 1H), 7.23 (s, 1H), 4.34 (d, J=11.6 Hz, 2H), 3.86 (t, J=12.0 Hz, 2H), 3.73 (m, 2H), 3.61 (d, J=11.6 Hz, 2H), 3.35 (m, 2H), 3.17 (m, 2H); MS (EI) m/z 392 (M$^+$+1).

The following Examples, 53 and 54, were prepared as described for Example 52.

Example 53

6-(6-Cyano-2-hydroxy-1H-indol-3-yl)-N-methyl-N-(2-pyrrolidin-1-ylethyl)nicotinamide hydrochloride Starting material: methyl-(2-pyrrolidin-1-ylethyl)amine (0.096 g, 0.75 mmol, 2.5 equiv.; described in: Krapcho J. et al. *J. Am. Chem. Soc.* 1955, 77, 3632-3634). The crude product was purified on a silica gel column using chloroform/methanol/triethylamine, (100:33:1), as the eluent to give 0.056 g (50% yield) of the title compound as the base. The hydrochloride salt was obtained (0.040 g, 62% yield) as a yellow solid: $^1$H NMR (DMSO-$d_6$, 400 MHz) δ 10.89 (s, 1H), 9.97 (br s, 1H), 8.51 (s, 1H), 8.05 (d, J=8.8 Hz, 1H), 7.85 (d, J=8.8 Hz, 1H), 7.75 (d, J=8.0 Hz, 1H), 7.39 (d, J=8.0 Hz, 1H), 7.24 (s, 1H), 3.81 (m, 6H), 3.47 (m, 2H), 3.12 (br s, 3H), 2.06 (m, 2H), 1.93 (m, 2H); MS (EI) m/z 390 (M$^+$+1).

Example 54

6-(6-Cyano-2-hydroxy-1H-indol-3-yl)-N-(2-(dimethylamino)ethyl)-N-methylnicotinamide hydrochloride Starting material: N,N,N'-trimethylethane-1,2-diamine (2.5 equiv.). The crude product was dissolved in chloroform/methanol, (1:1), and the insoluble material was filtered off followed by concentration in vacuo. Yield: 85% of the title compound: $^1$H NMR (DMSO-$d_6$, 400 MHz) δ 10.90 (s, 1H), 9.97 (br s, 1H), 8.52 (s, 1H), 8.05 (d, J=7.2 Hz, 1H), 7.85 (d, J=7.2 Hz, 1H), 7.75 (d, J=8.0 Hz, 1H), 7.39 (d, J=8.0 Hz, 1H), 7.24 (s, 1H), 3.83 (br s, 9H), 3.40 (m, 2H), 2.87 (m, 2H); MS (EI) m/z 364 (M$^+$+1).

Example 55

6-(6-Cyano-2-hydroxy-1H-indol-3-yl)-N-(2-pyrrolidin-1-ylethyl)pyridine-3-sulfonamide hydrochloride To a suspension of sodium hydride (97%, 0.036 g, 1.5 mmol) in 1-methyl-2-pyrrolidinone (2 mL) was added 2-oxoindoline-6-carbonitrile (0.119 g, 0.75 mmol). The formed mixture was stirred for 5 min at room temperature and 6-chloro-N-(2-pyrrolidin-1-ylethyl)pyridine-3-sulfonamide (0.145 g, 0.5 mmol) was added. The resulting reaction mixture was set under an N$_2$ atmosphere and stirred for 1 h at 90° C. Methanol (0.4 mL) was added and the solvents were removed in vacuo. The crude product was purified by preparative HPLC purification (XTerra®PrepMS C8 column 10 μm, 30×150 mm; 0.1 M NH$_4$OAc buffer/acetonitrile, (80:20 to 40:60), as a eluent gradient). The collected product was stirred for 16 h in methanol/ethyl acetate, (5:1 mL), and the brownish red solid was collected by filtration affording 0.056 g (27% yield) of the title compound as the base. The base (0.046 g, 0.11 mmol) was dissolved in chloroform/methanol, (1:1), and treated with HCl in diethyl ether (1 M) at 0° C. The resulting brownish red crystals were collected by filtration and washed with diethyl ether to obtain 0.022 g (40% yield) of the title compound: $^1$H NMR (D$_2$O, 400 MHz) δ 8.63 (s, 1H), 8.10 (d, J=9.2 Hz, 1H), 7.99 (d, J=8.4 Hz, 1H), 7.80 (dd, J=9.2, 2.4 Hz, 1H), 7.22 (s, 1H), 7.21 (dd, J=8.0, 1.6 Hz, 1H) 2.91 (t, J=6.8 Hz, 2H), 2.51 (m, 6H), 1.61 (br s, 4H); MS (EI) m/z 412 (M$^+$+1).

Example 56

2-Hydroxy-3-[5-(piperazine-1-sulfonyl)pyridin-2-yl]-1H-indole-6-carbonitrile hydrochloride To a suspension of sodium hydride (97%, 0.024 g, 1.0 mmol) in 1-methyl-2-pyrrolidinone (2 mL) was added 2-oxoindoline-6-carbonitrile (0.119 g, 0.75 mmol). The formed mixture was stirred for 5 min at room temperature and tert-butyl 4-[(6-chloropyridin-3-yl)sulfonyl]piperazine-1-carboxylate (0.181 g, 0.5 mmol) was added. The resulting reaction mixture was set under an N$_2$ atmosphere and stirred for 1 h at 90° C. Methanol (0.5 mL) was added to the mixture and the solvents were removed in vacuo. The crude product was dissolved in methanol (5 mL) and HCl in diethyl ether (4 M, 2.5 mL, 10 mmol) was added followed by reflux for 3 h. From the cooled solution the formed yellow precipitate was collected by filtration and dried to give 0.209 g (92% yield) of the title compound: $^1$H NMR (DMSO-$d_6$, 400 MHz) δ 11.08 (s, 1H), 9.10 (br s, 2H), 8.67 (s, 1H), 7.89 (s, 2H), 7.78 (d, J=8.0 Hz, 1H), 7.44 (dd, J=8.0, 1.2 Hz, 1H), 7.28 (d, J=1.2 Hz, 1H) 3.31 (br s, 4H), 3.25 (br s, 4H); MS (EI) m/z 384 (M$^+$+1).

Example 57

3-[5-({4-[2-(Dipropylamino)ethyl]piperazin-1-yl}sulfonyl)pyridin-2-yl]-2-hydroxy-1H-indole-6-carbonitrile hydrochloride To a suspension of sodium hydride (97%, 0.024 g, 1.0 mmol) in 1-methyl-2-pyrrolidinone (1.5 mL) was added (2-{4-[(6-chloropyridin-3-yl)sulfonyl]piperzin-1-yl}ethyl)dipropylamine (0.194 g, 0.5 mmol) at room temperature followed by addition of 2-oxoindoline-6-carbonitrile (0.095 g, 0.6 mmol). The formed mixture was stirred for 5 min under an $N_2$ atmosphere and stirred for 1 h at 90° C. The cooled solution was poured into a cold saturated aqueous sodium hydrogen carbonate solution and the resulting precipitate was collected by filtration. The crude product was purified on a silica gel column using chloroform/methanol/triethylamine, (100:80:1), as the eluent to give 0.130 g (51% yield) of the title compound as the base. The base (0.127 g, 0.25 mmol) was dissolved in chloroform/methanol, (1:1), and treated with HCl in diethyl ether (1 M) at 0° C. The resulting orange crystals were collected by filtration and washed with diethyl ether to obtain 0.125 g (86% yield) of the title compound: $^1$H NMR (DMSO-$d_6$, 400 MHz) δ 11.07 (s, 1H), 8.67 (s, 1H), 7.89 (s, 2H), 7.78 (d, J=8.0 Hz, 1H), 7.44 (dd, J=8.0, 1.2 Hz, 1H), 7.28 (d, J=1.2 Hz, 1H), 4.04 (br s, 10H), 3.05 (br s, 6H), 1.69 (br s, 4H), 0.91 (t, J=7.2 Hz, 6H); MS (EI) m/z 511 ($M^+$+1).

The following Examples, 58-61, were prepared as described for Example 57.

Example 58

2-Hydroxy-3-(5-{[4-(2-morpholin-4-ylethyl)piperazin-1-yl]sulfonyl}pyridin-2-yl)-1H-indole-6-carbonitrile hydrochloride Starting material: 4-(2-{4-[(6-chloropyridin-3-yl)sulfonyl]piperzin-1-yl}ethyl)morpholine. The crude product was purified on a silica gel column using chloroform/methanol/triethylamine, (100:25:1), as the eluent to give the title compound as the base in 40% yield. The base was transformed to the corresponding reddish orange hydrochloride salt. Yield: 71% of the title compound: $^1$H NMR (DMSO-$d_6$, 400 MHz) δ 11.07 (s, 1H), 8.67 (s, 1H), 7.89 (m, 2H), 7.78 (d, J=8.0 Hz, 1H), 7.44 (d, J=8.0 Hz, 1H), 7.28 (s, 1H), 4.07 (br s, 8H), 3.89 (br s, 4H), 3.55 (br s, 4H), 3.27 (br s, 4H); MS (EI) m/z 497 ($M^+$+1).

Example 59

2-Hydroxy-3-(5-{[4-(2-pyrrolidin-1-ylethyl)piperazin-1-yl]sulfonyl}pyridin-2-yl)-1H-indole-6-carbonitrile hydrochloride Starting material: 1-[(6-chloropyridin-3-yl)sulfonyl]-4-(2-pyrrolidin-1-ylethyl)piperazine. The crude product was purified on a silica gel column using chloroform/methanol/triethylamine, (100:100:1), as the eluent to give the title compound as the base in 25% yield. The base was transformed to the corresponding reddish orange hydrochloride salt. Yield: 71% of the title compound: $^1$H NMR (DMSO-$d_6$, 400 MHz) δ 11.07 (s, 1H), 8.67 (s, 1H), 7.89 (br s, 2H), 7.78 (d, J=8.0 Hz, 1H), 7.44 (dd, J=8.0, 1.2 Hz, 1H), 7.28 (d, J=1.2 Hz, 1H), 4.84 (br s, 4H), 3.58 (br s, 6H), 3.20 (br s, 6H), 1.94 (br s, 4H); MS (EI) m/z 481 ($M^+$+1).

Example 60

2-Hydroxy-3-(5-{[4-(2-methoxyethyl)piperazin-1-yl]sulfonyl}pyridin-2-yl)-1H-indole-6-carbonitrile hydrochloride Starting material: 1-[(6-chloropyridin-3-yl)sulfonyl]-4-(2-methoxyethyl)piperazine. The crude product was purified on a silica gel column using chloroform/methanol/triethylamine, (90:10:1), as the eluent to give the base in 36% yield. The base was transformed to the hydrochloride salt. Yield: 65% of the title compound: $^1$H NMR (DMSO-$d_6$, 400 MHz) δ 11.07 (s, 1H), 10.07 (br s, 1H), 8.67 (s, 1H), 7.89 (br s, 2H), 7.79 (d, J=8.0 Hz, 1H), 7.44 (d, J=8.0 Hz, 1H), 7.29 (s, 1H), 3.74 (br s, 2H), 3.68 (br s, 2H), 3.62 (br s, 1H), 3.59 (br s, 1H), 3.36 (br s, 2H), 3.31 (s, 3H), 3.24 (br s, 2H), 3.00 (m, 2H); MS (EI) m/z 442 ($M^+$+1).

Example 61

2-Hydroxy-N-(3-methoxypropyl)-3-{5-[(4-methylpiperazin-1-yl)sulfonyl]pyridin-2-yl}-1H-indole-5-carboxamide hydrochloride Starting materials: N-(3-methoxypropyl)-2-oxoindoline-5-carboxamide (0.149 g, 0.6 mmol) and 1-[(6-chloropyridine-3-yl)sulfonyl]-4-methylpiperazine (0.138 g, 0.5 mmol; described in: Thunus L., *Annales Pharmaceutiques Francaises* 1977, 35, 197-204). The orange base (0.059 g, 0.12 mmol) was treated with HCl in diethyl ether to obtain the orange hydrochloride salt. Yield: 83% of the title compound: $^1$H NMR (DMSO-$d_6$, 400 MHz) δ 10.93 (s, 1H), 10.84 (br s, 1H), 8.55 (br s, 1H), 8.45 (t, J=5.2 Hz, 1H), 8.04 (s, 1H), 7.81 (s, 2H), 7.63 (d, J=8.4 Hz, 1H), 7.00 (d, J=8.0 Hz, 1H), 3.80 (d, J=12.8 Hz, 2H), 3.53 (d, J=11.6 Hz, 2H), 3.43 (m, 2H), 3.37 (m, 2H), 3.29 (s, 3H), 3.19 (m, 2H), 3.01 (m, 2H), 2.81 (s, 3H), 1.82 (m, 2H); MS (EI) m/z 488 ($M^+$+1).

Example 62

2-Hydroxy-N-(2-methoxyethyl)-3-[5-(morpholin-4-ylmethyl)pyridin-2-yl]-1H-indole-5-carboxamide hydrochloride To a suspension of sodium hydride (97%, 0.030 g, 1.25 mmol) in N,N-dimethylformamide (1.5 mL) was added N-(2-methoxyethyl)-2-oxoindoline-5-carboxamide (0.176 g, 0.75 mmol). The formed mixture was stirred for 5 min at room temperature followed by the addition of 4-[(6-chloro-1-oxidopyridin-3-yl)methyl]morpholine (0.114 g, 0.5 mmol). The resulting reaction mixture was set under an $N_2$ atmosphere and stirred for 1 h at 120° C. and then concentrated in vacuo. The remaining N,N-dimethylformamide was removed by co-evaporation with toluene (1×). The residue was purified on a silica gel column using chloroform/methanol/triethylamine, (90:10:1), as the eluent. The material was dissolved in chloroform (4 mL), and phosphorus trichloride (0.275 g, 2.0 mmol) was added. The reaction mixture was stirred for 1 h at 60° C. and then concentrated in vacuo. The residue was purified on a silica gel column using chloroform/methanol/triethylamine, (90:10:1), as the eluent followed by further purification by washing with diethyl ether (3 mL) to give 0.050 g (24% yield) of the title compound as the base. The base (0.050 g, 0.12 mmol) was dissolved in chloroform/methanol, (1:1), and treated with HCl in diethyl ether (1 M) at 0° C. The resulting yellow crystals were collected by filtration and washed with diethyl ether to obtain 0.029 g (50% yield) of the title compound: $^1$H NMR (DMSO-$d_6$, 400 MHz) δ 11.48 (br s, 1H), 10.74 (br s, 1H), 8.54 (br s, 1H), 8.27 (s, 1H), 8.11 (d, J=8.0 Hz, 1H), 8.03 (s, 1H), 7.87 (d, J=9.2 Hz, 1H), 7.59 (d, J=8.4 Hz, 1H), 6.98 (d, J=8.4 Hz, 1H), 4.29 (br s, 1H), 4.00 (d, J=11.2 Hz, 2H), 3.87 (d, J=11.2 Hz, 1H), 3.83 (d, J=12.4 Hz, 1H), 3.50 (br s, 4H), 3.38 (d, J=12.4 Hz, 2H), 3.32 (s, 3H), 3.13 (m, 2H); MS (EI) m/z 411 ($M^+$+1).

The following Examples, 63-66, were prepared as described for Example 62.

Example 63

2-Hydroxy-3-[5-(morpholin-4-ylmethyl)pyridin-2-yl]-N-(pyridin-2-ylmethyl)-1H-indole-5-carboxamide hydrochloride Starting material: 2-oxo-N-(pyridin-2-ylmethyl)indoline-5-carboxamide. The hydrochloride salt was obtained as a yellow solid. Yield: 14% of the title compound: $^1$H NMR (DMSO-$d_6$, 400 MHz) δ 11.43 (br s, 1H), 10.80 (s, 1H), 9.43 (br s, 1H), 8.80 (d, J=5.2 Hz, 1H), 8.36 (m, 1H), 8.27 (s, 1H), 8.18 (s, 1H), 8.12 (d, J=5.2 Hz, 1H), 7.97 (d, J=9.2 Hz, 1H), 7.87 (d, J=8.0 Hz, 1H), 7.79 (m, 1H), 7.64 (d, J=9.2 Hz, 1H), 7.02 (d, J=8.0 Hz, 1H), 4.83 (d, J=6.0 Hz, 2H), 4.29 (br s, 2H), 4.00 (d, J=11.2 Hz, 2H), 3.86 (d, J=12.4 Hz, 1H), 3.80 (d, J=11.2 Hz, 1H), 3.38 (d, J=12.4 Hz, 2H), 3.11 (m, 2H); MS (EI) m/z 444 (M$^+$+1).

Example 64

2-Hydroxy-3-[5-(morpholin-4-ylmethyl)pyridin-2-yl]-N-(2-thienylmethyl)-1H-indole-5-carboxamide hydrochloride Starting material: 2-oxo-N-(2-thienylmethyl)indoline-5-carboxamide. The orange yellow free base was treated with HCl in diethyl ether (1 M) to give the title compound. Yield: 87% as a yellow solid: $^1$H NMR (DMSO-$d_6$, 400 MHz) δ 11.12 (br s, 1H), 10.75 (s, 1H), 9.11 (t, J=6.0 Hz, 1H), 8.25 (s, 1H), 8.05 (br s, 2H), 7.85 (d, J=8.8 Hz, 1H), 7.62 (d, J=7.6 Hz, 1H), 7.42 (d, J=5.2 Hz, 1H), 7.07 (s, 1H), 7.00 (m, 2H), 4.72 (d, J=5.6 Hz, 2H), 4.29 (br s, 2H), 4.00 (d, J=11.2 Hz, 2H), 3.80 (m, 2H), 3.38 (d, J=12.0 Hz, 2H), 3.14 (m, 2H); MS (EI) m/z 449 (M$^+$+1).

Example 65

2-Hydroxy-3-[5-(morpholin-4-ylmethyl)pyridin-2-yl]-N-[2-(2-oxoimidazolidin-1-yl)ethyl]-1H-indole-5-carboxamide hydrochloride Starting material: 2-oxo-N-[2-(2-oxoimidazolidin-1-yl)ethyl]indoline-5-carboxamide. The crude product was purified by preparative HPLC (XTerra®PrepMS C8 column 10 μm, 30×150 mm; 0.1 M NH$_4$OAc buffer/acetonitrile, (95:5 to 60:40), as the eluent) to give the title compound as the base in 27% yield. The base was treated with HCl in diethyl ether (1 M) to give the title compound. Yield: 88%: $^1$H NMR (DMSO-$d_6$, 400 MHz) δ 11.72 (br s, 1H), 10.67 (s, 1H), 8.46 (t, J=5.2 Hz, 1H), 8.20 (s, 1H), 8.11 (dd, J=9.2, 1.6 Hz, 1H), 7.93 (s, 1H), 7.82 (d, J=9.2 Hz, 1H), 7.48 (d, J=8.8 Hz, 1H), 6.91 (d, J=8.4 Hz, 1H), 4.23 (d, J=4.0 Hz, 2H), 3.93 (d, J=11.2 Hz, 2H), 3.80 (t, J=12.0 Hz, 2H), 3.38 (m, 4H), 3.32 (d, J=12.0 Hz, 2H), 3.20 (m, 4H), 3.03 (m, 2H); MS (EI) m/z 465 (M$^+$+1).

Example 66

N-[2-(Acetylamino)ethyl]-2-hydroxy-3-[5-(morpholin-4-ylmethyl)pyridin-2-yl]-1H-indole-5-carboxamide hydrochloride Starting material: N-[2-(acetylamino)ethyl]-2-oxoindoline-5-carboxamide. Yield: 51%: $^1$H NR (D$_2$O, 400 MHz) δ 7.65 (br s, 1H), 7.56 (br s, 2H), 7.37 (m, 1H), 7.29 (d, J=9.2 Hz, 1H), 6.97 (d, J=8.4 Hz, 1H), 3.73 (br s, 4H), 3.51 (d, J=4.8 Hz, 2H), 3.46 (d, J=5.6 Hz, 2H), 3.32 (s, 2H), 2.52 (br s, 4H), 2.01 (s, 3H); MS (EI) m/z 438 (M$^+$+1).

Example 67

2-Hydroxy-N-(2-methoxybenzyl)-3-[5-(morpholin-4-ylmethyl)pyridin-2-yl]-1H-indole-5-carboxamide hydrochloride A suspension of methyl 2-hydroxy-3-[5-(morpholin-4-ylmethyl)pyridin-2-yl]-1H-indole-5-carboxylate (0.074 g, 0.2 mmol) and 2-methoxybenzylamine (0.069 g, 0.5 mmol) in benzene (2.5 mL) was prepared at room temperature and was set under an N$_2$ atmosphere. To this mixture, trimethylaluminum (2 M solution in hexane, 0.4 mL, 0.8 mmol) was added via a syringe at 0° C. After 5 min the reaction mixture was allowed to warm to 70° C. and was kept stirring for 16 h at ambient temperature. The cooled mixture was poured into a saturated sodium hydrogen carbonate solution (10 mL) and extracted with chloroform. The phases were separated, the organic solvent was removed in vacuo, and the residue was purified on a silica gel column using chloroform/methanol, (9:1), as the eluent to give 0.075 g (80% yield) of the title compound of the base as a orange yellow solid. The base (0.075 g, 0.16 mmol) was dissolved in chloroform/methanol, (1:1), and treated with HCl in diethyl ether (1 M) at 0° C. followed by addition of diethyl ether. The resulting yellow crystals were collected by filtration and washed with diethyl ether to obtain 0.075 g (86% yield) of the title compound: $^1$H NMR (DMSO-$d_6$, 400 MHz) δ 11.27 (br s, 1H), 10.77 (s, 1H), 8.88 (t, J=5.6 Hz, 1H), 8.26 (s, 1H), 8.11 (s, 1H), 8.07 (d, J=8.8 Hz, 1H), 7.88 (d, J=8.8 Hz, 1H), 7.64 (d, J=8.0 Hz, 1H), 7.28 (t, J=8.0 Hz, 1H), 7.23 (d, J=7.2 Hz, 1H), 7.05 (d, J=8.4 Hz, 1H), 7.00 (d, J=8.4 Hz, 1H), 6.94 (t, J=7.2 Hz, 1H), 4.54 (d, J=5.6 Hz, 2H), 4.28 (br s, 2H), 4.01 (d, J=11.6 Hz, 2H), 3.88 (s, 3H), 3.81 (m, 2H), 3.38 (d, J=11.6 Hz, 2H), 3.13 (m, 2H); MS (EI) m/z 473 (M$^+$+1).

The following Examples, 68-77, were prepared as described for Example 67.

Example 68

2-Hydroxy-3-[5-(morpholin-4-ylmethyl)pyridin-2-yl]-N-[4-(trifluoromethyl)benzyl]-1H-indole-5-carboxamide hydrochloride Starting material: 4-trifluoromethylbenzylamine. Purification on a silica gel column using chloroform/methanol, (9:1), as the eluent, gave the title compound as the base (yellow solid) in 76% yield. The base was treated with HCl in diethyl ether (1 M) to give the title compound. Yield: 88%: $^1$H NMR (DMSO-$d_6$, 400 MHz) δ 11.04 (br s, 1H), 10.76 (s, 1H), is 9.14 (t, J=5.6 Hz, 1H), 8.26 (s, 1H), 8.10 (s, 1H), 8.05 (d, J=8.8 Hz, 1H), 7.87 (d, J=8.8 Hz, 1H), 7.75 (d, J=8.0 Hz, 2H), 7.61 (m, 3H), 7.00 (d, J=8.4 Hz, 1H), 4.65 (d, J=5.6 Hz, 2H), 4.28 (br s, 2H), 4.01 (d, J=11.6 Hz, 2H), 3.79 (m, 2H), 3.39 (d, J=11.6 Hz, 2H), 3.13 (m, 2H); MS (EI) m/z 511 (M$^+$+1).

Example 69

2-Hydroxy-3-[5-(morpholin-4-ylmethyl)pyridin-2-yl]-N-[2-(trifluoromethyl)benzyl]-1H-indole-5-carboxamide hydrochloride Starting material: 2-trifluoromethylbenzylamine. Purification on a silica gel column using chloroform/methanol, (9:1) as the eluent, gave the title compound as the base in 66% yield. The base was treated with HCl in diethyl ether (1 M) to give the title compound. Yield: 82%: $^1$H NMR (DMSO-$d_6$, 400 MHz) δ 11.09 (br s, 1H), 10.78 (s, 1H), 9.12 (t, J=5.6 Hz, 1H), 8.26 (s, 1H), 8.14 (s, 1H), 8.05 (d, J=8.8 Hz, 1H), 7.87 (d, J=8.8 Hz, 1H), 7.77 (d, J=7.6 Hz, 1H), 7.67 (m, 2H), 7.59 (d, J=8.0 Hz, 1H), 7.51 (t, J=7.6 Hz, 1H), 7.03 (d, J=8.4 Hz, 1H), 4.76 (d, J=5.6 Hz, 2H), 4.28 (br s, 2H), 4.01 (d, J=12.0 Hz, 2H), 3.79 (m, 2H), 3.39 (d, J=12.0 Hz, 2H), 3.13 (m, 2H); MS (EI) m/z 511 (M$^+$+1).

Example 70

2-Hydroxy-3-[5-(morpholin-4-ylmethyl)pyridin-2-yl]-N-[2-(trifluoromethoxy)benzyl]-1H-indole-5-carboxamide hydrochloride Starting material: 2-trifluoromethoxybenzylamine. The orange-yellow base (0.058 g, 55% yield) was converted to the title compound. Yield: 83%: $^1$H NMR (CD$_3$OD, 400 MHz) δ 8.17 (s, 1H), 8.13 (s, 1H), 7.91 (s, 2H), 7.65 (d, J=8.4 Hz, 1H), 7.51 (d, J=7.6 Hz, 1H), 7.37 (m, 3H), 7.14 (d, J=8.0 Hz, 1H), 4.72 (s, 2H), 4.34 (s, 2H), 4.13 (d, J=12.4 Hz, 2H), 3.79 (t, J=12.4 Hz, 2H), 3.51 (m, 2H), 3.27 (m, 2H); MS (EI) m/z 527 (M$^+$+1).

Example 71

2-Hydroxy-3-[5-(morpholin-4-ylmethyl)pyridin-2-yl]-N-[4-(trifluoromethoxy)benzyl]-1H-indole-5-carboxamide hydrochloride Starting material: 4-trifluoromethoxybenzylamine. The orange-yellow base was converted to the title compound. Yield: 96%: $^1$H NMR (CD$_3$OD, 400 MHz) δ 8.20 (s, 1H), 8.14 (s, 1H), 7.94 (s, 2H), 7.65 (d, J=8.4 Hz, 1H), 7.51 (d, J=7.2 Hz, 2H), 7.27 (d, J=8.8 Hz, 2H), 7.14 (d, J=8.0 Hz, 1H), 4.65 (s, 2H), 4.34 (s, 2H), 4.12 (d, J=12.4 Hz, 2H), 3.79 (t, J=12.4 Hz, 2H), 3.51 (m, 2H), 3.27 (m, 2H); MS (EI) m/z 527 (M$^+$+1).

Example 72

3-{5-[(Diethylamino)methyl]pyridin-2-yl}-2-hydroxy-N-(2-thienylmethyl)-1H-indole-5-carboxamide hydrochloride Starting materials: methyl 3-{5-[(diethylamino)methyl]pyridin-2-yl}-2-hydroxy-1H-indole-5-carboxylate (0.071 g, 0.2 mmol) and 2-(aminomethyl)thiophene (0.057 g, 0.5 mmol). The base was obtained as an orange-yellow solid (0.043 g, 50% yield), which was transformed to the orange-yellow hydrochloride salt (0.045 g, 89% yield): $^1$H NMR (CD$_3$OD, 400 MHz) δ 8.20 (s, 1H), 8.12 (d, J=1.2 Hz, 1H), 7.94 (s, 2H), 7.61 (dd, J=8.0, 1.6 Hz, 1H), 7.30 (dd, J=5.2, 1.2 Hz, 1H), 7.13 (d, J=8.0 Hz, 1H), 7.07 (m, 1H), 6.98 (dd, J=5.2, 3.6 Hz, 1H), 4.79 (s, 2H), 4.33 (s, 2H), 3.29 (m, 4H), 1.41 (t, J=7.2 Hz, 6H); MS (EI) m/z 435 (M$^+$+1).

Example 73

3-{5-[(Diethylamino)methyl]pyridin-2-yl}-2-hydroxy-N-(pyridin-2-ylmethyl)-1H-indole-5-carboxamide hydrochloride Starting materials: methyl 3-{5-[(diethylamino)methyl]pyridin-2-yl}-2-hydroxy-1H-indole-5-carboxylate (0.071 g, 0.2 mmol) and 2-(aminomethyl)pyridine (0.054 g, 0.5 mmol). The base was obtained as an orange-yellow solid (0.021 g, 24% yield), which was transformed to the orange-yellow hydrochloride salt (0.015 g, 60% yield): $^1$H NMR (CD$_3$OD, 400 MHz) δ 8.81 (d, J=4.8 Hz, 1H), 8.63 (dt, J=8.0, 1.2 Hz, 1H), 8.23 (br s, 2H), 8.15 (d, J=8.0 Hz, 1H), 8.02 (m, 3H), 7.70 (dd, J=8.0, 1.6 Hz, 1H), 7.16 (d, J=8.0 Hz, 1H), 4.97 (s, 2H), 4.34 (s, 2H), 3.29 (m, 4H), 1.41 (t, J=7.2 Hz, 6H); MS (EI) m/z 430 (M$^+$+1).

Example 74

3-{5-[(Diethylamino)methyl]pyridin-2-yl}-2-hydroxy-N-(2-methoxyethyl)-1H-indole-5-carboxamide hydrochloride Starting materials: methyl 3-{5-[(diethylamino)methyl]pyridin-2-yl}-2-hydroxy-1H-indole-5-carboxylate (0.071 g, 0.2 mmol) and 2-methoxyethylamine (0.037 g, 0.5 mmol). The base was obtained as an orange-yellow solid (0.034 g, 43% yield), which was transformed to the orange-yellow hydrochloride salt (0.033 g, 82% yield): $^1$H NMR (CD$_3$OD, 400 MHz) δ 8.26 (s, 1H), 8.13 (s, 1H), 8.00 (s, 2H), 7.60 (dd, J=8.4, 1.6 Hz, 1H), 7.16 (d, J=8.0 Hz, 1H), 4.35 (s, 2H), 3.41 (s, 3H), 3.29 (m, 8H), 1.41 (t, J=7.2 Hz, 6H); MS (EI) m/z 397 (M$^+$+1).

Example 75

2-Hydroxy-3-[5-(morpholin-4-ylmethyl)pyridin-2-yl]-N-(tetrahydrofuran-2-ylmethyl)-1H-indole-5-carboxamide hydrochloride Starting materials: methyl 2-hydroxy-3-[5-(morpholin-4-ylmethyl)pyridin-2-yl]-1H-indole-5-carboxylate and tetrahydrofurfurylamine, but heated at reflux for 2 h. The cooled mixture was poured into a saturated NaHCO$_3$ solution and concentrated in vacuo. The residue was suspended in methanol/dichloromethane, (1:1), silica gel (~2 g) was added and the mixture was re-concentrated in vacuo. The resulting residue was purified on a silica gel column using dichloromethane/methanol, (100:1 to 25:2 and 1% ammonia solution in water (25%)), as the eluent to give the base. Yield: 27%: $^1$H NMR (DMSO-$d_6$, 300 MHz) δ 14.75 (br s, 1H), 11.37 (br s, 1H), 10.69 (s, 1H), 8.50 (t, J=5.51 Hz, 1H), 8.22 (s, 1H), 8.06 (d, J=9.2 Hz, 1H), 7.99 (s, 1H), 7.82 (d, J=9.2 Hz, 1H), 7.54 (d, J=8.1 Hz, 1H), 6.93 (d, J=8.1 Hz, 1H), 4.25 (s, 2H), 4.02-3.60 (m, 6H), 3.44-3.22 (m, 4H), 3.20-3.03 (m, 2H), 1.95-1.78 (m, 4H), 1.70-1.55 (m, 1H); MS (ES) m/z 437 (M$^+$+1). The base was transferred to the hydrochloride.

Example 76

N-Benzyl-2-hydroxy-3-[5-(morpholin-4-ylmethyl)pyridin-2-yl]-1H-indole-5-carboxamide hydrochloride Starting materials: methyl 2-hydroxy-3-[5-(morpholin-4-ylmethyl)pyridin-2-yl]-1H-indole-5-carboxylate and benzylamine. Yield: 52%: $^1$H NMR (DMSO-$d_6$, 300 MHz) δ 14.70 (br s, 1H), 11.31 (br s, 1H), 10.71 (s, 1H), 9.01 (t, J=5.8 Hz, 1H), 8.22 (s, 1H), 8.09-8.00 (m, 2H), 7.83 (d, J=9.3 Hz, 1H), 7.59 (d, J=8.2 Hz, 1H), 7.38-7.18 (m, 5H), 6.95 (d, J=8.2 Hz, 1H), 4.53 (d, J=5.8 Hz, 2H), 4.25 (s, 2H), 4.02-3.71 (m, 4H), 3.37-3.26 (m, 2H), 3.17-2.99 (m, 2H); MS (ES) m/z 443 (M$^+$+1).

Example 77

2-Hydroxy-3-[5-(morpholin-4-ylmethyl)pyridin-2-yl]-N-propyl-1H-indole-5-carboxamide hydrochloride Starting material: methyl 2-hydroxy-3-[5-(morpholin-4-ylmethyl)pyridin-2-yl]-1H-indole-5-carboxylate and propylamine, but was purified on a silica gel column using dichloromethane/methanol, (50:1 to 50:5), as the eluent. Yield: 52%: $^1$H NMR (DMSO-$d_6$, 300 MHz) δ 14.71 (br s, 1H), 11.32 (br s, 1H), 10.68 (s, 1H), 8.40 (t, J=5.6 Hz, 1H), 8.22 (s, 1H), 8.05 (d, J=9.3 Hz, 1H), 7.97 (s, 1H) 7.80 (d, J=9.3 Hz, 1H), 7.53 (d, J=8.1 Hz, 1H), 6.92 (d, J=8.1 Hz, 1H), 4.25 (s, 2H), 4.02-3.83 (m, 2H), 3.81-3.72 (m, 2H), 3.39-3.19 (m, 4H), 3.17-3.02 (m, 2H), 1.63-1.50 (m, 2H), 0.91 (t, J=7.4 Hz, 3H); MS (ES) m/z 395 (M$^+$+1).

Example 78

2-Hydroxy-N-(2-methoxyphenyl)-3-{5-[(4-methylpiperazin-1-yl)sulfonyl]pyridin-2-yl}-1H-indole-5-carboxamide hydrochloride A suspension of methyl 2-hydroxy-3-{5-[(4-methylpiperazin-1-yl)sulfonyl]pyridin-2-yl}-1H-indole-5-carboxylate (0.120 g, 0.28 mmol) and 2-methoxyaniline (0.069 g, 0.56 mmol) in benzene (15 ml) was prepared at room temperature under an $N_2$ atmosphere. To this mixture, trimethylaluminium (2 M solution in heptane, 0.7 mL, 1.4 mmol) was added via a syringe. The mixture was stirred for 5 min at room temperature, and was then allowed to warm to 80° C. and stirred at this temperature for 2 h. The cooled mixture was poured into a saturated sodium hydrogen carbonate solution (20 mL), the aqueous layer was separated and extracted with ethyl acetate (containing 5% methanol). The combined organic layers were dried ($Na_2SO_4$), the solvents were removed in vacuo, and the residue was purified on a silica gel column using dichloromethane/methanol/aqueous $NH_3$, (70:10:1), as the eluent. Fractions, containing product, were concentrated, the solid residue was suspended in ethyl acetate (3 mL), and filtered to give 0.061 g (42% yield) of the title compound as a base. This material was dissolved in chloroform/methanol, (1:1), and treated with HCl in diethyl ether (1 M) followed by addition of diethyl ether. The resulting yellow crystals were collected by filtration and washed with diethyl ether to afford 0.055 g (80% yield) of the title compound: $^1$H NMR (DMSO-$d_6$, 300 MHz) δ 14.61 (br s, 1H), 10.98 (s, 1H), 10.80 is (br s, 1H), 9.34 (s, 1H), 8.53 (s, 1H), 8.13 (s, 1H), 7.80-7.71 (m, 3H), 7.66 (d, J=8.0 Hz, 1H), 7.18 (t, J=7.5 Hz, 1H), 7.10 (d, J=8.0 Hz, 1H), 7.02-6.93 (m, 3H), 3.84 (s, 3H), 3.77-3.72 (m, 2H), 3.51-3.44 (m, 2H), 3.17-3.11 (m, 2H), 3.02-2.96 (m, 2H), 2.76 (s, 3H); MS (ES) m/z 522 (M$^+$+1).

The following Examples, 79-85, were prepared as described for Example 78.

Example 79

2-Hydroxy-N-(4-methoxyphenyl)-3-{5-[(4-methylpiperazin-1-yl)sulfonyl]pyridin-2-yl}-1H-indole-5-carboxamide hydrochloride Starting materials: methyl 2-hydroxy-3-{5-[(4-methylpiperazin-1-yl)sulfonyl]pyridin-2-yl}-1H-indole-5-carboxylate and 4-methoxyaniline. Yield: 43%: $^1$H NMR (DMSO-$d_4$, 300 MHz) δ 14.4 (br s, 1H), 10.96 (br s, 2H), 10.06 (s, 1H), 9.34 (s, 1H), 8.52 (s, 1H), 8.12 (s, 1H), 7.81 (br s, 2H), 7.73-7.65 (m, 3H), 7.02 (d, J=8.0 Hz, 1H), 6.92 (d, J=8.7 Hz, 2H), 3.77-3.72 (m, 5 Et), 3.51-3.43 (m, 2H), 3.18-3.10 (m, 2H), 3.04-2.93 (m, 2H), 2.76 (s, 3H); MS (ES) m/z 522 (M$^+$+1).

Example 80

2-Hydroxy-3-{5-[(4-methylpiperazin-1-yl)sulfonyl]pyridin-2-yl}-N-(pyridin-3-ylmethyl)-1H-indole-5-carboxamide hydrochloride Starting materials: methyl 2-hydroxy-3-{5-[(4-methylpiperazin-1-yl)sulfonyl]pyridin-2-yl}-1H-indole-5-carboxylate and (pyridine-3-ylmethyl)amine, but the reaction mixture was heated at 70° C. for 1 h. The product was purified on a silica gel column using dichloromethane/methanol/aqueous $NH_3$, (100:10:1), as the eluent. Yield: 50%: $^1$H NMR (DMSO-$d_6$, 300 MHz) δ 14.4 (br s, 1H), 11.25 (br s, 1H), 10.96 (s, 1H), 9.55 (t, J=5.3 Hz, 1H), 8.94 (s, 1H), 8.82 (d, J=5.4 Hz, 1H), 8.57 (d, J=8.1 Hz, 1H), 8.52 (s, 1H), 8.22 (br s, 1H), 8.07-7.97 (m, 2H), 7.73 (dd, J=9.5, 1.8 Hz, 1H), 7.65 (d, J=8.2 Hz, 1H), 6.98 (d, J=8.2 Hz, 1H), 4.68 (d, J=5.3 Hz, 2H), 3.77-3.72 (m, 2H), 3.49-3.43 (m, 2H), 3.18-3.12 (m, 2H), 3.04-2.98 (m, 2H), 2.75 (s, 3H); MS (ES) m/z 507 (M$^+$+1).

Example 81

2-Hydroxy-3-{5-[(4-methylpiperazin-1-yl)sulfonyl]pyridin-2-yl}-N-(pyridin-4-ylmethyl)-1H-indole-5-carboxamide hydrochloride Starting materials: methyl 2-hydroxy-3-{5-[(4-methylpiperazin-1-yl)sulfonyl]pyridin-2-yl}-1H-indole-5-carboxylate and (pyridine-4-ylmethyl)amine, but the reaction mixture was heated at 75° C. for 9 h. The product was purified on a silica gel column using dichloromethane/methanol/aqueous $NH_3$, (60:10:1), as the eluent. Yield: 35%: $^1$H NMR (DMSO-$d_6$, 300 MHz) δ 14.5 (br s, 1H), 11.25 (br s, 1H), 10.96 (s, 1H), 9.54 (br s, 1H), 8.84 (d, J=5.7 Hz, 2H), 8.53 (s, 1H), 8.14 (br s, 1H), 8.00-7.95 (m, 3H), 7.73 (d, J=9.0 Hz, 1H), 7.67 (d, J=8.0 Hz, 1H), 7.01 (d, J=8.0 Hz, 1H), 4.68 (s, 2H), 3.76-3.71 (m, 2H), 3.48-3.43 (m, 2H), 3.12-2.98 (m, 4H), 2.75 (s, 3H); MS (ES) m/z 507 (M$^+$+1).

Example 82

2-Hydroxy-3-{5-[(4-methylpiperazin-1-yl)sulfonyl]pyridin-2-yl}-N-(pyridin-2-ylmethyl)-1H-indole-5-carboxamide hydrochloride Starting materials: methyl 2-hydroxy-3-{5-[(4-methylpiperazin-1-yl)sulfonyl]pyridin-2-yl}-1H-indole-5-carboxylate and (pyridine-2-ylmethyl)amine, but the reaction mixture was heated at 80° C. for 24 h. After the first 12 h, an additional 5 eqv. of trimethyl aluminium was added to the reaction mixture. Yield: 40%: $^1$H NMR (DMSO-$d_6$, 300 MHz) δ 14.57 (br s, 1H), 11.24 (br s, 1H), 10.96 (s, 1H), 9.55 (br s, 1H), 8.77 (d, J=5.2 Hz, 1H), 8.50 (s, 1H), 8.38 (t, J=7.7 Hz, 1H), 8.23 (br s, 1H), 7.99 (d, J=9.3 Hz, 1H), 7.90 (d, J=7.7 Hz, 1H), 7.82 (dd, J=7.7, 5.2 Hz, 1H), 7.70 (d, J=9.3 Hz, 1H), 7.64 (d, J=8.0 Hz, 1H), 7.01 (d, J=8.0 Hz, 1H), 4.68 (d, J=4.5 Hz, 2H), 3.76-3.71 (m, 2H), 3.47-3.43 (m, 2H), 3.16-2.98 (m, 4H), 2.73 (s, 3H); MS (ES) m/z 507 (M$^+$+1).

Example 83

N-[2-(Aminosulfonyl)ethyl]-2-hydroxy-3-[5-(morpholin-4-ylmethyl)pyridin-2-yl]-1H-indole-5-carboxamide hydrochloride Starting materials: methyl 2-hydroxy-3-[5-(morpholin-4-ylmethyl)pyridin-2-yl]-1H-indole-5-carboxylate and 2-aminoethanesulfonamide hydrochloride, but the reaction mixture was heated at 80° C. for 22 h. After the first 2 h, an additional 6 eqv. of trimethylaluminium was added to the reaction mixture. The mixture was cooled, diluted with a saturated sodium hydrogen carbonate solution (10 mL) and concentrated in vacuo. The residue was suspended in methanol/dichloromethane, (1:1), silica gel (~2 g) was added and the mixture was re-concentrated in vacuo, resulting in a fine yellow powder that was purified on a silica gel column using dichloromethane/methanol/aqueous NH$_3$, (first 100:10:1, then 70:10:1), as the eluent to afford the title compound as a base in 40% yield: $^1$H NMR (DMSO-d$_6$, 300 MHz) δ 14.5 (br s, 1H), 11.29 (br s, 1H), 10.69 (s, 1H), 8.61 (br s, 1H), 8.22 (s, 1H), 8.04 (d, J=9.0 Hz, 1H), 7.98 (s, 1H), 7.82 (d, J=9.0 Hz, 1H), 7.51 (d, J=8.2 Hz, 1H), 6.96-6.90 (m, 3H), 4.25 (s, 2H), 3.98-3.64 (m, 14H), 3.36-3.22 (m, 4H), 3.12-3.04 (m, 2H); MS (ES) m/z 460 (M$^+$+1). The base was converted to the hydrochloride

Example 84

2-Hydroxy-N-[2-(methylsulfonyl)ethyl]-3-[5-(morpholin-4-ylmethyl)pyridin-2-yl]-1H-indole-5-carboxamide hydrochloride Starting materials: methyl 2-hydroxy-3-[5-(morpholin-4-ylmethyl)pyridin-2-yl]-1H-indole-5-carboxylate and 2-aminoethylmethylsulfone hydrochloride, but the reaction mixture was after cooling diluted with a saturated sodium hydrogen carbonate solution (10 mL) and concentrated in vacuo. The residue was suspended in methanol/dichloromethane (1:1) and silica gel (~2 g) was added. The mixture was re-concentrated in vacuo, resulting in a fine yellow powder that was purified on a silica gel column using dichloromethane/methanol/aqueous NH$_3$, (100:10:1), as the eluent to afford the title compound as a base in 36% yield: $^1$H NMR (DMSO-d$_6$, 300 MHz) δ 14.70 (br s, 1H), 11.42 (br s, 1H), 10.71 (s, 1H), 8.73 (br s, 1H), 8.22 (s, 1H), 8.06 (d, J=9.3 Hz, 1H), 7.99 (s, 1H), 7.82 (d, J=9.3 Hz, 1H), 7.52 (d, J=8.2 Hz, 1H), 6.94 (d, J=8.2 Hz, 1H), 4.25 (s, 2H), 3.98-3.92 (m, 2H), 3.85-3.67 (m, 4H), 3.44-3.29 (m, 4H), 3.12-3.00 (m, 5H); MS (ES) m/z 459 (M$^+$+1). The base was converted to the hydrochloride.

Example 85

3-(4-Cyanopyridin-2-yl)-2-hydroxy-N-(2-methoxyethyl)-1H-indole-5-carboxamide

Starting material: methyl 3-(4-cyanopyridin-2-yl)-2-hydroxy-1H-indole-5-carboxylate and 2-methoxyethanamine. The product was purified on a silica gel column using chloroform/methanol/aqueous NH$_3$, (150:10:1), as the eluent. The combined fractions were concentrated, stirred for 2 h in ethyl acetate (5 mL), and the formed precipitate was filtered off to give 0.012 g (8% yield) of the title compound as a dark-red powder: $^1$H NMR (DMSO-d$_6$, 300 MHz) δ 14.67 (br s, 1H), 10.83 (s, 1H), 8.46 (br s, 1H), 8.16 (d, J=6.3 Hz, 1H), 7.98 (s, 1H), 7.81 (s, 1H), 7.56 (d, J=7.8 Hz, 1H), 6.95 (d, J=7.8 Hz, 1H), 6.86 (d, J=6.3 Hz, 1H), 3.48 (br s, 4H), 3.31 (s, 3H); MS (ES) m/z 337 (M$^+$+1).

Example 86

3-(5-Cyanopyridin-2-yl)-2-hydroxy-N-{2-[(4-methylpiperazin-1-yl)sulfonyl]ethyl}-1H-indole-5-carboxamide hydrochloride Sodium hydride (0.026 g of 60% suspension in mineral oil, 0.65 mmol) was added to a cooled (0° C.) solution of N-{2-[(4-methylpiperazin-1-yl)sulfonyl]ethyl}-2-oxoindoline-5-carboxamide (0.120 g, 33 mmol) in N,N-dimethylformamide (5 mL). The reaction mixture was stirred at 0° C. for 10 min under an N$_2$ atmosphere, followed by the addition of 2-chloro-5-cyanopyridine (0.050 g, 0.36 mmol) in N,N-dimethylformamide (2 mL). The reaction vessel was closed, immediately warmed up to 100° C., and the reaction was stirred at this temperature for 1 h. The cooled mixture was diluted with a saturated sodium hydrogen carbonate solution (5 mL) and concentrated in vacuo. The residue was suspended in methanol/dichloromethane (1:1), silica gel (~2 g) was added and mixture was re-concentrated in vacuo. The solid residue was purified on a silica gel column using dichloromethane/methanol/aqueous NH$_3$, (60:10:1), as the eluent. Fractions containing product were concentrated, the resulting orange foam was suspended in ethyl acetate (3 mL), and filtered to give 0.020 g (13% yield) of the title compound as the base. This material was dissolved in chloroform/methanol, (1:1), and treated with HCl in diethyl ether followed by addition of diethyl ether. The resulting yellow crystals were collected by filtration and washed with diethyl ether to afford 0.014 g (60% yield) of the title compound: $^1$H NMR (DMSO-d$_6$, 300 MHz) δ 14.68 (br s, 1H), 10.94 (s, 1H), 10.55 (br s, 1H), 8.74 (br s, 1H), 8.59 (s, 1H), 8.00 (s, 1H), 7.86 (d, J=9.0 Hz, 1H), 7.70 (d, J=9.0 Hz, 1-H), 7.60 (d, J=8.1 Hz, 1H), 6.98 (d, J=8.1 Hz, 1H), 3.83-3.75 (m, 4H), 3.70-3.62 (m, 2H), 3.52-3.42 (m, 4H), 3.27-3.20 (m, 2H), 3.12-3.05 (m, 2H), 2.75 (s, 3H); MS (ES) m/z 469 (M$^+$+1).

Example 87

2-Hydroxy-3-[5-(morpholin-4-ylmethyl)pyridin-2-yl]-1H-indole-5-carboxamide hydrochloride Sodium hydride (0.090 g of 60% suspension in mineral oil, 2.25 mmol) was added to a cooled (0° C.) solution of 2-oxoindoline-5-carboxamide (0.315 g, 1.79 mmol) in N,N-dimethylformamide (5 mL). The reaction mixture was stirred at 0° C. for 15 min under an N$_2$ atmosphere, followed by the addition of 4-[(6-chloro-1-oxidopyridin-3-yl)methyl]morpholine (0.345 g, 1.51 mmol) in N,N-dimethylformamide (2 mL). The reaction vessel was closed, immediately warmed up to 130° C., and the reaction was stirred at this temperature for 0.5 h. The cooled mixture was diluted with a saturated NaHCO$_3$ solution (30 mL), and extracted with ethyl acetate (containing 5% methanol). The combined organic extracts were dried (Na$_2$SO$_4$), and the solvents were removed in vacuo. The residue was dissolved in toluene (100 mL), and re-evaporated. The material was dried, dissolved in ethyl acetate (75 mL), and phosphorus trichloride (0.6 mL, 6 mmol) in ethyl acetate (5 mL) was added dropwise under vigorous stirring. The reaction mixture was heated to reflux for 2 h, cooled to room temperature, and quenched with an excess of saturated sodium hydrogen carbonate. The organic layer was separated, and the aqueous layer was extracted with ethyl acetate (containing 5% methanol). The combined organic extracts were dried (Na$_2$SO$_4$), the solvents were removed in vacuo, and the residue was purified on a silica gel column using chloroform/methanol/aqueous NH$_3$, (100:10:1), as the eluent to afford the title compound as the base, yield 0.013 g (2.5%). This material was dissolved in chloroform/methanol (1:1), and treated with HCl in diethyl ether (1 M) followed by addition of diethyl ether. The resulting yellow crystals were collected by filtration and washed with diethyl ether to afford 0.010 g of the title compound: $^1$H NMR (DMSO-d$_6$, 300 MHz) δ 14.70 (br s, 1H), 11.08 (br s, 1H), 10.68 (s, 1H), 8.21 (s, 1H), 8.05-7.95 (m, 2H), 7.84 (d, J=9.0 Hz, 1H), 7.56 (d, J=8.0 Hz, 1H), 7.10 (br s, 1H), 6.92 (d, J=8.0 Hz, 1H), 4.26 (s, 2H), 3.97-3.92 (m, 2H), 3.80-3.72 (m, 2H), 3.40-3.33 (m, 2H), 3.13-3.07 (m, 2H); MS (ES) m/z 354 (M$^+$+1).

Example 88

2-Hydroxy-3-{5-[(4-methylpiperazin-1-yl)sulfonyl]pyridin-2-yl}-1H-indole-5-sulfonamide hydrochloride To a mixture of sodium hydride (0.024 g, 0.6 mmol, 60% dispersion in oil, pre-washed with hexane) in N,N-dimethylformamide (1.5 mL) was added 2-oxoindoline-5-sulfonamide (0.212 g, 1.0 mmol; described in: Sun, Li. et al, *J. Med. Chem.* 1999, 42, 5120-5130) in N,N-dimethylformamide (2 mL). The formed mixture was stirred at room temperature for 30 min and 1-[(6-chloropyridin-3-yl)sulfonyl]-4-methylpiperazine (0.92 g, 0.33 mmol; described in: Thunus L. *Annuale Pharmacetiques Francisies,* 1977, 35, 197-203) in N,N-dimethylformamide (2 mL) was added. The obtained solution was heated at 130° C. for 30 min and was then allowed to reach room temperature overnight. The solvent was removed in vacuo and the residue was partitioned between an aqueous sodium hydroxide solution (2 M) and dichloromethane. The combined extracts were evaporated in vacuo and co-evaporated with toluene. The residue was purified on a silica gel column using chloroform/methanol/conc. NH$_3$ (aq), (80:19:1), as the eluent, to afford 0.010 g. The water phase was evaporated in vacuo and purified using the same conditions as above to afford another 0.014 g. The combined solids were dissolved in warm methanol and treated with HCl in diethyl ether (4 M). The hydrochloride salt was dried at 25° C. in vacuo to afford 0.006 g (3% yield) of the title compound: MS (ES) m/z 452 (M$^+$+1).

The following Examples, 89-91, were prepared as described for Example 88.

Example 89

2-Hydroxy-3-{5-[(4-methylpiperazin-1-yl)sulfonyl]pyridin-2-yl}-1H-indole-5-carboxamide hydrochloride Starting materials: 2-oxoindoline-5-carboxamide (0.264 g, 1.5 mmol) and sodium hydride (0.048 g, 1.2 mmol, 60% dispersion in oil, pre-washed with hexane) to afford 0.022 g (4% yield) of title compound: $^1$H NMR (D$_2$O, 400 MHz) δ 8.07 (s, 1H), 7.53 (d, J=8 Hz, 1H), 7.44 (s, 1H), 7.30 (d, J=8 Hz, 1H), 7.13 (d, J=10 Hz, 1H), 6.82 (d, J=8 Hz, 1H), 3.41-3.25 (m, 4H), 3.17-3.03 (m, 4H), 2.67 (br s, 3H).

Example 90

2-Hydroxy-3-{5-[(4-methylpiperazin-1-yl)sulfonyl]pyridin-2-yl}-1H-indole-6-carboxamide hydrochloride Starting materials: 2-oxoindoline-6-carboxamide (0.264 g, 1.5 mmol) and sodium hydride (0.048 g, 1.2 mmol, 60% dispersion in oil, pre-washed with hexane). Work up: the evaporated residue was purified on a silica gel column using methanol as the eluent. Fractions containing product were collected, evaporated in vacuo and purified on another silica gel column using chloroform/methanol/conc. NH$_3$ (aq), (72:24:4), as the eluent to afford 0.050 g of the base. The base was dissolved in methanol/acetone and treated with HCl in diethyl ether (4 M). The hydrochloride salt was dried at 55° C. in vacuo to afford 0.030 g (6% yield) of the title compound: $^1$H NMR (DMSO-d$_6$, 400 MHz) δ 10.84 (s, 1H), 10.65 (br s, 1H), 8.53 (s, 1H), 7.85 (br s, 1H), 7.75-7.67 (m, 2H), 7.60-7.51 (m, 2H), 7.45 (s, 1H), 7.11 (br s, 1H), 3.81-3.64 (m, 2H), 3.52-3.39 (m, 2H), 3.19-3.05 (m, 2H), 3.00-2.85 (m, 2H), 2.76 (s, 3H); MS (TSP) m/z 416 (M$^+$+1).

Example 91

3-[5-({4-[2-(Dimethylamino)ethyl]piperazin-1-yl}sulfonyl)pyridin-2-yl]-2-hydroxy-1H-indole-6-carbonitrile hydrochloride Starting materials: 2-oxoindoline-6-carbonitrile (added at 5-10° C.) and (2-{4-[(6-chloropyridin-3-yl)sulfonyl]piperazin-1-yl}ethyl)-N,N-dimethylamine. Yield: 8%: $^1$H NMR (D$_2$O, 400 MHz) δ 8.19 (s, 1H), 7.74 (d, J=9 Hz, 1H), 7.28 (d, J=9 Hz, 1H), 7.20 (s, 1H), 7.03 (s, 1H), 3.43 (t, J=7 Hz, 2H), 3.34 (m, 4H), 3.20 (t, J=7 Hz, 2H), 3.09 (m, 4H), 2.90 (s, 6H); MS (ES) m/z 455 (M$^+$+1).

Example 92

2-Hydroxy-N-(2-methoxyethyl)-3-(5-nitropyridin-2-yl)-1H-indole-5-carboxamide hydrochloride To a mixture of sodium hydride (0.048 g, 1.2 mmol, 60% dispersion in oil, pre-washed with hexane) in N,N-dimethylformamide (2.5 mL) was added N-(2-methoxyethyl)-2-oxoindoline-5-carboxamide (0.140 g, 0.6 mmol) in N,N-dimethylformamide (1.0 mL) followed by 2-bromo-5-nitropyridine (0.133 g, 0.65 mmol) in N,N-dimethylformamide (1.0 mL). The reaction mixture was stirred at room temperature for 15 min and subsequently heated for 2 h at 90° C. After cooling to room temperature, methanol (5 mL) was added and after 5 min the solvent was removed in vacuo. The residue was purified on a silica gel column using chloroform/methano/conc. NH$_3$ (aq), (72:24:4), as eluent to afford 0.015 g of the base. The base was dissolved in chloroform/methanol and treated with HCl in diethyl ether (4 M). The hydrochloride salt was dried at 50° C. in vacuo over night to afford 6 mg (3% yield) of the title compound: $^1$H NMR (DMSO-d$_6$, 400 MHz) δ 14.56 (br s, 1H), 11.00 (s, 1H), 9.12 (s, 1H), 8.52-8.46 (m, 1H), 8.18 (dd, J=10, 2 Hz, 1H), 8.04 (s, 1H), 7.68 (d, J=10 Hz, 1H), 7.64 (dd, J=8, 1 Hz, 1H), 6.98 (d, J=8 Hz, 1H), 3.50-3.42 (m, 4H), 3.28 (s, 3H); MS (TSP) m/z 357 (M$^+$+1).

Example 93

N-(2-Cyanoethyl)-2-hydroxy-3-[5-(morpholin-4-ylmethyl)pyridin-2-yl]-1H-indole-5-carboxamide hydrochloride To a suspension of sodium hydride (0.043 g, 1.07 mmol, 60% in oil, pre-washed with hexane) in N,N-dimethylformamide (2 mL) was added N-(2-cyanoethyl)-2-oxoindoline-5-carboxamide (0.150 g, 0.65 mmol) in N,N-dimethylformamide (1.0 mL). The mixture was stirred at room temperature for 2 min and 4-[(6-chloro-1-oxidopyridin-3-yl)methyl]morpholine (0.100 g, 0.43 mmol) in N,N-dimethylformamide (2.0 mL) was added. The mixture was heated under an atmosphere of nitrogen at 90° C. for 60 min, was then allowed to cool, and the solvent was removed in vacuo. The residue was purified on a silica gel column using chloroform/methanol/conc. NH$_3$ (aq), (84:14:2), as the eluent to afford 0.10 g. The residue was dissolved in chloroform (5 mL) and a concentrated solution of phosphorus trichloride (0.130 g, 0.95 mmol) in chloroform (1 mL) was added. A precipitate was formed, the mixture was heated at 60° C. for 2 h, and was then allowed to reach room temperature overnight. The solvent was removed in vacuo and the residue was purified on a silica gel column using chloroform/methanol/conc. NH$_3$ (aq), (88:10:2), as the eluent, to afford 5 mg of the base. The base was dissolved in chloroform and treated with HCl in diethyl ether (4 M). The hydrochloride salt was re-crystallized from acetonitrile, dried at 50° C. in vacuo over night to afford 3 mg (1% yield) of the title compound: MS (ES) m/z 406 (M$^+$+1).

Example 94

2-Hydroxy-3-{5-[(4-methylpiperazin-1-yl)sulfonyl]pyridin-2-yl}-1H-indole-5-carbonitrile A mixture of sodium hydride (0.157 g, 3.9 mmol, 60% dispersion in oil, pre-washed with hexane) in N,N-dimethylformamide (2 mL) was added to 2-oxoindoline-5-carbonitrile (0.464 g, 2.9 mmol) in N,N-dimethylformamide (5 mL). The formed brown mixture was stirred at room temperature for 10 min and 1-[(6-chloropyridin-3-yl)sulfonyl]-4-methylpiperazine (0.255 g, 0.92 mmol; described in: Thunus L. *Annuale Pharmaceutiques Francisies*, 1977, 35, 197-203) in N,N-dimethylformamide (3 mL) was added. The obtained red solution was heated at 150° C. for 10 min and was then allowed to reach room temperature overnight. The solvent was removed in vacuo and the residue was partitioned between an aqueous HCl solution (2 M) and ethyl acetate. The aqueous mixture was alkalized to pH 8 by adding sodium hydrogen carbonate (s), and extracted with ethyl acetate (3×10 mL). The combined extracts were dried (Na$_2$SO$_4$), and the solvent was removed in vacuo. The residue was purified on a silica gel column using chloroform/methanol/conc. NH$_3$ (aq), (84:14:2), as an eluent to afford 0.050 g. Further purification was done by preparative HPLC (Xterra column (19×300 mm) with 0.05 M NH$_4$OAc buffer/acetonitrile, (90:10-30:70), as a eluent). Fractions containing product were collected, evaporated in vacuo, and dried at 25° C. in vacuo over night to afford 0.036 g (10% yield) of the title compound: $^1$H NMR (D$_2$O, 400 MHz) δ 8.12 (s, 1H), 7.60 (d, J=10 Hz, 1H), 7.13 (s, 1H), 7.00 (dd, J=8, 2 Hz, 1H), 6.93 (d, J=9 Hz, 1H), 6.73 (dd, J=8, 2 Hz, 1H), 3.91 (d, J=13 Hz, 2H), 3.60 (d, J=11 Hz, 2H), 3.24 (app. t, J=11 Hz, 2H), 3.02 (app. t, J=12 Hz, 2H), 2.89 (s, 3H); MS (TSP) m/z 398 (M$^+$+1).

Example 95

2-Hydroxy-N-[2-(1H-imidazol-4-yl)ethyl]-3-{5-[(4-methylpiperazin-1-yl)sulfonyl]pyridin-2-yl}-1H-indole-5-carboxamide hydrochloride To a mixture of 2-hydroxy-3-{5-[(4-methylpiperazin-1-yl)sulfonyl]pyridin-2-yl}-1H-indole-5-carboxylic acid (0.070 g, 0.17 mmol), O-(benzotriazol-1-yl)-N,N,N',N'-tetramethyluronium tetrafluoroborate (0.060 g, 0.185 mmol), and 1-hydroxybenzotriazole hydrate (0.025 g, 0.185 mmol) in acetonitrile/N,N-dimethylformamide (4 mL, 1:1) was added N,N-diisopropylethylamine (0.110 g, 0.84 mmol) in acetonitrile/N,N-dimethylformamide (1 mL, 1:1). The reaction was stirred at room temperature for 5 min. 2-(1H-Imidazol-4-yl)ethanamine (0.028 g, 0.25 mmol) was added and stirring was continued overnight. The solvents were removed in vacuo and the residue was purified on a silica gel column using chloroform/methanol/conc. NH$_3$ (aq), (80/18/2), as the eluent to afford 0.022 g of the base. The base was dissolved in methanol and treated with HCl in diethyl ether (4 M). The hydrochloride salt was re-crystallized from methanol/ethyl acetate and dried at 55° C. in vacuo over night to afford 0.010 g (10% yield) of the title compound: $^1$H NMR D$_2$O, 400 MHz) δ 8.50 (s, 1H), 8.10 (app. d, J=2 Hz, 1H), 7.64-7.55 (m, 2H), 7.35-7.27 (m, 2H), 7.26 (s, 1H), 6.95 (d, J=8 Hz, 1H), 3.68 (t, J=7 Hz, 2H), 3.47-3.15 (m, 8H), 3.05 (t, J=7 Hz, 2H), 2.76 (s, 3H); MS (ES) m/z 510 (M$^+$+1).

Example 96

N-Benzyl-2-hydroxy-3-{5-[(4-methylpiperazin-1-yl)sulfonyl]pyridin-2-yl}-1H-indole-5-carboxamide hydrochloride Sodium hydride (0.033 g of 60% dispersion in paraffin, 0.84 mmol) was washed with hexane, dried in vacuo and suspended in N,N-dimethylformamide (1 mL). N-Benzyl-2-oxoindoline-5-carboxamide (0.110 g, 0.41 mmol) and 1-[(6-chloropyridin-3-yl)sulfonyl]-4-methylpiperazine (0.170 g, 0.62 mmol; described in: Thunus L. *Annuale Pharmacetiques Francisies*, 1977, 35, 197-203) were dissolved in N,N-dimethylformamide (5 mL) and added to the suspension of sodium hydride. The reaction mixture was stirred at room temperature for 10 min and subsequently heated for 1 h at 90° C. After cooling to room temperature, a saturated aqueous sodium hydrogen carbonate solution was added (4 mL). Silica gel (8 mL) was added and the solvent was removed in vacuo. The residue was purified on a silica gel column using a gradient of chloroform/methanol mixtures, (40:1 to 1:1 and 2% triethylamine), as the eluent. The base was dissolved in a mixture of chloroform (5 mL) and methanol (5 mL). Hydrogen chloride (3 mL, 1 M in diethyl ether) was added and stirring was continued for 10 min. The precipitate was washed with diethyl ether and dried in vacuo at 60° C. to give 0.035 g (16% yield) of the title compound: $^1$H NMR (D$_2$O, 400 MHz) δ 7.79 (m, 1H), 7.42 (m, 4H), 7.37 (m, 1H), 7.24 (m, 1H), 7.14 (m, 2H), 6.80 (m, 1H), 6.68 (m, 1H), 4.50 (s, 2H), 3.77 (m, 2H), 3.60 (m, 2H), 3.22 (m, 2H), 2.91 (m, 5H); MS (ES) m/z 506 (M$^+$+1).

The following Examples, 97-100, were prepared as described for Example 96.

Example 97

2-Hydroxy-3-{5-[(4-methylpiperazin-1-yl)sulfonyl]pyridin-2-yl}-N-propyl-1-indole-5-carboxamide hydrochloride Starting material: 2-oxo-N-propylindoline-5-carboxamide. Yield: 14% of the title compound: $^1$H NMR (D$_2$O, 400

MHz) δ 8.06 (d, J=2 Hz, 1H), 7.49 (dd, J=9, 2 Hz, 1H), 7.40 (m, 1H), 7.26 (m, 1H), 7.11 (m, 1H), 6.83 (d, J=8 Hz, 1H), 3.90 (m, 2H), 3.60 (m, 2H), 3.29 (t, J=7 Hz, 2H), 3.24 (m, 2 Hz), 2.96 (m, 2H), 2.90 (s, 3H), 1.62 (sext, J=7 Hz, 2H), 0.95 (t, J=7 Hz, 3H); MS (ES) m/z 458 (M$^+$+1).

Example 98

2-Hydroxy-N-(2-methoxyethyl)-3-{5-[(4-methylpiperazin-1-yl)sulfonyl]pyridin-2-yl}-1H-indole-5-carboxamide hydrochloride Starting material: N-(2-methoxyethyl)-2-oxoindoline-5-carboxamide. Yield: 12% of the title compound: $^1$H NMR (D$_2$O, 400 MHz) δ 8.06 (d, J=2 Hz, 1H), 7.51 (dd, J=9, 2 Hz, 1H), 7.43 (m, 1H), 7.29 (dd, J=8, 2 Hz, 1H), 7.14 (d, J=9 Hz, 1H), 6.84 (d, J=8 Hz, 1H), 3.92 (m, 2H), 3.70 (t, J=6 Hz, 2H), 3.61 (m, 2H) 3.59 (t, J=5 Hz, 2H), 3.44 (s, 3H) 3.26 (m, 2H), 2.98 (m, 2H), 2.92 (s, 3H); MS (ES) m/z 474 (M$^+$+1).

Example 99

N-[2-(Dimethylamino)ethyl]-2-hydroxy-3-{5-[(4-methylpiperazin-1-yl)sulfonyl]pyridin-2-yl}-1H-indole-5-carboxamide hydrochloride Starting material: N-[2-(dimethylamino)ethyl]-2-oxoindoline-5-carboxamide. The residue was purified on a silica gel column using a gradient chloroform/methanol, (40:1 to 1:1 and 3% triethylamine), as the eluent. Yield: 6% of the title compound: $^1$H NMR (D$_2$O, 400 MHz) δ 8.28 (m, 1H), 7.89 (m, J=2 Hz, 1H), 7.80 (m, 1H), 7.61 (m, 1H), 7.53 (m, 1H), 7.13 (d, J=8 Hz, 1H), 3.94 (m, 2H), 3.83 (t, J=6 Hz, 2H), 3.62 (m, 2H), 3.45 (t, J=6 Hz, 2H), 3.27 (m, 2H), 3.00 (m, 6H), 2.96 (m, 2H), 2.92 (s, 3H); MS (ES) m/z 487 (M$^+$+1).

Example 100

3-(5-Cyanopyridin-2-yl)-2-hydroxy-N-(2-methoxyethyl)-1H-indole-5-carboxamide hydrochloride Starting materials: N-(2-methoxyethyl)-2-oxoindoline-5-carboxamide and 6-chloronicotinonitrile. The residue was purified on a silica gel column using a gradient chloroform/methanol, (100:1 to 10:1), as the eluent. Yield: 28% of the title compound: $^1$H NMR (DMSO-d$_6$, 400 MHz) δ 10.89 (s, 1H), 8.56 (m, 1H), 8.49 (m, 1H), 7.98 (s, 1H), 7.85 (dd, J=10, 2 Hz, 1H), 7.70 (d, J=10 Hz, 1H), 7.59 (dd, J=9, 2 Hz, 1H) 6.96 (d, J=9 Hz, 1H), 3.45 (m, 4H), 3.27 (s, 3H); MS (ES) m/z 337 (M$^+$+1).

Example 101

2-Hydroxy-3-[5-(piperidin-1-ylmethyl)pyridin-2-yl]-1H-indole-5-carboxamide hydrochloride A solution of 1-[(6-chloro-1-oxidopyridin-3-yl)methyl]piperidine (0.147 g, 0.65 mmol) in dry N,N-dimethylformamide (2 mL) was added to a stirred suspension of sodium hydride (0.064 g, 2.6 mmol) in dry N,N-dimethylformamide (2 mL) under an atmosphere of nitrogen. After stirring for 5 min at room temperature, 2-oxoindoline-5-carboxamide (0.175 g, 0.99 mmol) was added in one portion. The resulting mixture was stirred at room temperature for another 15 min and then in a pre-heated oil bath at 110° C. for 2 h. The mixture was allowed to return to room temperature and methanol was added. The solvent was evaporated, the residue was dissolved in ethyl acetate, and phosphorous trichloride (0.90 mL) was added. The resulting mixture was heated at 70° C. for 18 h, and was then allowed to return to room temperature. The pH was adjusted to 7 by the addition of aqueous sodium carbonate and the solvent was evaporated. Purification on a silica gel column using dichloromethane/methanol/triethylamine, (8:2:0.1), as the eluent, gave 0.140 g of the base. The base was dissolved in chloroform/methanol, (9:1), and treated with hydrochloric acid (3.6 mL, 1 M in diethyl ether) and the mixture was stirred at room temperature for 15 min. Diethyl ether was added to give a yellow precipitate that was filtered off and washed with several solvents (chloroform, diethyl ether, ethyl acetate, and methanol) to give 0.026 g (9% yield) of the title compound: $^1$H NMR (CD$_3$OD, 400 MHz) 88.08 (d, J=3 Hz, 2H), 7.84 (m, 2H), 7.59 (m, 1H), 7.05 (d, J=8 Hz, 1H), 4.22 (s, 2H), 3.54 (m, 2H), 2.99 (m, 2H), 1.99 (m, 2H), 1.81 (m, 3H), 1.53 (m, 2H); MS (ES) m/z 351 (M$^+$+1).

Example 102

2-Hydroxy-N-methyl-3-[5-(morpholin-4-ylmethyl)pyridin-2-yl]-1H-indole-5-carboxamide hydrochloride The title compound was prepared as described for Example 101 using 4-[(6-chloro-1-oxidopyridin-3-yl)methyl]morpholine and N-methyl-2-oxoindoline-5-carboxamide. Yield: 12%: $^1$H NMR (D$_2$O, 400 MHz) δ 7.82 (d, J=2 Hz, 1H), 7.58 (dd, J=9, 2 Hz, 1H), 7.45 (br s, 1H), 7.28 (m, 2H), 6.92 (d, J=8 Hz, 1H), 4.16 (s, 2H), 4.12 (m, 2H), 3.79 (m, 2H), 3.46 (m, 2H), 3.24 (m, 2H), 2.90 (s, 3H); MS (TSP) m/z 367 (M$^+$+1).

Example 103

6-Bromo-2-hydroxy-N-methyl-3-{5-[(4-methylpiperazin-1-yl)sulfonyl]pyridin-2-yl}-1H-indole-5-carboxamide hydrochloride A solution of 1-[(6-chloropyridine-3-yl)sulfonyl]-4-methylpiperazine (0.048 g, 0.17 mmol; described in: Thunus L. Annales Pharmaceutiques Francaises 1977, 35, 197-204) and 6-bromo-N-methyl-2-oxoindoline-5-carboxamide (0.47 g, 0.17 mmol) in dry N,N-dimethylformamide (2 mL) was added to a stirred suspension of sodium hydride (0.010 g, 0.41 mmol) in dry N,N-dimethylformamide (0.5 mL) under an atmosphere of nitrogen. The resulting mixture was stirred at room temperature for 20 min and in a pre-heated oil bath, 110° C., for 1.5 h. The mixture was allowed to return to room temperature, the solvent was evaporated, and the residue was purified on a silica gel column using dichloromethane/methanol, (9:1), as the eluent to give 0.045 g of the base. The base was dissolved in dichloromethane/methanol, (9:1), and the solution was treated with hydrochloric acid (0.35 mL, 1 M in diethyl ether). The formed precipitate was filtered off, washed with dichloromethane and diethyl ether, and dried in vacuo to give 0.021 g (21% yield) of the title compound: $^1$H NMR (DMSO-d$_6$, 400 MHz) δ 10.87 (s, 1H), 10.80 (br s, 1H), 8.51 (s, 1H), 8.19 (m, 1H), 7.70 (m, 2H), 7.54 (s, 1H), 7.08 (s, 1H), 3.73 (m, 2H), 3.46 (m, 2H), 3.13 (m, 2H), 2.95 (m, 2H), 2.76 (s, 3H), 2.74 (s, 3H); MS (ES) m/z 508 and 510 (M$^+$+1).

The following Examples, 104-109, were prepared as described for Example 103.

Example 104

6-Bromo-2-hydroxy-N-isopropyl-3-{5-[(4-methylpiperazin-1-yl)sulfonyl]pyridin-2-yl}-1H-indole-5-carboxamide hydrochloride Starting material: 6-bromo-N-isopropyl-2-oxoindoline-5-carboxamide. Yield: 34%: $^1$H NMR (DMSO-d$_6$, 400 MHz) δ

10.84 (s, 1H), 10.50 (br s, 1H), 8.51 (s, 1H), 8.10 (d, J=8 Hz, 1H), 7.74 (dd, J=10, 2 Hz, 1H), 7.65 (m, 1H), 7.48 (s, 1H), 7.07 (s, 1H), 4.05 (m, 1H), 3.73 (m, 2H), 3.47 (m, 2H), 3.13 (m, 2H), 2.91 (m, 2H), 2.77 (s, 3H), 1.16 (d, J=7 Hz, 6H); MS (TSP) m/z 536 and 538 (M$^+$+1).

Example 105

6-Bromo-2-hydroxy-N-(2-methoxyethyl)-3-{5-[(4-methylpiperazin-1-yl)sulfonyl]pyridin-2-yl}-1H-indole-5-carboxamide hydrochloride Starting material: 6-bromo-N-(2-methoxyethyl)-2-oxoindoline-5-carboxamide. Yield: 19%: $^1$H NMR (DMSO-d$_6$, 400 MHz) δ 10.87 (s, 1H), 10.80 (br s, 1H), 8.51 (s, 1H), 8.19 (m, 1H), 7.70 (m, 2H), 7.54 (s, 1H), 7.08 (s, 1H), 3.73 (m, 2H), 3.46 (m, 2H), 3.32 (m, 5H), 2.75 (m, 5H); MS (ES) m/z 552 and 554 (M$^+$+1).

Example 106

6-Bromo-2-hydroxy-3-{5-[(4-methylpiperazin-1-yl)sulfonyl]pyridin-2-yl}-N-(tetrahydrofuran-2-ylmethyl)-1H-indole-5-carboxamide hydrochloride Starting material: 6-bromo-2-oxo-N-(tetrahydrofuran-2-ylmethyl)indoline-5-carboxamide. Yield: 32%: $^1$H NMR (D$_2$O, 400 MHz) δ 8.21 (d, J=2 Hz, 1H), 7.69 (m, 1H), 7.13 (s, 1H), 7.12 (m, 1H), 6.77 (s, 1H), 4.26 (m, 1H), 3.96 (m, 2H), 3.87 (m, 2H), 3.63 (m, 3H), 3.47 (m, 1H), 3.27 (m, 2H), 3.06 (m, 2H), 2.93 (s, 3H), 2.17 (m, 1H), 2.02 (m, 2H), 1.77 (m, 1H); MS (ES) m/z 578 and 580 (M$^+$+1).

Example 107

6-Bromo-2-hydroxy-3-{5-[(4-methylpiperazin-1-yl)sulfonyl]pyridin-2-yl}-N-(2-pyrrolidin-1-ylethyl)-1H-indole-5-carboxamide hydrochloride Starting material: 6-bromo-2-oxo-N-(2-pyrrolidin-1-ylethyl)indoline-5-carboxamide. Yield: 11%: $^1$H NMR (D$_2$O, 400 MHz) δ 8.27 (d, J=2 Hz, 1H), 7.78 (m, 1H), 7.41 (s, 1H), 7.35 (m, 1H), 7.09 (s, 1H), 3.95 (m, 2H), 3.83 (m, 2H), 3.75 (m, 2H), 3.62 (m, 2H), 3.55 (m, 2H), 3.24 (m, 4H), 3.03 (m, 2H), 2.92 (s, 3H), 2.20 (m, 2H), 2.06 (m, 2H); MS (ES) m/z 591 and 593 (M$^+$+1).

Example 108

N-[3-(Dimethylamino)propyl]-2-hydroxy-3-{5-[(4-methylpiperazin-1-yl)sulfonyl]pyridin-2-yl}-1H-indole-5-carboxamide hydrochloride Starting material: N-[3-(dimethylamino)propyl]-2-oxoindoline-5-carboxamide. Yield: 32%: $^1$H NMR (D$_2$O, 400 MHz) δ 8.07 (d, J=2 Hz, 1H), 7.58 (m, 2H), 7.39 (dd, J=8, 2 is Hz, 1H), 7.28 (d, J=10 Hz, 1H), 6.96 (d, J=8 Hz, 1H), 3.90 (m, 2H), 3.62 (m, 2H), 3.49 (m, 2H), 3.25 (m, 4H), 2.94 (m, 2H), 2.92 (s, 6H), 2.90 (s, 3H), 2.08 (m, 2H); MS (ES) m/z 501 (M$^+$+1).

Example 109

2-Hydroxy-N-(2-methoxyethyl)-3-[5-(morpholin-4-ylsulfonyl)pyridin-2-yl]-1H-indole-5-carboxamide hydrochloride Starting materials: 4-[(6-chloropyridin-3-yl)sulfonyl]morpholine and N-(2-methoxyethyl)-2-oxoindoline-5-carboxamide. Yield: 7%: $^1$H NMR (DMSO-d, 400 MHz) δ 10.85 (s, 1H), 8.45 (m, 2H), 7.99 (s, 1H), 7.74 (s, 2H), 7.58 (m, 1H), 6.94 (d, J=8 Hz, 1H), 3.65 (m, 4H), 3.45 (m, 4H), 3.27 (s, 3H), 3.00 (m, 4H); MS (ES) m/z 461 (M$^+$+1).

Example 110

2-Hydroxy-3-{5-[(4-methylpiperazin-1-yl)sulfonyl]pyridin-2-yl}-N-pyridin-3-yl-1H-indole-5-carboxamide hydrochloride Trimethylaluminium (0.505 mL, 1.01 mmol) was added to a suspension of methyl 2-hydroxy-3-{5-[(4-methylpiperazin-1-yl)sulfonyl]pyridin-2-yl}-1H-indole-5-carboxylate (0.110 g, 0.26 mmol) and 3-aminopyridine (0.024 g, 0.25 mmol) in dry dichloromethane (5 mL), under an atmosphere of nitrogen. The resulting mixture was stirred at room temperature for 10 min and at reflux for 16 h. Water was added, the solid was filtered off, and washed with chloroform. The combined organic phases were evaporated and the residue was purified on a silica gel column using dichloromethane/methanol, (9:1), as the eluent, to give 0.029 g of the base. The base was suspended in dichlormethane/methanol, (9:1), and hydrochloric acid (0.20 mL, 1 M in diethyl ether) was added to give a clear solution and then a yellow precipitate. The solid was filtered off, washed with dichloromethane and diethyl ether, and dried in vacuo to give 0.028 g, (19% yield) of the title compound: $^1$H NMR (D$_2$O, 400 MHz) δ 9.34 (d, J=3 Hz, 1H), 8.61 (m, 1H), 8.53 (d, J=6 Hz, 1H) 8.16 (d, J=2 Hz, 1H), 8.01 (dd, J=9, 6 Hz, 1H), 7.75 (d, J=1 Hz, 1H), 7.67 (dd, J=10, 2 Hz, 1H), 7.58 (dd, J=8, 2 Hz, 1H), 7.44 (d, J=10 Hz, 1H), 7.03 (d, J=8 Hz, 1H), 3.87 (m, 2H), 3.60 (m, 2H), 3.23 (m, 2H), 2.94 (m, 2H), 2 90 (s, 3H); MS (ES) m/z 493 (M$^+$+1).

Example 111

2-Hydroxy-N-(2-methoxybenzylamide)-3-{5-[(4-methylpiperazin-1-yl)sulfon]pyridin-2-yl}-1H-indole-5-carboxamide hydrochloride To an anhydrous solution of 1-[(6-chloropyridine-3-yl)sulfonyl]-4-methylpiperazine (0.057 g, 0.32 mmol; described in: Thunus L., *Annales Pharmaceutiques Francaises* 1977, 35, 197-204) and sodium hydride (0.019 g, 0.80 mmol) in N-methylpyrrolidinone (1.0 mL) under an atmosphere of nitrogen, was added N-(2-methoxybenzyl)-2-oxoindoline-5-carboxamide (0.079 g, 2.67 mmol). The reaction was stirred at room temperature until the gas evolution ceased (20 min), and then heated at 80° C. over night. Aqueous work-up was followed by purification on a silica gel column using methylene chloride/methanol/triethylamine, (90:10:1 to 75:25:1), as the eluent. The substance was further purified by preparative HPLC (Xterra column (19×300 mm) with 0.05 M NH$_4$OAc buffer/acetonitrile, (90:10-30:70), as the eluent) to give 0.009 g (6% yield) of the yellow title compound as the base: $^1$H NMR (CD$_3$OD, 400 MHz) δ 6.83 (br s, 1H), 6.55 (br s, 1H), 6.25 (m, 2H), 6.09 (d, J=8 Hz, 1H), 5.72 (m, 2H), 5.53 (d, J=9 Hz, 1H), 5.44 (d, J=8 Hz, 1H), 5.37 (t, J=8 Hz, 1H), 3.07 (s, 2H), 2.35 (s, 3H), 1.61 (br s, 4H), 1.02 (br s, 4H), 0.76 (s, 3H); MS (ES) m/z 536 (M$^+$+1), m/z 534 (M$^-$−1). The solid was dissolved in a dichloromethane and a small volume of methanol (5 mL total volume). HCl in diethyl ether (1.0 M) was added until acidic pH. The solvent volume was reduced under vacuum. The precipitated hydrochloride salt was filtered and dried id vacuo affording the title compound.

The following Examples, 112-114, were prepared as described for Example 111.

Example 112

2-Hydroxy-N-(3-methoxybenzylamide)-3-{5-[(4-methylpiperazin-1-yl)sulfon]pyridin-2-yl}-1H-indole-5-carboxamide hydrochloride Starting material: N-(3-methoxybenzyl)-2-oxoindoline-5-carboxamide. Yield: 7%: $^1$H NMR (CD$_3$OD, 400 MHz) δ 8.48 (s, 2H), 8.32 (s, 1H), 8.04 (s, 1H), 7.75-7.68 (m, 2H), 7.61 (d, J=8 Hz, 1H), 7.19 (t, J=8 Hz, 1H), 7.03 (d, J=8 Hz, 1H), 6.92-6.89 (m, 2H), 6.78 (d, J=7 Hz, 1H), 4.54 (s, 2H), 3.73 (s, 3H), 3.11 (br s, 4H), 2.51 (br s, 4H), 2.26 (s, 3H); MS (ES) m/z 536 (M$^+$+1), m/z 534 (M$^-$−1). The substance was subsequently converted into the hydrochloride.

Example 113

2-Hydroxy-3-{5-[(4-methylpiperazin-1-yl)sulfon]pyridin-2-yl}-N-(tetrahydro-2H-pyran-4-yl)-1H-indole-5-carboxamide hydrochloride Starting material: 2-oxo-N-(tetrahydro-2H-pyran-4-yl)indoline-5-carboxamide. Yield: 17%: $^1$H NMR (DMSO-d$_6$, 400 MHz) δ 10.85 (s, 1H), 8.45 (s, 1H), 8.14 (br s, 1H), 7.94 (br s, 1H), 7.77 (br s, 1H), 7.69 (br s, 1H), 7.57 (br s, 1H), 6.92 (br s, 1H), 3.90 (d, J=11 Hz, 2H), 3.39 (t, J=11 Hz, 2H), 3.00 (br s, 4H), 2.38 (br s, 4H), 2.32 (m, 1H), 2.06 (s, 3H), 1.76 (d, J=11 Hz, 2H), 1.62 (m, 2H); MS (ES) m/z 500 (M$^+$+1), m/z 498 (M$^-$−1). The substance was subsequently converted into the hydrochloride.

Example 114

2-Hydroxy-N-(4-methoxybenzylamide)-3-{5-[(4-methylpiperazin-1-yl)sulfon]pyridin-2-yl}-1H-indole-5-carboxamide hydrochloride Starting materials: N-(4-methoxybenzyl)-2-oxoindoline-5-carboxamide and 4-[(6-chloro-1-oxidopyridin-3-yl)methyl]morpholine. The product was purified on a silica gel column using dichloromethane/methanol/triethylamine, (90:10:1), as the eluent. The product fractions were dried under vacuum and taken up in dry dichloromethane, to which was added phosphorus trichloride (0.104 mL, 1.20 mmol). After stirring at 60° C. for 1 h, the reaction was extracted under basic conditions and purified by preparative HPLC (Xterra column (19×300 mm) with 0.05 M NH$_4$OAc buffer/acetonitrile, (90:10-30:70), as the eluent). Total yield: 7%: $^1$H NMR (CD$_3$OD, 400 MHz) δ 8.03 (s, 1H), 7.90 (s, 1H), 7.82 (s, 2H), 7.54 (d, J=9 Hz, 1H), 7.30 (d, J=8 Hz, 2H), 7.05 (d, J=9 Hz, 1H), 6.88 (d, J=10 Hz, 2H), 4.53 (d, 2H), 3.75 (s, 3H), 3.69 (br s, 4H), 3.41 (s, 2H), 2.47 (br s, 4H); MS (ES) m/z 473 (M$^+$+1), m/z 471 (M$^-$−1). The substance was subsequently converted into the hydrochloride.

Example 115

N-(Cyanomethyl)-2-hydroxy-3-[5-(morpholin-4-ylmethyl)pyridin-2-yl]-1H-indole-5-carboxamide hydrochloride To a solution of methyl 2-hydroxy-3-[5-(morpholin-4-ylmethyl)pyridin-2-yl]-1H-indole-5-carboxylate (0.090 g, 0.245 mmol), trimethylaluminum (0.98 mL, 1.96 mmol), and triethylamine (0.10 mL, 0.74 mmol) in benzene (4.0 mL) under nitrogen atmosphere, was added aminoacetonitrile hydrochloride (0.056 g, 0.61 mmol). The reaction mixture was stirred at 60° C. overnight. The reaction was extracted with dichloromethane and brine, dried over sodium sulfate and evaporated to dryness. The residue was subsequently purified by preparative HPLC (Xterra C$_{18}$ column (19×300 mm) with 0.05 M NH$_4$OAc buffer/acteonitrile) to give 8.6 mg (9% yield) of the yellow base: MS (ES) m/z 392 (M$^+$+1). The base was dissolved in a dichloromethane and a small volume of methanol (5 mL total volume.) and HCl in diethyl ether (1.0 M) was added until acidic pH. The solvent volume was reduced under vacuum. The precipitated hydrochloride salt was filtered and dried in vacuo affording the title compound.

Example 116

N-(2-Furylmethyl)-2-hydroxy-3-[5-(morpholin-4-ylmethyl)pyridin-2-yl]-1H-indole-5-carboxamide hydrochloride The title compound was prepared as described for Example 115 using methyl 2-hydroxy-3-[5-(morpholin-4-ylmethyl)pyridin-2-yl]-1H-indole-5-carboxylate. Yield: 44%: $^1$H NMR (CD$_3$OD, 400 MHz) δ 7.98 (s, 1H), 7.88 (s, 1H), 7.81 (s, 2H), 7.49 (d, J=8 Hz, 1H), 7.38 (s, 1H), 6.99 (d, J=8 Hz, 1H) 6.28 (d, J=21 Hz, 2H), 4.54 (s, 2H), 3.56 (br s, 4H), 3.39 (s, 2H), 2.44 (br s, 4H); MS (ES) m/z 433 (M$^+$+1). The substance was subsequently converted into the hydrochloride.

Example 117

2-Hydroxy-3-{5-[(4-methylpiperazin-1-yl)methyl]pyridin-2-yl}-1H-indole-6-carbonitrile hydrochloride To a suspension of 1-[(6-chloro-1-oxidopyridin-3-yl)methyl]-4-methylpiperazine (0.145 g, 0.60 mmol) and 2-oxoindoline-6-carbonitrile (0.100 g, 0.63 mmol) in tetrahydrofuran (3 mL), was added sodium bis(trimethylsilyl)amide (1.4 mL, 1.4 mmol). The mixture was stirred for 5 min at room temperature and then heated in a microwave oven at 110° C. for 10 min. The mixture was quenched with methanol (2 mL) followed by evaporation to dryness. The dry product mixture was dissolved in ethyl acetate/acetonitrile, (1:1, 5 mL), is and phosphorus trichloride (0.5 mL, 5.73 mmol) was added. The mixture was stirred at 60° C. for 3 h and then concentrated in vacuo. The residue was purified on a silica gel column using a gradient dichloromethane/methanol, (100:1 to 2:1), as the eluent. The resulting yellow solid was dissolved in dichloromethane/methanol, (9:1), and treated with HCl in diethyl ether (1 M) at 0° C. The resulting yellow crystals were collected by filtration and washed with diethyl ether to obtain 0.025 g (9% yield) of the title compound: MS (ESP) m/z 348 (M$^+$+1).

Example 118

2-Hydroxy-3-[5-(piperidin-1-ylmethyl)pyridin-2-yl]-1H-indole-6-carbonitrile hydrochloride The title compound was prepared as described for Example 117. Starting material: 1-[(6-chloro-1-oxidopyridin-3-yl)methyl]piperidine (0.136 g, 0.60 mmol) and 2-oxoindoline-6-carbonitrile (0.100 g, 0.63 mmol) and sodium bis(trimethylsilyl)amide (1.4 mL, 1.4 mmol). Yield: 0.031 g, 12%: $^1$H NMR D$_2$O, 400 MHz) δ 8.01 (d, J=2 Hz, 1H), 7.75 (dd, J=9, 2 Hz, 1H), 7.28 (d, J=9 Hz, 1H), 7.06 (m, 2H), 6.92 (s, 1H), 4.19 (s, 2H), 3.53 (m, 2H), 2.98 (m, 2H), 1.94 (s, 2H), 1.82 (m, 1H), 1.70 (m, 2H), 1.46 (m, 1H); MS (ESP) m/z 349 (M$^+$+1).

Example 119

2-Hydroxy-3-{5-[(3-oxopiperazin-1-yl)methyl]pyridin-2-yl}-1H-indole-6-carbonitrile hydrochloride 2-Oxoindoline-6-carbonitrile (0.063 g, 0.397 mmol) was added to a suspension of 4-[(6-chloro-1-oxidopyridin-3-yl)methyl]piperazin-2-one (0.080 g, 0.33 mmol) and sodium hydride (0.042 g, 1.75 mmol) in 1-methyl-2-pyrrolidone (3 mL). The mixture was stirred at room temperature for 10 min, heated at 90° C. for 1 h and finally quenched with methanol (0.5 mL). Trituration with acetonitrile and drying in vacuo gave the crude 2-hydroxy-3-{1-oxido-5-[(3-oxopiperazin-1-yl)methyl]pyridin-2-yl}-1H-indole-6-carbonitrile as a solid. The crude intermediate was suspended in chloroform (5 mL) and phosphorus trichloride (0.5 mL, 5.73 mmol) was added. The mixture was stirred at 60° C. for 3 h and then concentrated in vacuo. Purification using preparative HPLC (XTerra®PrepMS C8 column 10 μm, 30×150 mm; 0.1 M NH$_4$OAc buffer/acetonitrile, (80:20-20:80), as the eluent) gave a yellow solid that was dissolved in dichloromethane/methanol, (9:1), and treated with HCl in diethyl ether (1 M) at 0° C. The resulting yellow crystals were collected by filtration, washed with diethyl ether, and dried to obtain 0.036 g (26% yield) of the title compound: $^1$H NMR (D$_2$O, 400 MHz) 8.16 (d, J=2 Hz, 1H), 7.96 (dd, J=9, 2 Hz, 1H), 7.80 (d, J=9 Hz, 1H), 7.61 (d, J=8 Hz, 1H), 7.35 (dd, J=8, 1 Hz, 1H), 7.31 (s, 1H), 4.11 (s, 2H), 3.62 (s, 2H), 3.51 (t, J=5H, 2H); MS (ESP) m/z 348 (M$^+$+1).

Example 120

2-Hydroxy-3-[6-(2-morpholin-4-ylethoxy)pyrimidin-4-yl]-1H-indole-6-carbonitrile hydrochloride A mixture of 4-{2-[(6-chloropyrimidin-4-yl)oxy]ethyl}morpholine (0.116 g, 0.47 mmol), 2-oxoindoline-6-carbonitrile (0.075 g, 0.47 mmol) and cesium carbonate (0.46 g, 1.42 mmol) in butyronitrile (3 mL), was heated in a microwave oven at 160° C. for 10 min. The crude product was purified using preparative HPLC (XTerra®PrepMS C8 column 10 μm, 30×150 mm; 0.1 M NH$_4$OAc buffer/acetonitrile, (80:20-20:80), as the eluent). The acetonitrile was evaporated and the remaining aqueous phase was extracted with chloroform and evaporated in vacuo to give a yellow solid. The solid was dissolved in dichloromethane/methanol, (9:1), and treated with HCl in diethyl ether (1 M) at 0° C. The resulting yellow crystals were collected by filtration, washed with diethyl ether, and dried to obtain 0.036 g (17% yield) of the title compound: $^1$H NMR (D$_2$O, 400 MHz) δ 8.31 (s, 1H), 7.15 (dd, J=8, 2 Hz, 1H), 6.96 (d, J=8 Hz, 1H), 6.93 (d, J=2 Hz, 1H), 6.01 (s, 1H), 4.67 (m, 2H), 4.17 (m, 2H), 3.94 (m, 2H), 3.75 (m, 2H), 3.66 (m, 2H), 3.40 (m, 2H); MS (ESP) m/z 366 (M$^+$+1).

Example 121

3-{6-[2-(Diisopropylamino)ethoxy]pyrimidin-4-yl}-2-hydroxy-1H-indole-6-carbonitrile hydrochloride The title compound was prepared as described for Example 120 using N-{2-[(6-chloropyrimidin-4-yl)oxy]ethyl}-N-isopropylpropan-2-amine (0.10 g, 0.39 mmol), 2-oxoindoline-6-carbonitrile (0.074 g, 0.47 mmol) and cesium carbonate (0.50 g, 1.54 mmol). Yield 0.026 g, 15%: $^1$H NMR (CD$_3$OD, 400 MHz) δ 8.59 (s, 1H), 7.81 (d, J=8 Hz, 1H), 7.55 (d, J=1 Hz, 1H), 7.45 (dd, J=8, 1 Hz, 1H), 6.64 (s, 1H), 4.40 (t, J=6 Hz, 1H), 3.87 (m, 1H), 3.58 (t, J=6 Hz, 1H), 1.44 (m, 3H); MS (ESP) m/z 380 (M$^+$+1).

Example 122

2-Hydroxy-3-{5-[(4-methylpiperazin-1-yl)sulfonyl]pyridin-2-yl}-1H-indole-5-carboxylic acid hydrochloride To a mixture of 2-hydroxy-3-{5-[(4-methylpiperazin-1-yl)sulfonyl]pyridin-2-yl}-1H-indole-5-carbonitrile (0.100 g, 0.25 mmol) in water (2 mL) was added 1 M aqueous sodium hydroxide solution (1.3 mL, 1.3 mmol) followed by water (1 mL) in a microwave vial. The mixture was subjected to microwave irradiation for 15 min at 140° C. The pH was adjusted to 5 with HCl (aq) (2 M). The solid was collected by filtration, washed with diethyl ether, and dried to afford 0.110 g (89% yield) of the title compound: MS (ESP) m/z 417 (M$^+$+1).

Example 123

2-Hydroxy-3-{5-[(4-methylpiperazin-1-yl)sulfonyl]pyridin-2-yl}-N-[3-(2-oxopyrrolidin-1-yl)propyl]-1H-indole-5-carboxamide hydrochloride 2-Hydroxy-3-{5-[(4-methylpiperazin-1-yl)sulfonyl]pyridin-2-yl}-1H-indole-5-carboxylic acid (0.050 g, 0.12 mmol), O-(benzotriazol-1-yl)-N,N,N',N'-tetramethyluronium tetrafluoroborate (0.042 g, 0.13 mmol), 1-hydroxybenzotriazole hydrate (0.018 g, 0.13 mmol) and N,N-diisopropylethylamine (0.150 mL, 0.86 mmol) were suspended in N,N-dimethylformamide (3 mL), and stirred at room temperature for 30 min. 1-(3-Aminopropyl)pyrrolidin-2-one (0.034 g, 0.24 mmol) was added and stirring was continued for 1 h. The solvent was removed in vacuo and the residue was purified using preparative HPLC (XTerra®PrepMS C8 column 10 μm, 30×150 mm; 0.1 M NH$_4$OAc buffer/acetonitrile, (80:20-20:80), as the eluent) to give a yellow/red solid that was dissolved in dichloromethane/methanol (1:1), and treated with HCl in diethyl ether (1 M) at 0° C. The resulting yellow crystals were collected by filtration and washed with diethyl ether to obtain 9 mg (12% yield) of the title compound: $^1$H NMR (D$_2$O, 400 MHz) δ 1.89 (dd, J=14.0, 7.2 Hz, 2H) 2.04 (m, 2H) 2.42 (t, J=8.2 Hz, 2H) 2.91 (d, J=4.8 Hz, 3H) 2.99 (m, 2H) 3.25 (m, 2H) 3.37 (m, 4H) 3.53 (t, J=7.2 Hz, 2H) 3.65 (d, 2H) 3.91 (d, 2H) 6.96 (d, J=8.3 Hz, 1H) 7.35 (m, 2H) 7.62 (m, 2H) 8.15 (d, J=2.0 Hz, 1H); MS (EP) m/z 541 (M$^+$+1).

The following Examples, 124-133, were prepared as described for Example 123.

Example 124

2-Hydroxy-3-{5-[(4-methylpiperazin-1-yl)sulfonyl]pyridin-2-yl}-N-(2-thienylmethyl)-1H-indole-5-carboxamide hydrochloride Starting material: (2-thienylmethyl)amine. Yield: 16% as a solid: $^1$H NMR (D$_2$O, 400 MHz) 88.15 (d, J=2 Hz, 1H), 7.67 (m, 1H), 7.51 (dd, J=10, 2 Hz, 1H), 7.33 (d, J=8 Hz, 1H), 7.30 (dd, J=5, 1 Hz, 1H), 7.05 (d, J=3 Hz, 1H), 6.97 (m, 1H), 6.90

(d, J=8 Hz, 1H), 3.86 (m, 2H), 3.55 (m, 2H), 3.20 (m, 2H), 2.93 (m, 2H), 2.87 (s, 3H); MS (ESP) m/z 512 (M$^+$+1).

Example 125

2-Hydroxy-3-{5-[(4-methylpiperazin-1-yl)sulfonyl]pyridin-2-yl}-N-[2-(2-oxoimidazolidin-1-yl)ethyl]-1H-indole-5-carboxamide hydrochloride Starting material: 1-(2-aminoethyl)imidazolidin-2-one. Yield: 11% as a solid $^1$H NMR (D$_2$O, 400 MHz) δ 8.11 (d, J=2 Hz, 1H), 7.61 (dd, J=9, 2 Hz, 1H), 7.56 (s, 1H), 7.34 (m, 2H), 6.95 (d, J=8 Hz, 1H), 3.90 (m, 2H), 3.60 (m, 6H), 3.42 (m, 4H), 3.26 (m, 2H), 2.94 (m, 2H), 2.91 (s, 3H); MS (ESP) m/z 528 (M$^+$+1).

Example 126

2-Hydroxy-3-[5-(4-methylpiperazine-1-sulfonyl)pyridin-2-yl]-1H-indole-5-carboxylic acid (2-carbamoylethyl)amide Starting material: δ-alaninamide. Yield: 12% as a solid: $^1$H NMR (D$_2$O, 400 MHz) δ 8.03 (d, J=2 Hz, 1H), 7.48 (dd, J=9, 2 Hz, 1H), 7.33 (s, 1H), 7.23 (d, J=8 Hz, 1H), 7.05 (d, J=10 Hz, 1H), 6.79 (d, J=8 Hz, 1H), 3.91 (d, J=13 Hz, 2H), 3.63 (m, 4H), 3.26 (m, 2H), 2.99 (m, 2H), 2.92 (s, 3H), 2.63 (t, J=7 Hz, 2H); MS (ESP) m/z 487 (M$^+$+1).

Example 127

2-Hydroxy-3-{5-[(4-methylpiperazin-1-yl)sulfonyl]pyridin-2-yl}-N-[2-(2-thienyl)ethyl]-1H-indole-5-carboxamide hydrochloride Starting material: [2-(2-thienyl)ethyl]amine. Yield: 18% as a solid: $^1$H NMR (CD$_3$OD, 400 MHz) δ 8.41 (d, J=2 Hz, 1H), 8.01 (s, 1H), 7.79 (m, 2H), 7.56 (dd, J=8, 1 Hz, 1H), 7.21 (d, J=4 Hz, 1H), 7.05 (d, J=8 Hz, 1H), 6.93 (m, 2H), 3.97 (d, J=14 Hz, 2H), 3.65 (m, 4H), 3.23 (m, 2H), 3.17 (t, J=7 Hz, 2H), 2.97 (m, 2H), 2.94 (s, 3H); MS (ESP) m/z 526 (M$^+$+1).

Example 128

N-[2-(Acetylamino)ethyl]-2-hydroxy-3-{5-[(4-methylpiperazin-1-yl)sulfonyl]pyridin-2-yl}-1H-indole-5-carboxamide hydrochloride Starting material: N-(2-aminoethyl)acetamide. Yield: 22% as a solid $^1$H NMR (CD$_3$OD, 400 MHz) δ 8.41 (s, 1H), 8.03 (d, J=2 Hz, 1H), 7.81 (d, J=2 Hz, 2H), 7.58 (dd, J=8, 2 Hz, 1H), 7.06 (d, J=8 Hz, 1H), 3.97 (d, J=13 Hz, 2H), 3.62 (d, J=13 Hz, 2H), 3.52 (t, J=6 Hz, 2H), 3.44 (t, J=6 Hz, 2H), 3.24 (m, 2H), 2.99 (m, 2H), 2.93 (m, 3H), 1.95 (m, 3H); MS (ESP) m/z 501 (M$^+$+1).

Example 129

N-(2-Cyanoethyl)-2-hydroxy-3-{5-[(4-methylpiperazin-1-yl)sulfonyl]pyridin-2-yl}-1H-indole-5-carboxamide hydrochloride Starting material: 3-aminopropanenitrile. Yield: 11% as a solid: $^1$H NMR (D$_2$O, 400 MHz) δ 8.07 (d, J=2 Hz, 1H), 7.54 (d, J=2 Hz, 1H), 7.48 (s, 1H), 7.34 (d, J=8 Hz, 1H), 7.14 (d, J=9 Hz, 1H), 6.89 (d, J=8 Hz, 1H), 3.92 (m, 2H), 3.69 (t, J=6 Hz, 2H), 3.62 (m, 2H), 3.26 (m, 2H), 2.98 (m, 2H), 2.91 (s, 3H), 2.89 (m, 2H); MS (ESP) m/z 469 (M$^+$+1).

Example 130

N-[2-(Aminosulfonyl)ethyl]-2-hydroxy-3-{5-[(4-methylpiperazin-1-yl)sulfonyl]pyridin-2-yl}-1H-indole-5-carboxamide hydrochloride Starting material: 2-aminoethanesulfonamide. Yield: 24% as a solid: $^1$H NMR (400 MHz, DMSO-d$_6$) δ 10.91 (s, 1H), 10.71 (s, 1H), 8.63 (s, 1H), 8.51 (s, 1H), 8.01 (s, 1H), 7.76 (s, 2H), 7.57 (dd, J=8, 1 Hz, 1H), 6.96 (m, 3H), 3.97 (m, 4H), 3.74 (d, J=12 Hz, 2H), 3.66 (m, 2H), 3.47 (s, 3H), 3.25 (m, 2H), 3.14 (m, 2H), 2.95 (m, 2H), 2.77 (d, J=3 Hz, 3H); MS (ESP) m/z 523 (M$^+$+1).

Example 131

N-(Cyanomethyl)-2-hydroxy-3-{5-[(4-methylpiperazin-1-yl)sulfonyl]pyridin-2-yl}-1H-indole-5-carboxamide hydrochloride Starting material: aminoacetonitrile. Yield: 17% as a solid: $^1$H NMR (DMSO-d$_6$, 400 MHz) δ 11.04 (m, 1H), 10.93 (s, 1H), 8.95 (t, J=6 Hz, 1H), 8.51 (s, 1H), 8.07 (s, 1H), 7.75 (m, 2H), 7.61 (m, 1H), 6.98 (m, 1H), 4.02 (d, J=6 Hz, 2H), 3.74 (d, J=12 Hz, 2H), 3.65 (s, 2H), 3.46 (d, J=12 Hz, 2H), 3.12 (m, 2H), 3.00 (m, 2H), 2.75 (d, J=4 Hz, 3H); MS (ESP) m/z 455 (M$^+$+1).

Example 132

2-Hydroxy-3-[5-(4-methylpiperazine-1-sulfonyl)pyridin-2-yl]-1H-indole-5-carboxylic acid carbamoylmethylamide hydrochloride Starting material: glycinamide. Yield: 24% as a solid: $^1$H NMR (DMSO-d$_6$, 400 MHz) δ 10.91 (s, 1H), 10.71 (m, 1H), 8.64 (t, J=6 Hz, 1H), 8.50 (s, 1H), 8.06 (s, 1H), 7.76 (m, 2H), 7.61 (dd, J=8, 2 Hz, 1H), 7.35 (s, 1H), 6.98 (m, 2H), 3.83 (d, J=6 Hz, 2H), 3.74 (d, J=12 Hz, 2H), 3.46 (m, 2H), 3.15 (m, 2H), 2.96 (m, 2H), 2.76 (d, J=3 Hz, 31H): MS (ESP) m/z 473 (M$^+$+1).

Example 133

2-Hydroxy-3-{5-[(4-methylpiperazin-1-yl)sulfonyl]pyridin-2-yl}-N-[2-(methylsulfonyl)ethyl]-1H-indole-5-carboxamide hydrochloride Starting material: [2-(methylsulfonyl)ethyl]amine. Yield: 11% as a solid: $^1$H NMR (DMSO-d$_6$, 400 MHz) δ 10.92 (s, 1H), 9.99 (m, 1H), 8.64 (s, 1H), 8.51 (s, 1H), 7.99 (s, 1H), 7.78 (m, 1H), 7.71 (d, J=9 Hz, 1H), 7.57 (dd, J=8, 1 Hz, 1H), 6.97 (d, J=8 Hz, 1H), 3.50 (m, 2H), 3.76 (m, 2H), 3.39 (t, J=7 Hz, 1H), 3.33 (s, 3H), 3.04 (s, 2H), 2.88 (m, 2H), 2.79 (s, 2H); MS (ESP) m/z 522 (M$^+$+1).

Example 134

Methyl 3-fluoro-3-[5-(morpholin-4-ylmethyl)pyridin-2-yl]-2-oxoindoline-5-carboxylate hydrochloride Methyl 2-hydroxy-3-[5-(morpholin-4-ylmethyl)pyridin-2-yl]-1H-indole-5-carboxylate (0.074 g, 0.2 mmol) was dissolved in a tetrahydrofuran/dioxane (10 mL, 1:1) mixture under N$_2$ atmosphere and stirred at −20° C. for 5 min. To this solution, sodium bis(trimethylsilyl)amide (1 M solution in tetrahydrofuran, 0.20 mL, 0.2 mmol) was added via a syringe and the reaction mixture was allowed to stir for 20 min at 0° C. To this mixture 1-fluoro-2,4,6-trimethylpyridinium triflate was added as a solid and the reaction was allowed to warm up to room temperature and stirred for 16 h. The solvent was removed in vacuo and the residue was purified on a silica gel column using chloroform/methanol, (9:1), as the eluent. The product was further purified by preparative HPLC (XTerra®PrepMS C8 column 10 μm, 19×300 mm; 0.1 M NH$_4$OAc buffer/acetonitrile, (from 9:1 to 1:1), as eluent gradient) affording 0.020 g (26% yield) of the base as an orange-yellow oil. The base (0.020 g, 0.05 mmol) was dissolved in chloroform/methanol, (1:1), and treated with 1 M hydrochloric acid in diethyl ether at 0° C. The resulting yellow crystals were collected by vacuum filtration and washed with diethyl ether to obtain 0.016 g (70% yield) of the title compound. $^1$H NMR (DMSO-d$_6$, 400 MHz) δ 11.47 (s, 1H), 8.70 (s, 1H), 8.33 (d, J=8.0 Hz, 1H), 8.07 (d, J=8.4 Hz, 1H), 8.03 (d, J=7.6 Hz, 1H), 7.56 (s, 1H), 7.17 (d, J=8.0 Hz, 1H), 4.43 (s, 2H), 3.98 (d, J=12.4 Hz, 2H), 3.82 (s, 3H), 3.76 (m, 2H), 3.30 (d, J=12.4 Hz, 2H), 3.15 (m, 2H; MS (EI) m/z 386 (M$^+$+1).

Example 135

2-Hydroxy-3-[5-(4-methyl-piperazin-1-ylmethyl)-pyridin-2-yl]-1H-indole-5-carboxylic acid methyl ester The title compound was prepared as described for Example 46 using 1-[(6-chloro-1-oxidopyridin-3-yl)methyl]-4-methylpiperazine (0.967 g, 4.0 mmol) as the starting material. The product was obtained as an orange yellow solid (0.140 g, 9% yield): $^1$H NMR (CD$_3$OD, 400 MHz) δ 8.18 (s, 1H), 7.98 (s, 1H), 7.93 (dd, J=8.8, 1.6 Hz, 1H), 7.77 (d, J=9.2 Hz, 1H), 7.73 (dd, J=8.0, 1.6 Hz, 1H), 7.09 (d, J=8.4 Hz, 1H), 3.93 (s, 3H), 3.49 (s, 2H), 2.58 (br s, 8H), 2.33 (s, 3H); MS (EI) m/z 381 (M$^+$+1).

Example 136

2-Hydroxy-3-[5-(4-methyl-piperazin-1-ylmethyl)-pyridin-2-yl]-1H-indole-5-carboxylic acid (thiophen-2-ylmethyl)-amide dihydrochloride The title compound was prepared as described for Example 67 using 2-hydroxy-3-[5-(4-methyl-piperazin-1-ylmethyl)-pyridin-2-yl]-1H-indole-5-carboxylic acid methyl ester (0.057 g, 0.15 mmol) and 2-(aminomethyl)-thiophene (0.042 g, 0.38 mmol) as starting materials. The base was obtained as an orange yellow solid (0.032 g, 46% yield), which was transformed to the orange yellow dihydrochloride (0.026 g, 70% yield): $^1$H NMR (CD$_3$OD, 400 MHz) δ 8.27 (s, 1H), 8.16 (d, J=1.2 Hz, 1H), 8.11 (dd, J=8.8, 1.6 Hz, 1H), 8.03 (d, J=9.2 Hz, 1H), 7.64 (dd, J=8.0, 1.6 Hz, 1H), 7.31 (dd, J=5.2, 1.6 Hz, 1H), 7.18 (d, J=8.4 Hz, 1H), 7.08 (dd, J=3.6, 1.2 Hz, 1H), 6.98 (dd, J=5.2, 3.6 Hz, 1H), 4.80 (s, 2H), 4.24 (s, 2H), 3.6 (br s, 8H), 3.02 (s, 3H); MS (EI) m/z 462 (M$^+$+1).

Example 137

2-Hydroxy-3-[5-(4-methyl-piperazin-1-ylmethyl)-pyridin-2-yl]-1H-indole-5-carboxylic acid benzylamide dihydrochloride The title compound was prepared as described for Example 67 using 2-hydroxy-3-[5-(4-methyl-piperazin-1-ylmethyl)-pyridin-2-yl]-1H-indole-5-carboxylic acid methyl ester and benzylamine (0.041 g, 0.38 mmol). The base was obtained as an orange yellow oil (0.030 g, 44% yield), which was transformed to the orange yellow dihydrochloride (0.029 g, 83% yield): $^1$H NMR (CD$_3$OD, 400 MHz) δ 8.27 (s, 1H), 8.19 (d, J=0.8 Hz, 1H), 8.09 (dd, J=9.2, 2.0 Hz, 1H), 8.03 (d, J=9.2 Hz, 1H), 7.67 (dd, J=8.0, 1.6 Hz, 1H), 7.48 (s, 1H), 7.43 (d, J=7.6 Hz, 1H), 7.36 (t, J=7.2 Hz, 2H), 7.28 (d, J=7.2 Hz, 1H), 7.19 (d, J=8.4 Hz, 1H), 4.66 (s, 2H), 4.16 (s, 2H), 3.6 (bs, 8H), 3.02 (s, 3H); MS (EI) m/z 456 (M$^+$+1).

Example 138

3-(5-Diethylaminomethyl-pyridin-2-yl)-2-hydroxy-1H-indole-5-carboxylic acid (2-methanesulfonyl-ethyl)-amide hydrochloride The title compound was prepared as described for Example 67 using methyl 3-{5-[(diethylamino)methyl]pyridin-2-yl}-2-hydroxy-1H-indole-5-carboxylate (0.071 g, 0.2 mmol) and (2-aminoethyl)methylsulfone hydrochloride (0.080 g, 0.5 mmol) as starting materials. The base was obtained after preparative HPLC purification (XTerra®PrepMS C$_8$ columns 10 μm, 19×300 mm; 0.1 M NH$_4$OAc buffer/acetonitrile, from 90:10 to 40:60, as eluent gradient) as an orange yellow solid (0.030 g, 34% yield), which was transformed to the yellow hydrochloride salt (0.023 g, 72% yield): $^1$H NMR (CD$_3$OD, 400 MHz) δ 8.21 (s, 1H), 8.11 (s, 1H), 7.95 (s, 2H), 7.60 (dd, J=8.0, 1.2 Hz, 1H), 7.14 (d, J=8.0 Hz, 1H), 4.35 (s, 2H), 3.93 (t, J=6.4 Hz, 2H), 3.51 (t, J=6.4 Hz, 2H), 3.29 (m, 4H), 3.09 (s, 3H), 1.43 (t, J=7.2 Hz, 6H); MS (EI) m/z 445 (M$^+$+1).

Pharmaceutical Compositions

According to one aspect of the present invention there is provided a pharmaceutical composition comprising a compound of formula Ia or Ib, as a free base or a pharmaceutically acceptable salt, solvate or solvate of salt thereof, for use in the prevention and/or treatment of conditions associated with glycogen synthase kinase-3.

The composition may be in a form suitable for oral administration, for example as a tablet, for parenteral injection as a sterile solution or suspension. In general the above compositions may be prepared in a conventional manner using pharmaceutically carriers or diluents. Suitable daily doses of the compounds of formula Ia or Ib in the treatment of a mammal, including man, are approximately 0.01 to 250 mg/kg bodyweight at peroral administration and about 0.001 to 250 mg/kg bodyweight at parenteral administration. The typical daily dose of the active ingredients varies within a wide range and will depend on various factors such as the relevant indication, the route of administration, the age, weight and sex of the patient and may be determined by a physician.

A compound of formula Ia or Ib, or a salt thereof, can be used on its own but will usually be administered in the form of a pharmaceutical composition in which the formula Ia or Ib compound/salt/solvate (active ingredient) is in association with a pharmaceutically acceptable diluent or carrier. Dependent on the mode of administration, the pharmaceutical composition may comprise from 0.05 to 99% w (percent by weight), for example from 0.10 to 50% w, of active ingredient, all percentages by weight being based on total composition.

A diluent or carrier includes water, aqueous polyethylene glycol, magnesium carbonate, magnesium stearate, talc, a sugar (such as lactose), pectin, dextrin, starch, tragacanth, microcrystalline cellulose, methyl cellulose, sodium carboxymethyl cellulose or cocoa butter.

A composition of the invention can be in tablet or injectable form. The tablet may additionally comprise a disintegrant and/or may be coated (for example with an enteric coating or coated with a coating agent such as hydroxypropyl methylcellulose).

The invention further provides a process for the preparation of a pharmaceutical composition of the invention which comprises mixing a compound of formula Ia or Ib, or a pharmaceutically acceptable salt, solvate or solvate of salt thereof, a hereinbefore defined, with a pharmaceutically acceptable diluent or carrier.

An example of a pharmaceutical composition of the invention is an injectable solution containing a compound of the invention, or a pharmaceutically acceptable salt, solvate or solvate of salt thereof, as hereinbefore defined, and sterile water, and, if necessary, either sodium hydroxide or hydrochloric acid to bring the pH of the final composition to about pH 5, and optionally a surfactant to aid dissolution.

Liquid solution comprising a compound of formula Ia or Ib, or a salt thereof, dissolved in water.

| Solution | mg/mL |
|---|---|
| Compound X | 5.0% w/v |
| Pure water | To 100% |

Medical Use

Surprisingly, it has been found that the compounds defined in the present invention, as a free base or a pharmaceutically acceptable salt, solvate or solvate of salt thereof, are well suited for inhibiting glycogen synthase kinase-3 (GSK3). Accordingly, the compounds of the present invention are expected to be useful in the prevention and/or treatment of conditions associated with glycogen synthase kinase-3 activity, i.e. the compounds may be used to produce an inhibitory effect of GSK3 in mammals, including man, in need of such prevention and/or treatment.

GSK3 is highly expressed in the central and peripheral nervous system and in other tissues. Thus, it is expected that compounds of the invention are well suited for the prevention and/or treatment of conditions associated with glycogen synthase kinase-3 in the central and peripheral nervous system. In particular, the compounds of the invention are expected to be suitable for prevention and/or treatment of conditions associated with especially, dementia, Alzheimer's Disease, Parkinson's Disease, Frontotemporal dementia Parkinson's Type, Parkinson dementia complex of Guam, HIV dementia, diseases with associated neurofibrillar tangle pathologies and dementia pugilistica.

Other conditions are selected from the group consisting of amyotrophic lateral sclerosis, corticobasal degeneration, Down syndrome, Huntington's Disease, postencephelatic parkinsonism, progressive supranuclear palsy, Pick's Disease, Niemann-Pick's Disease, stroke, head trauma and other chronic neurodegenerative diseases, Bipolar Disease, affective disorders, depression, schizophrenia, cognitive disorders, hair loss and contraceptive medication.

Further conditions are selected from the group consisting predemented states, Mild Cognitive Impairment, Age-Associated Memory Impairment, Age-Related Cognitive Decline, Cognitive Impairement No Dementia, mild cognitive decline, mild neurocognitive decline, Late-Life Forgetfulness, memory impairment and cognitive impairment, vascular dementia, dementia with Lewy bodies and androgenetic alopecia.

One embodiment of the invention relates to the prevention and/or treatment of dementia and Alzheimer's Disease.

Another embodiment of the invention relates to the prevention and/or treatment of bone-related disorders.

The dose required for the therapeutic or preventive treatment of a particular disease will necessarily be varied depending on the host treated, the route of administration and the severity of the illness being treated.

The present invention relates also to the use of a compound of formula Ia or Ib as defined hereinbefore, in the manufacture of a medicament for the prevention and/or treatment of conditions associated with glycogen synthase kinase-3.

In the context of the present specification, the term "therapy" also includes "prevention" unless there are specific indications to the contrary. The terms "therapeutic" and "therapeutically" should be construed accordingly.

The invention also provides for a method of treatment and/or prevention of conditions associated with glycogen synthase kinase-3 comprising administering to a mammal, including man in need of such treatment and/or prevention a therapeutically effective amount of a compound of formula Ia or Ib, as hereinbefore defined.

Non-Medical Use

In addition to their use in therapeutic medicine, the compounds of formula Ia or Ib as a free base or a pharmaceutically acceptable salt thereof, are also useful as pharmacological tools in the development and standardisation of in vitro and in vivo test systems for the evaluation of the effects of inhibitors of GSK3 related activity in laboratory animals such as cats, dogs, rabbits, monkeys, rats and mice, as part of the search for new therapeutics agents.

Pharmacology

Determination of ATP Competition in Scintillation Proximity GSK3β Assay.

GSK3β Scintillation Proximity Assay.

The competition experiments were carried out in duplicate with 10 different concentrations of the inhibitors in clear-bottom microtiter plates (Wallac, Finland). A biotinylated peptide substrate, Biotin-Ala-Ala-Glu-Glu-Leu-Asp-Ser-Arg-Ala-Gly-Ser(PO$_3$H$_2$)-Pro-Gln-Leu (AstraZeneca, Lund), was added at a final concentration of 1 μM in an assay buffer containing 1 mU recombinant human GSK3β (Dundee University, UK), 12 mM morpholinepropanesulfonic acid (MOPS), pH 7.0, 0.3 mM EDTA, 0.01% β-mercaptoethanol, 0.004% Brij 35 (a natural detergent), 0.5% glycerol and 0.5 μg BSA/25 μl. The reaction was initiated by the addition of 0.04 μCi [γ-$^{33}$P]ATP (Amersham, UK) and unlabelled ATP at a final concentration of 1 μM and assay volume of 25 μl. After incubation for 20 minutes at room temperature, each reaction was terminated by the addition of 25 μl stop solution containing 5 mM EDTA, 50 μM ATP, 0.1% Triton X-100 and 0.25 mg streptavidin coated Scintillation Proximity Assay (SPA) beads (Amersham, UK). After 6 hours the radioactivity was determined in a liquid scintillation counter (1450 MicroBeta Trilux, Wallac). The inhibition curves were analysed by non-linear regression using GraphPad Prism, USA. The $K_m$ value of ATP for GSK3β, used to calculate the inhibition constants ($K_i$) of the various compounds, was 20 μM.

The following abbreviations have been used:

MOPS Morpholinepropanesulfonic acid

EDTA Ethylenediaminetetraacetic acid

BSA Bovin Serum Albumin

ATP Adenosine Triphosphate

SPA Scintillation Proximity Assay

GSK3 Glycogen synthase kinase 3

Results

Typical K$_i$ values for the compounds of the present invention are in the range of about 0.001 to about 10,000 nM. Other values for K$_i$ are in the range of about 0.001 to about 300 nM.

The invention claimed is:

1. A compound having the formula Ia;

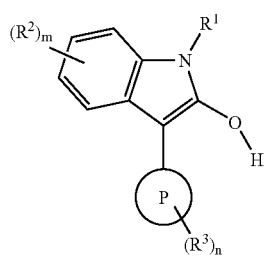

P represents a 6-membered heteroaromatic ring containing one or two heteroatoms;
R$^1$ is hydrogen;
R$^2$ is cyano;
R$^3$ is (SO$_2$)NR$^4$R$^5$;
wherein R$^4$ and R$^5$ may together form a 4-, 5-, 6- or 7-membered heterocyclic group containing one or more heteroatoms selected independently from N, O and S, wherein said heterocyclic group is substituted by a group Y;
R$^8$ and R$^9$ are independently selected from: hydrogen and C$_{1-6}$alkyl or R$^8$ and R$^9$ may together form a 5- or 6-membered heterocyclic group containing one or more heteroatoms, selected independently from N, O and S;
Y is selected from: oxo, C$_{2-6}$alkylOR$^8$, C$_{0-6}$alkylheteroaryl, OR$^8$ and C$_{2-6}$alkylNR$^8$R$^9$;
m is 1;
n is 1;
or a salt, or a tautomer thereof.

2. A compound according to claim 1, wherein P is pyridine.

3. A compound according to claim 1 selected from:
3-[5-({4-[2-(Dipropylamino)ethyl]piperazin-1-yl}sulfonyl)pyridin-2-yl]-2-hydroxy-1H-indole-6-carbonitrile hydrochloride;
2-Hydroxy-3-(5-{[4-(2-morpholin-4-ylethyl)piperazin-1-yl]sulfonyl}pyridin-2-yl)-1H-indole-6-carbonitrile hydrochloride;
2-Hydroxy-3-(5-{[4-(2-pyrrolidin-1-ylethyl)piperazin-1-yl]sulfonyl}pyridin-2-yl)-1H-indole-6-carbonitrile hydrochloride;
2-Hydroxy-3-(5-{[4-(2-methoxyethyl)piperazin-1-yl]sulfonyl}pyridin-2-yl)-1H-indole-6-carbonitrile hydrochloride, or
3-[5-({4-[2-(Dimethylamino)ethyl]piperazin-1-yl}sulfonyl)pyridin-2-yl]-2-hydroxy-1H-indole-6-carbonitrile hydrochloride;
or a tautomer thereof, or a free base of any of foregoing hydrochloride or a pharmaceutically acceptable salt of any said free base.

4. A pharmaceutical formulation comprising as an active ingredient a therapeutically effective amount of a compound according to claim 1 or 3 in association with at least one pharmaceutically acceptable carrier or diluent.

5. A method of treatment of a human suffering from Alzheimer's Disease, by administering to such a human, a therapeutically effective amount of a compound of formula Ia as defined in claim 1 or 3.

6. A compound selected from:
2-Hydroxy-3-{5-[(4-methylpiperazin-1-yl)carbonyl]pyridin-2-yl}-1H-indole-6-carbonitrile hydrochloride;
6-(6-Cyano-2-hydroxy-1H-indol-3-yl)-N-(2-morpholin-4-ylethyl)nicotinamide hydrochloride;
6-(6-Cyano-2-hydroxy-1H-indol-3-yl)-N-methyl-N-(2-pyrrolidin-1-ylethyl)nicotinamide hydrochloride;
6-(6-Cyano-2-hydroxy-1H-indol-3-yl)-N-(2-(dimethylamino)ethyl)-N-methylnicotinamide hydrochloride;
6-(6-Cyano-2-hydroxy-1H-indol-3-yl)-N-(2-pyrrolidin-1-ylethyl)pyridine-3-sulfonamide hydrochloride;
2-Hydroxy-3-[5-(piperazine-1-sulfonyl)pyridin-2-yl]-1H-indole-6-carbonitrile hydrochloride;
2-Hydroxy-N-(2-methoxyethyl)-3-[5-(morpholin-4-ylmethyl)pyridin-2-yl]-1H-indole-5-carboxamide hydrochloride;
2-Hydroxy-3-[5-(morpholin-4-ylmethyl)pyridin-2-yl]-N-(pyridin-2-ylmethyl)-1H-indole-5-carboxamide hydrochloride;
2-Hydroxy-3-[5-(morpholin-4-ylmethyl)pyridin-2-yl]-N-(2-thienylmethyl)-1H-indole-5-carboxamide hydrochloride;
2-Hydroxy-3-[5-(morpholin-4-ylmethyl)pyridin-2-yl]-N-[2-(2-oxoimidazolidin-1-yl)ethyl]-1H-indole-5-carboxamide hydrochloride;
N-[2-(Acetylamino)ethyl]-2-hydroxy-3-[5-(morpholin-4-ylmethyl)pyridin-2-yl]-1H-indole-5-carboxamide hydrochloride;
2-Hydroxy-N-(2-methoxybenzyl)-3-[5-(morpholin-4-ylmethyl)pyridin-2-yl]-1H-indole-5-carboxamide hydrochloride;
2-Hydroxy-3-[5-(morpholin-4-ylmethyl)pyridin-2-yl]-N-[4-(trifluoromethyl)benzyl]-1H-indole-5-carboxamide hydrochloride;
2-Hydroxy-3-[5-(morpholin-4-ylmethyl)pyridin-2-yl]-N-[2-(trifluoromethyl)benzyl]-1H-indole-5-carboxamide hydrochloride;
2-Hydroxy-3-[5-(morpholin-4-ylmethyl)pyridin-2-yl]-N-[2-(trifluoromethoxy)benzyl]-1H-indole-5-carboxamide hydrochloride;
2-Hydroxy-3-[5-(morpholin-4-ylmethyl)pyridin-2-yl]-N-[4-(trifluoromethoxy)benzyl]-1H-indole-5-carboxamide hydrochloride;
3-{5-[(Diethylamino)methyl]pyridin-2-yl}-2-hydroxy-N-(2-thienylmethyl)-1H-indole-5-carboxamide hydrochloride;
3-{5-[(Diethylamino)methyl]pyridin-2-yl}-2-hydroxy-N-(pyridin-2-ylmethyl)-1H-indole-5-carboxamide hydrochloride;
3-{5-[(Diethylamino)methyl]pyridin-2-yl}-2-hydroxy-N-(2-methoxyethyl)-1H-indole-5-carboxamide hydrochloride;
2-Hydroxy-3-[5-(morpholin-4-ylmethyl)pyridin-2-yl]-N-(tetrahydrofuran-2-ylmethyl)-1H-indole-5-carboxamide hydrochloride;
N-Benzyl-2-hydroxy-3-[5-(morpholin-4-ylmethyl)pyridin-2-yl]-1H-indole-5-carboxamide hydrochloride;
2-Hydroxy-3-[5-(morpholin-4-ylmethyl)pyridin-2-yl]-N-propyl-1H-indole-5-carboxamide hydrochloride:
2-Hydroxy-N-(2-methoxyphenyl)-3-{5-[(4-methylpiperazin-1-yl)sulfonyl]pyridin-2-yl}-1H-indole-5-carboxamide hydrochloride;
2-Hydroxy-N-(4-methoxyphenyl)-3-{5-[(4-methylpiperazin-1-yl)sulfonyl]pyridin-2-yl}-1H-indole-5-carboxamide hydrochloride;

2-Hydroxy-3-{5-[(4-methylpiperazin-1-yl)sulfonyl]pyridin-2-yl}-N-(pyridin-3-ylmethyl)-1H-indole-5-carboxamide hydrochloride;
2-Hydroxy-3-{5-[(4-methylpiperazin-1-yl)sulfonyl]pyridin-2-yl}-N-(pyridin-4-ylmethyl)-1H-indole-5-carboxamide hydrochloride;
2-Hydroxy-3-{5-[(4-methylpiperazin-1-yl)sulfonyl]pyridin-2-yl}-N-(pyridin-2-ylmethyl)-1H-indole-5-carboxamide hydrochloride;
N-[2-(Aminosulfonyl)ethyl]-2-hydroxy-3-[5-(morpholin-4-ylmethyl)pyridin-2-yl]-1H-indole-5-carboxamide hydrochloride;
2-Hydroxy-N-[2-(methylsulfonyl)ethyl]-3-[5-(morpholin-4-ylmethyl)pyridin-2-yl]-1H-indole-5-carboxamide hydrochloride;
3-(5-Cyanopyridin-2-yl)-2-hydroxy-N-{2-[(4-methylpiperazin-1-yl)sulfonyl]ethyl}-1H-indole-5-carboxamide hydrochloride;
2-Hydroxy-3-[5-(morpholin-4-ylmethyl)pyridin-2-yl]-1H-indole-5-carboxamide hydrochloride;
2-Hydroxy-3-{5-[(4-methylpiperazin-1-yl)sulfonyl]pyridin-2-yl}-1H-indole-5-sulfonamide hydrochloride;
2-Hydroxy-3-{5-[(4-methylpiperazin-1-yl)sulfonyl]pyridin-2-yl}-1H-indole-5-carboxamide hydrochloride;
2-Hydroxy-3-{5-[(4-methylpiperazin-1-yl)sulfonyl]pyridin-2-yl}-1H-indole-6-carboxamide hydrochloride;
2-Hydroxy-N-(2-methoxyethyl)-3-(5-nitropyridin-2-yl)-1H-indole-5-carboxamide hydrochloride;
N-(2-Cyanoethyl)-2-hydroxy-3-[5-(morpholin-4-ylmethyl)pyridin-2-yl]-1H-indole-5-carboxamide hydrochloride;
2-Hydroxy-N-[2-(1H-imidazol-4-yl)ethyl]-3-{5-[(4-methylpiperazin-1-yl)sulfonyl]pyridin-2-yl}-1H-indole-5-carboxamide hydrochloride;
N-Benzyl-2-hydroxy-3-{5-[(4-methylpiperazin-1-yl)sulfonyl]pyridin-2-yl}-1H-indole-5-carboxamide hydrochloride;
2-Hydroxy-3-{5-[(4-methylpiperazin-1-yl)sulfonyl]pyridin-2-yl}-N-propyl-1H-indole-5-carboxamide hydrochloride;
2-Hydroxy-N-(2-methoxyethyl)-3-{5-[(4-methylpiperazin-1-yl)sulfonyl]pyridin-2-yl}-1H-indole-5-carboxamide hydrochloride;
N-[2-(Dimethylamino)ethyl]-2-hydroxy-3-{5-[(4-methylpiperazin-1-yl)sulfonyl]pyridin-2-yl}-1H-indole-5-carboxamide hydrochloride;
3-(5-Cyanopyridin-2-yl)-2-hydroxy-N-(2-methoxyethyl)-1H-indole-5-carboxamide hydrochloride;
2-Hydroxy-3-[5-(piperidin-1-ylmethyl)pyridin-2-yl]-1H-indole-5-carboxamide hydrochloride;
2-Hydroxy-N-methyl-3-[5-(morpholin-4-ylmethyl)pyridin-2-yl]-1H-indole-5-carboxamide hydrochloride;
6-Bromo-2-hydroxy-N-methyl-3-{5-[(4-methylpiperazin-1-yl)sulfonyl]pyridin-2-yl}-1H-indole-5-carboxamide hydrochloride;
6-Bromo-2-hydroxy-N-isopropyl-3-{5-[(4-methylpiperazin-1-yl)sulfonyl]pyridin-2-yl}-1H-indole-5-carboxamide hydrochloride;
6-Bromo-2-hydroxy-N-(2-methoxyethyl)-3-{5-[(4-methylpiperazin-1-yl)sulfonyl]pyridin-2-yl}-1H-indole-5-carboxamide hydrochloride;
6-Bromo-2-hydroxy-3-{5-[(4-methylpiperazin-1-yl)sulfonyl]pyridin-2-yl}-N-(tetrahydrofuran-2-ylmethyl)-1H-indole-5-carboxamide hydrochloride;
6-Bromo-2-hydroxy-3-{5-[(4-methylpiperazin-1-yl)sulfonyl]pyridin-2-yl}-N-(2-pyrrolidin-1-ylethyl)-1H-indole-5-carboxamide hydrochloride;
N-[3-(Dimethylamino)propyl]-2-hydroxy-3-{5-[(4-methylpiperazin-1-yl)sulfonyl]pyridin-2-yl}-1H-indole-5-carboxamide hydrochloride;
2-Hydroxy-N-(2-methoxyethyl)-3-[5-(morpholin-4-ylsulfonyl)pyridin-2-yl]-1H-indole-5-carboxamide hydrochloride;
2-Hydroxy-3-{5-[(4-methylpiperazin-1-yl)sulfonyl]pyridin-2-yl}-N-pyridin-3-yl-1H-indole-5-carboxamide hydrochloride;
2-Hydroxy-N-(2-methoxybenzylamide)-3-{5-[(4-methylpiperazin-1-yl)sulfonyl]pyridin-2-yl}-1H-indole-5-carboxamide hydrochloride;
2-Hydroxy-N-(3-methoxybenzylamide)-3-{5-[(4-methylpiperazin-1-yl)sulfonyl]pyridin-2-yl}-1H-indole-5-carboxamide hydrochloride;
2-Hydroxy-3-{5-[(4-methylpiperazin-1-yl)sulfonyl]pyridin-2-yl}-N-(tetrahydro-2H-pyran-4-yl)-1H-indole-5-carboxamide hydrochloride;
2-Hydroxy-N-(4-methoxybenzylamide)-3-{5-[(4-methylpiperazin-1-yl)sulfonyl]pyridin-2-yl}-1H-indole-5-carboxamide hydrochloride;
N-(Cyanomethyl)-2-hydroxy-3-[5-(morpholin-4-ylmethyl)pyridin-2-yl]-1H-indole-5-carboxamide hydrochloride;
N-(2-Furylmethyl)-2-hydroxy-3-[5-(morpholin-4-ylmethyl)pyridin-2-yl]-1H-indole-5-carboxamide hydrochloride;
2-Hydroxy-3-{5-[(4-methylpiperazin-1-yl)methyl]pyridin-2-yl}-1H-indole-6-carbonitrile hydrochloride;
2-Hydroxy-3-[5-(piperidin-1-ylmethyl)pyridin-2-yl]-1H-indole-6-carbonitrile hydrochloride;
2-Hydroxy-3-{5-[(3-oxopiperazin-1-yl)methyl]pyridin-2-yl}-1H-indole-6-carbonitrile hydrochloride;
2-Hydroxy-3-[6-(2-morpholin-4-ylethoxy)pyrimidin-4-yl]-1H-indole-6-carbonitrile hydrochloride;
3-{6-[2-(Diisopropylamino)ethoxy]pyrimidin-4-yl}-2-hydroxy-1H-indole-6-carbonitrile hydrochloride;
2-Hydroxy-3-{5-[(4-methylpiperazin-1-yl)sulfonyl]pyridin-2-yl}-1H-indole-5-carboxylic acid hydrochloride;
2-Hydroxy-3-{5-[(4-methylpiperazin-1-yl)sulfonyl]pyridin-2-yl}-N-[3-(2-oxopyrrolidin-1-yl)propyl]-1H-indole-5-carboxamide hydrochloride;
2-Hydroxy-3-{5-[(4-methylpiperazin-1-yl)sulfonyl]pyridin-2-yl}-N-(2-thienylmethyl)-1H-indole-5-carboxamide hydrochloride;
2-Hydroxy-3-{5-[(4-methylpiperazin-1-yl)sulfonyl]pyridin-2-yl}-N-[2-(2-oxoimidazolidin-1-yl)ethyl]-1H-indole-5-carboxamide hydrochloride;
2-Hydroxy-3-{5-[(4-methylpiperazin-1-yl)sulfonyl]pyridin-2-yl}-N-[2-(2-thienyl)ethyl]-1H-indole-5-carboxamide hydrochloride;
N-[2-(Acetylamino)ethyl]-2-hydroxy-3-{5-[(4-methylpiperazin-1-yl)sulfonyl]pyridin-2-yl}-1H-indole-5-carboxamide hydrochloride;
N-(2-Cyanoethyl)-2-hydroxy-3-{5-[(4-methylpiperazin-1-yl)sulfonyl]pyridin-2-yl}-1H-indole-5-carboxamide hydrochloride;
N-[2-(Aminosulfonyl)ethyl]-2-hydroxy-3-{5-[(4-methylpiperazin-1-yl)sulfonyl]pyridin-2-yl}-1H-indole-5-carboxamide hydrochloride;
N-(Cyanomethyl)-2-hydroxy-3-{5-[(4-methylpiperazin-1-yl)sulfonyl]pyridin-2-yl}-1H-indole-5-carboxamide hydrochloride;
2-Hydroxy-3-[5-(4-methylpiperazine-1-sulfonyl)pyridin-2-yl]-1H-indole-5-carboxylic acid carbamoylmethylamide hydrochloride;

2-Hydroxy-3-{5-[(4-methylpiperazin-1-yl)sulfonyl]pyridin-2-yl}-N-[2-(methylsulfonyl)ethyl]-1H-indole-5-carboxamide hydrochloride;

3-(5-Diethylaminomethyl-pyridin-2-yl)-2-hydroxy-1H-indole-5-carboxylic acid (2-methanesulfonyl-ethyl)-amide hydrochloride;

2-Hydroxy-3-[5-(4-methyl-piperazin-1-ylmethyl)-pyridin-2-yl]-1H-indole-5-carboxylic acid (thiophen-2-ylmethyl)-amide dihydrochloride, or 2-Hydroxy-3-[5-(4-methyl-piperazin-1-ylmethyl)-pyridin-2-yl]-1H-indole-5-carboxylic acid benzylamide dihydrochloride;

or a free base of any foregoing hydrochloride, or a tautomer thereof, or a pharmaceutically acceptable salt of any said free base.

7. A compound selected from:

3-(4-Cyanopyridin-2-yl)-2-hydroxy-N-(2-methoxyethyl)-1H-indole-5-carboxamide;

2-Hydroxy-3-[5-(4-methylpiperazine-1-sulfonyl)pyridin-2-yl]-1H-indole-5-carboxylic acid (2-carbamoylethyl) amide;

2-Hydroxy-3-[5-(4-methyl-piperazin-1-ylmethyl)-pyridin-2-yl]-1H-indole-5-carboxylic acid methyl ester;

or a tautomer thereof, or a pharmaceutically acceptable salt thereof.

8. A pharmaceutical formulation comprising as an active ingredient a therapeutically effective amount of a compound according to claim 6 or 7 in association with a pharmaceutically acceptable carrier or diluent.

9. A method of treatment of a human suffering from Alzheimer's Disease, by administering to such a human, a therapeutically effective amount of a compound according to claim 6 or 7.

* * * * *